US010251578B2

(12) United States Patent
Peacock, III et al.

(10) Patent No.: US 10,251,578 B2
(45) Date of Patent: Apr. 9, 2019

(54) MR SPECTROSCOPY SYSTEM AND METHOD FOR DIAGNOSING PAINFUL AND NON-PAINFUL INTERVERTEBRAL DISCS

(71) Applicants: Nocimed, Inc., Redwood City, CA (US); The Regents of the University of California, Oakland, CA (US)

(72) Inventors: James Clayton Peacock, III, San Carlos, CA (US); John Patrick Claude, Redwood City, CA (US); Paul Henry Kane, Albuquerque, NM (US); Jeffrey C. Lotz, San Mateo, CA (US)

(73) Assignees: NOCIMED, INC., Redwood City, CA (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/679,734

(22) Filed: Aug. 17, 2017

(65) Prior Publication Data
US 2018/0177428 A1 Jun. 28, 2018

Related U.S. Application Data

(63) Continuation of application No. 15/185,597, filed on Jun. 17, 2016, now abandoned, which is a
(Continued)

(51) Int. Cl.
*A61B 5/00* (2006.01)
*A61B 5/055* (2006.01)
(Continued)

(52) U.S. Cl.
CPC ............ *A61B 5/055* (2013.01); *A61B 5/407* (2013.01); *A61B 5/4514* (2013.01);
(Continued)

(58) Field of Classification Search
CPC ............ A61B 5/055; G01N 33/6893; G01N 2800/28; G01R 33/48; G01R 33/56
See application file for complete search history.

(56) References Cited

U.S. PATENT DOCUMENTS

| 4,983,920 A | 1/1991 | Lampman et al. |
| 5,068,098 A | 11/1991 | Schweighardt et al. |
| (Continued) | | |

FOREIGN PATENT DOCUMENTS

| JP | S63-204143 | 8/1988 |
| JP | H05-509162 | 12/1993 |
| (Continued) | | |

OTHER PUBLICATIONS

Bartels, E.M., J.C. Fairbank, et al. (1998) "Oxygen and lactate concentrations measured in vivo in the intervertebral discs of patients with scoliosis and back pain." Spine 23 (1): 1-7; discussion 8.
(Continued)

*Primary Examiner* — Joel Lamprecht
(74) *Attorney, Agent, or Firm* — Knobbe, Martens, Olson & Bear, LLP

(57) ABSTRACT

An MR Spectroscopy (MRS) system and approach is provided for diagnosing painful and non-painful discs in chronic, severe low back pain patients (DDD-MRS). A DDD-MRS pulse sequence generates and acquires DDD-MRS spectra within intervertebral disc nuclei for later signal processing & diagnostic analysis. An interfacing DDD-MRS signal processor receives output signals of the DDD-MRS spectra acquired and is configured to optimize signal-to-noise ratio (SNR) by an automated system that selectively conducts optimal channel selection, phase and frequency correction, and frame editing as appropriate for a given acquisition series. A diagnostic processor calculates a diagnostic value for the disc based upon a weighted factor set of
(Continued)

criteria that uses MRS data extracted from the acquired and processed MRS spectra along regions associated with multiple chemicals that have been correlated to painful vs. non-painful discs. A diagnostic display provides a scaled, color coded legend and indication of results for each disc analyzed as an overlay onto a mid-sagittal T2-weighted MRI image of the lumbar spine for the patient being diagnosed. Clinical application of the embodiments provides a non-invasive, objective, pain-free, reliable approach for diagnosing painful vs. non-painful discs by simply extending and enhancing the utility of otherwise standard MRI exams of the lumbar spine.

24 Claims, 33 Drawing Sheets

Related U.S. Application Data continuation of application No. 14/310,721, filed on Jun. 20, 2014, now Pat. No. 9,392,959, which is a continuation of application No. 12/579,371, filed on Oct. 14, 2009, now Pat. No. 8,761,860.

(51) Int. Cl.
| | |
|---|---|
| *G01R 33/485* | (2006.01) |
| *G01R 33/3415* | (2006.01) |
| *G01R 33/46* | (2006.01) |
| *G01R 33/34* | (2006.01) |
| *G06F 19/00* | (2018.01) |
| *G01R 33/565* | (2006.01) |

(52) U.S. Cl.
CPC .......... *A61B 5/4824* (2013.01); *A61B 5/7203* (2013.01); *G01R 33/3415* (2013.01); *G01R 33/34069* (2013.01); *G01R 33/4616* (2013.01); *G01R 33/485* (2013.01); *G01R 33/56527* (2013.01); *G06F 19/00* (2013.01); *G01R 33/565* (2013.01)

(56) References Cited

U.S. PATENT DOCUMENTS

| | | | |
|---|---|---|---|
| 5,190,039 A | 3/1993 | Takeuchi | |
| 5,201,311 A | 4/1993 | Bottomley et al. | |
| 5,207,715 A | 5/1993 | Fossel | |
| 5,270,651 A | 12/1993 | Wehrli | |
| 5,617,861 A | 4/1997 | Ross et al. | |
| 5,844,097 A | 12/1998 | Cameron, Sr. et al. | |
| 5,903,149 A | 5/1999 | Gonen et al. | |
| 6,018,675 A | 1/2000 | Apkarian et al. | |
| 6,069,478 A | 5/2000 | Hurd | |
| 6,278,891 B1 | 8/2001 | Reiderman et al. | |
| 6,418,335 B2 | 7/2002 | Avrin | |
| 6,472,871 B2 | 10/2002 | Ryner | |
| 6,552,541 B2 | 4/2003 | Nauerth | |
| 6,617,169 B2 | 9/2003 | Ke et al. | |
| 6,639,405 B2 | 10/2003 | Liu et al. | |
| 6,674,282 B2 | 1/2004 | Pines et al. | |
| 6,683,455 B2 | 1/2004 | Ebbels et al. | |
| 6,686,348 B2 | 2/2004 | De Nanteuil et al. | |
| 6,795,567 B1 | 9/2004 | Cham et al. | |
| 6,835,572 B1 | 12/2004 | Mountford et al. | |
| 6,836,114 B2 | 12/2004 | Reddy et al. | |
| 6,943,033 B2 | 9/2005 | Van Zijl et al. | |
| 6,987,997 B1 | 1/2006 | Hurd et al. | |
| 7,027,054 B1 | 4/2006 | Cheiky et al. | |
| 7,042,214 B2 | 5/2006 | Cunningham et al. | |
| 7,116,104 B2 | 10/2006 | Reddy et al. | |
| 7,123,009 B1 | 10/2006 | Scott | |
| 7,181,348 B2 | 2/2007 | Wishart et al. | |
| 7,184,813 B1 | 2/2007 | Hurd et al. | |
| 7,288,521 B2 | 10/2007 | Franco | |
| 7,319,784 B2 | 1/2008 | Ryner et al. | |
| 7,323,871 B2 | 1/2008 | Foo | |
| 7,411,396 B1 | 8/2008 | Schirmer et al. | |
| 7,499,745 B2 | 3/2009 | Littrup | |
| 7,676,254 B2 | 3/2010 | Siddall et al. | |
| 7,705,596 B2 | 4/2010 | Witschey et al. | |
| 7,741,844 B2 | 6/2010 | Hancu et al. | |
| 7,749,275 B2 | 7/2010 | Lambrecht et al. | |
| 7,940,264 B2 | 5/2011 | Jojic et al. | |
| 8,018,570 B2 | 9/2011 | Kameyama | |
| 8,076,936 B2 | 12/2011 | Borthakur et al. | |
| 8,208,709 B2 | 6/2012 | Ding et al. | |
| 8,344,728 B2 | 1/2013 | Majumdar et al. | |
| 8,478,380 B2 | 7/2013 | Soher | |
| 8,553,037 B2 | 10/2013 | Smith et al. | |
| 8,615,285 B2 | 12/2013 | Ehman | |
| 8,668,647 B2 | 3/2014 | Eskandari | |
| 8,690,057 B2 | 4/2014 | Schoening et al. | |
| 8,761,860 B2 | 6/2014 | Peacock, III et al. | |
| 8,798,351 B2 | 8/2014 | Ding et al. | |
| 8,825,131 B2 | 9/2014 | Peacock, III et al. | |
| 8,965,094 B2 | 2/2015 | Peacock, III et al. | |
| 9,161,735 B2 | 10/2015 | Bradford et al. | |
| 9,280,718 B2 | 3/2016 | Claude et al. | |
| 9,345,421 B2 | 5/2016 | Peacock, III et al. | |
| 9,392,959 B2 | 7/2016 | Peacock, III et al. | |
| 9,724,013 B2 | 8/2017 | Peacock, III et al. | |
| 9,808,177 B2 | 11/2017 | Claude et al. | |
| 9,901,285 B2 | 2/2018 | Majumdar et al. | |
| 10,045,711 B2 | 8/2018 | Peacock, III et al. | |
| 2001/0003423 A1 | 6/2001 | Wald | |
| 2002/0037251 A1 | 3/2002 | Driehuys | |
| 2004/0006376 A1 | 1/2004 | Falci | |
| 2004/0214348 A1 | 10/2004 | Nicholson et al. | |
| 2005/0024051 A1 | 3/2005 | Doddrell et al. | |
| 2005/0054910 A1 | 3/2005 | Tremblay et al. | |
| 2005/0240104 A1 | 10/2005 | Shim et al. | |
| 2005/0251025 A1* | 11/2005 | Hancu .................. | A61B 5/055 600/420 |
| 2007/0167729 A1* | 7/2007 | Mistretta ............. | G01R 33/4824 600/410 |
| 2007/0253910 A1 | 11/2007 | Ahrens et al. | |
| 2008/0039710 A1* | 2/2008 | Majumdar ............ | A61B 5/055 600/410 |
| 2008/0220530 A1 | 9/2008 | Bahn et al. | |
| 2008/0226148 A1 | 9/2008 | Gu et al. | |
| 2009/0076481 A1 | 3/2009 | Stegmann et al. | |
| 2009/0134869 A1 | 5/2009 | Lee | |
| 2009/0191131 A1 | 7/2009 | Fossheim et al. | |
| 2009/0261823 A1 | 10/2009 | Yu et al. | |
| 2010/0086185 A1 | 4/2010 | Weiss | |
| 2010/0121210 A1 | 5/2010 | Lindner | |
| 2010/0136588 A1 | 6/2010 | Colgin | |
| 2010/0166278 A1 | 7/2010 | Witschey | |
| 2010/0244834 A1 | 9/2010 | Mori et al. | |
| 2010/0264920 A1 | 10/2010 | Witschey et al. | |
| 2010/0268225 A1 | 10/2010 | Coe et al. | |
| 2011/0087087 A1* | 4/2011 | Peacock, III ......... | A61B 5/055 600/410 |
| 2011/0230755 A1 | 9/2011 | MacFarlane et al. | |
| 2011/0286630 A1 | 11/2011 | Harder | |
| 2012/0155731 A1 | 6/2012 | Weersink et al. | |
| 2014/0119631 A1 | 5/2014 | Mostafavi | |
| 2015/0119688 A1 | 4/2015 | Peacock, III et al. | |
| 2016/0136310 A1 | 5/2016 | Bradford et al. | |
| 2017/0105650 A1 | 4/2017 | Peacock, III et al. | |
| 2018/0055405 A1 | 3/2018 | Peacock, III et al. | |
| 2018/0317802 A1 | 11/2018 | Majumdar et al. | |

FOREIGN PATENT DOCUMENTS

| | | |
|---|---|---|
| JP | H06-503418 | 4/1994 |
| JP | 2003524490 | 8/2003 |
| JP | 2004526130 | 8/2004 |
| JP | 2004528559 | 9/2004 |
| KR | 10-2011-0100046 | 9/2011 |

(56) References Cited

FOREIGN PATENT DOCUMENTS

| | | |
|---|---|---|
| WO | WO 2006/081471 | 8/2006 |
| WO | WO 2007/035906 | 3/2007 |
| WO | WO 2009/058915 | 5/2009 |
| WO | WO 2009/148550 | 12/2009 |
| WO | WO 2011/047197 | 4/2011 |
| WO | WO 2011/060237 | 5/2011 |
| WO | WO 2011/146798 | 11/2011 |
| WO | WO 2012/071566 | 5/2012 |

OTHER PUBLICATIONS

Bottomley PA. "Spatial localization in NMR spectroscopy in vivo." Ann N Y Acad Sci 1987; 508:333-348.
Brown TR, Kincaid BM, Ugurbil K. "NMR chemical shift imaging in three dimensions." Proc. Natl. Acad. Sci. USA 1982; 79:3523-3526.
Brown, M.F., M.V. Hukkanen, et al. (1997). "Sensory and sympathetic innervation of the vertebral endplate in patients with degenerative disc disease." J Bone Joint Surg Br 79(1): 147-53.
Buenaventura, R.M., R.V. Shah, et al. (2007). "Systematic review of discography as a diagnostic test for spinal pain: an update." Pain Physician 10(1): 147-64.
Carragee et al., "2009 ISSLS Prize Winner: Does Discography Cause Accelerated Progression of Degeneration Changes in the Lumbar Disc," SPINE vol. 34, No. 21, pp. 2338-2345,2009.
Carragee, E. J., T. Lincoln, et al. (2006). "A gold standard evaluation of the "discogenic pain" diagnosis and determined by provocative discography." Spine 31(18): 2115-23.
Carragee, E.J. and T.F. Alamin (2001). "Discography, a review." Spine J 1(5): 364-72.
Carragee, E.J., T.F. Alamin, et al. (2006). "Low-pressure positive Discography in subjects asymptomatic of significant low back pain illness." Spine 31(5): 505-9.
Cohen, S.P., T.M. Larkin, et al. (2005). "Lumbar discography: a comprehensive review of outcome studies, diagnostic accuracy, and principles." Reg Anesth Pain Med 30(2): 163-83.
Coppes, M.H., E. Marani, et al. (1997). "Innervation of "painful" lumbar discs." Spine 22(20): 2342-49.
Cunningham CH, Vigneron DB, Chen AP, Xu D, Hurd RE, Sailasuta N, Pauly JM. "Design of symmetric-sweep spectral-spatial RF pulses for spectral editing." Magn Reson Med 2004; 52: 147-153.
Derby, R., R.M. Baker, et al. (2008). "Analgesic Discography: Can Analgesic Testing Identify a Painful Disc?" SpineLine (Nov.-Dec.): 17-24.
Diamant, B., J. Karlsson, et al. (1968). "Correlation between lactate levels and pH in discs of patients with lumbar rhizopathies." Experientia 24(12): 1195-6.
Jiru, F., "Introduction to Post-Processing Techniques," Europeant Journal of Radiology 67, (2008) 202-217.
Frahm J, Bruhn H, Gyngell ML, Merboldt KD, Hanicke W, Sauter R. "Localized high-resolution proton NMR spectroscopy using stimulated echoes: initial applications to human brain in vivo." Magn Reson Med 1989; 9:79-93.
Freemont, A.J., A. Watkins, et al. (2002). "Nerve growth factor expression and innervation of the painful intervertebral disc." J Pathol 197(3): 286-92.
Freemont, A.J., T.E. Peacock, et al. (1997). "Nerve ingrowth into diseased intervertebral disc in chronic back pain." Lancet 350(9072): 178-81.
Grunhagen, T., G. Wilde, et al. (2006). "Nutrient supply and intervertebral disc metabolism." J Bone Joint Surg Am 88 Suppl 2: 30-5.
Guyer, R.D. and D.D. Ohnmeiss (2003). "Lumbar discography." Spine J 3(3 Suppl): 11S-27S.
Immke, D. C. and E.W. McCleskey (2001). "Lactate enhances the acid-sensing Na+ channel on ischemia-sensing neurons." Nat Neurosci 4(9): 869-70.
Ishihara, H. and J.P. Urban (1999). "Effects of low oxygen concentrations and metabolic inhibitors on proteoglycan and protein synthesis rates in the intervertebral disc." J Orthop Res 17(6): 829-35.
Jain, A., S.M Brady-Kalnay, et al. (2004). "Modulation of Rho GTPase activity alleviates chondroitin sulfate proteoglycan-dependent inhibition of neurite extension." J Neurosci Res 77(2): 299-307.
Jones, L.L., D. Sajed, et al. (2003). "Axonal regeneration through regions of chondroitin sulfate proteoglycan deposition after spinal cord injury: a balance of permissiveness and inhibition." J Neurosci 23(28): 9276-88.
Keshari, K. R., A. S. Zektzer, et al. (2005). "Characterization of intervertebral disc degeneration by high-resolution magic angle spinning (HR-MAS) spectroscopy." Magn Reson Med 53(3): 519-27.
Keshari, K.R., J.C. Lotz, et al. (Dec. 1, 2005). "Correlation of HR-MAS spectroscopy derived metabolite concentrations with collagen and proteoglycan levels and Thompson grade in the degenerative disc." Spine 30(23): 2683-88.
Keshari, K.R., J.C. Lotz, et al. (2008). "Lactic acid and proteoglycans as metabolic markers for discogenic back pain." Spine 33(3): 312-317.
Klapka, N. and H. W. Muller (2006). "Collagen matrix in spinal cord injury." J Neurotrauma 23(3-4): 422-35.
Molliver, D. C., D. C. Immke, et al. (2005). "ASIC3, an acid-sensing ion channel, is expressed in metaboreceptive sensory neurons." Mol Pain 1: 35.
Nachemson, A. (1969). "Intradiscal measurements of pH in patients with lumbar rhizopathies." Acta Orthop Scand 40(1): 23-42.
Naves, L. A. and E. W. McCleskey (2005). "An acid-sensing ion channel that detects ischemic pain." Braz J Med Biol Res 38(11): 1561-9.
O'Neill, C. and M. Kurgansky (2004). "Subgroups of positive discs on discography." Spine 29(19): 2134-9.
Pauly J, Le Roux P, Nishimura D, Macovski A. "Parameter relations for the Shinnar-Le Roux selective excitation pulse design algorithm [NMR imaging]." IEEE Trans Med Imaging 1991; 10: 53-65.
Properzi, F., R. A. Asher, et al. (2003). "Chondroitin sulphate proteoglycans in the central nervous system: changes and synthesis after injury." Biochem Soc Trans 31(2): 335-6.
Roberts, S., H. Evans, et al. (2006). "Histology and pathology of the human intervertebral disc." J Bone Joint Surg Am 88 Suppl 2: 10-14.
Roughley, P. J., M. Alini, et al. (2002). "The role of proteoglycans in aging, degeneration and repair of the intervertebral disc." Biochem Soc Trans 30(Pt 6): 869-74.
Rukwied, R., B. A. Chizh, et al. (2007). "Potentiation of nociceptive responses to low pH injections in humans by prostaglandin E2." J Pain 8(5): 443-51.
Scuderi, G. J., G. V. Brusovanik, et al. (2008). "A critical evaluation of discography in patients with lumbar intervertebral disc disease." Spine J 8(4): 624-9.
Star-Lack J, Nelson SJ, Kurhanewicz J, Huang LR, Vigneron DB. "Improved water and lipid suppression for 3D Press CSI using RF bank selective inversion with gradient dephasing (BASING)." Magn Reson Med 1997; 38: 311-321.
Sutherland, S. P., C. J. Benson, et al. (2001). "Acid-sensing ion channel 3 matches the acid-gated current in cardiac ischemia-sensing neurons." Proc Natl Acad Sci U S A 98(2): 711-6.
Urban, J. P., S. Smith, et al. (2004). "Nutrition of the intervertebral disc." Spine 29(23): 2700-9.
Wichman, H. J. (2007). "Discography: over 50 years of controversy." Wmj 106(1): 27-9.
Wolfer, L. R., R. Derby, et al. (2008). "Systematic review of lumbar provocation discography in asymptomatic subjects with a meta-analysis of false-positive rates." Pain Physician 11(4): 513-38.
Mari Garseth et al. "Metabolic changes in the cerebrospinal fluid of patients with lumbar disc herniation or spinal stenosis." Journal of Neuroscience Research, vol. 69, No. 5, Sep. 1, 2002, pp. 692-695.
Henning A. et al. "Spinal cord MRS in and beyond the cerival spine", Proceedings of the International Society for Magnetic Resonance in Medicine, May 6, 2006, p. 889.

(56) References Cited

OTHER PUBLICATIONS

Zuo, J., D. Neubauer, et al. (1998). "Degradation of chondroitin sulfate proteoglycan enhances the neurite-promoting potential of spinal cord tissue." Exp Neurol 154(2): 654-62.

Zuo, J., Y. J. Hernandez, et al. (1998). "Chondroitin sulfate proteoglycan with neurite-inhibiting activity is up-regulated following peripheral nerve injury." J Neurobiol 34(1): 41-54.

Zuo, J., et al. "MR Spectroscopy in intervertebral disc and correlation with biochemical analysis." Proceedings of the International Society for Magnetic Resonance in Medicine, Apr. 18, 2009, p. 2002.

Zuo, J. et al. "Quantification of relaxation times of metabolite resonance in intervertebral disc using MR Spectroscopy", Proceedings of the International Society for Magnetic Resonance in Medicine, Apr. 18, 2009, p. 2001.

Haro, H. et al. "Matrix metalloproteinase-7-dependent release of tumor necrosis factor in a model of herniated disc resorption," Jour. Of Clinical Inv., vol. 105, No. 2, Jan. 2000, pp. 143-150.

Mow, V.C. et al. "Basic Orthopaedic Biomechanics—Chapter 10—Bomechanics of the Human Spine," 1997, pp. 353-393.

Thompson, J. et al. "Preliminary Evaluation of a Scheme for Grading the Gross Morphology of the Human Intervertebral Disc," Spine, vol. 15, 1990, pp. 411-415.

Iatridis, J. et al. "Alterations in the Mechanical Behavior of the Human Lumbar Nucleas Pulposus with Degeneration and Aging," Jour. Of Ortho Research, vol. 15, 1997, pp. 318-322.

Beall, et al. "NMR Data Handbook for Biomedical Applications," New York, Pergamon Press, 1984, 11 pages.

Boos, N. et al.—Quantitative Magnetic Resonance Imaging of the Lumbar Spine, Spine, vol. 20, No. 21, pp. 2358-2366.

Bottomley, P. et al. "A review of normal tissue hydrogen NMR relaxation times and relaxation mechanisms from 1-100 MHz: Dependence on tissue type, NMR frequency, temperature, species, excision and age," Med. Phys., vol. 11, No. 4, Jul./Aug. 1984, pp. 425-448.

Lyons, G. et al. "Biochemical Changes in Intervertebral Disc Degeneration," Biochimica Biophys Acta, vol. 673, 1981, pp. 443-453.

Maroudas, A.—"The Biology of the Intervertebral Disc"—In: Ghosh, P. el. The Biology of the Intervertebral Disc, vol. II, Chapter 9, 1988.

Pearce, R. et al.—"Degeneration and the Chemical Composition of the Human Lumbar Intervertebral Disc"—Jour. of Ortho. Research, vol. 5, 1987, pp. 198-205.

Tertii, M. et al.—"Disc Degeneration in Magnetic Resonance Imaging: A Comparative Biochemical, Histologic, and Radiologic Study in Cadaver Spines"—Spine, 1991, pp. 629-634.

Chiu, E. et al.—"Magnetic Resonance Imaging Measurement of Relaxation and Water Diffusion in the Human Lumbar Intervertebral Disc Under Compression in Vitro"—Spine, vol. 26, No. 19,2001, pp. E437-E444.

Gundry, C. et al.—"Magnetic Resonance Imaging of the Musculoskeletal System, Part 8. The Spine, Section 1 ", Clinical Ortho. and Related Research, vol. 338, May 1997, pp. 275-287.

Gunzburg, R. et al.—"A Cadaveric Study Comparing Discography, Magnetic Resonance Imaging, Histology, and Mechanical Behavior of the Human Lumbar Disc"—Spine, 1991, pp. 417-426.

Modic, M. et al.—"Magnetic Resonance Imaging of Intervertebral Disk Disease"—Radiology, vol. 152, 1984, pp. I03-111.

Modic, M. et al.—"Lumbar Herniated Disk Disease and Canal Stenosis: Prospective Evaluation by Surface Coil MR, CT, and Myelography"—AJR, vol. 147, Oct. 1986, pp. 757-765.

Modic, M. et al.—"Imaging of Degenerative Disk Disease"—Radiology, vol. 168, 1988, pp. 177-186.

Sether, L. et al.—"Intervertebral Disk: Normal Age-related Changes in MR Signal Intensity"—Radiology, vol. 177, 1990, pp. 385-388.

Pfirrmann, C. et al.—"Magnetic Resonance Classification of Lumbar Intervertebral Disc Degeneration"—Spine, vol. 26, No. 17, pp. 1873-1878.

Nieminen, M. et al.—"Spatial Assessment of Articular Cartilage Proteoglycans with Gd-DTPA-Enhanced TI Imaging"—Mag. Res. in Med., vol. 48, 2002, pp. 640-648.

Mosher, T. et al.—"Human Articular Cartilage: Influence of Aging and Early Symptomatic Degeneration on the Spatial Variation of T2-Preliminary Findings at 3 TI"—Radiology, vol. 214, 2000, pp. 259-266.

Burstein, D. et al.—"Diffusion of Small Solutes in Cartilage as Measured by Nuclear Magnetic Resonance (NMR) Spectroscopy and Imaging"—Jour. of Ortho. Res., vol. 11, 1993, pp. 465-478.

Abdulkarim, J. et al.—"Magnetic Resonance Imaging of the Cervical Spine: Frequency of Degenerative Changes in the Intervertebral Disc With Relation to Age"—Clinical Radiology, vol. 58, 2003, pp. 980-984.

Swanson, M. et al.—"Proton HR-MAS Spectroscopy and Quantitative Pathologic Analysis of MRI/3D-MRSI-Targeted Postsurgical Prostate Tissues"—Mag. Resonance in Med., vol. 54, 2003, pp. 944-954.

Schiller, J., et al. "H and C-13 HR-MAS NMR Investigations on Native and Enzymatically Digested Bovine Nasal Certilage." Magnetic Resonance Materials in Physics 2001; 13:19-27.

Carr, H. et al.—"Effects of Diffusion on Free Precession in Nuclear Magnetic Resonance Experiments"—Phys. Review, vol. 94, No. 3, May 1, 1954, pp. 630-638.

Kupce, E.—"Applications of Adiabatic Pulses in Biomolecular Nuclear Magnetic Resonance"—Methods in Enzymology, vol. 338, 2001, pp. 82-111.

Mucci, A. et al.—"1 Hand 13C nuclear magnetic resonance identification and characterization of components of chondroitin sulfates of various origin"—Carbohydrate Polymers, vol. 41, 2003, pp. 37-45.

Groupille, P. et al.—"Matrix Metalloproteinases: The Clue to Intervertebral Disc Degeneration?"—Spine, vol. 23, No. 14, Jul. 1998, pp. 1612-1626.

Kang, J. et al.—"Towards a Biochemical Understanding of Human Intervertebral Disc Degeneration and Herniation: Contributions of Nitric Oxide, Interleukins, Prostaglandin E2, and Matrix Metalloproteinases"—spine, vol. 22, No. 10, May 15, 1997, pp. 1065-1073.

Weiler, C. et al.—"2002 SSE Award Competition in Basic Science: Expression of major matrix metalloproteinases is associated with intervertebral disc degradation and resorption"—Eur. Spine Jour., vol. 11, 2002, pp. 308-320.

Urban, J. et al.—"The Nucleus of the Intervertebral Disc from Development to Degeneration"—American Zoologist, vol. 40, No. 1, Feb. 2000, pp. 53-61.

Weidenbaum, M. et al.—"Correlating Magnetic Resonance Imaging with the Biochemical Content of the Normal Human Intervertebral Disc"—Jour. of Ortho. Research, vol. 10, 1992, pp. 552-561.

Boos, N. et al.—"Quantitative MR Imaging of Lumbar Intervertebral Disks and Vertebral Bodies: Influence of Diurnal Water Content Variations"—Radiology, vol. 188, 1993, pp. 351-354.

Boos, N. et al.—"Quantitative MR Imaging of Lumbar Intervertebral Discs and Vertebral Bodies: Methodology, Reproducibility, and Preliminary Results"—Mag. Res. Imaging, vol. 12, No. 4,1994, pp. 577-587.

Keshari, K et al.—Poster and Abstract—"Identification of Chondroitin Sulfate as a Marker for Human Intervertebral disc Degeneration Using Proton High Resolution Magic Angle Spinning HR-MAS) Spectroscopy"—The 44th ENC, Mar. 30-Apr. 4, 2003, 22 pages.

Majumdar, S.—Abstract—"Spectroscopic Markers of Disc Degeneration."—downloaded from CRISP website Nov. 23, 2004, 2 pages.

Petrantonaki, M., et al. "MRI Techniques for the Examination of Trabecular Bone Structure." Current Medical Imaging Reviews 2005, 1:35-41.

Ford, J. C., et al. "In Vivo Quantitative Characterization of Trabecular Bone by NMR Interferometry and Localized Proton Spectroscopy." Magnetic Resonance in Medicine 1991; 17: 543-551.

Schiller, J., et al. "Evaluation of Cartilage Composition and Degradation by High-Resolution Magic-Angle Spinning Nuclear Magnetic Resonance." Methods in Molecular Medicine 2004; 101:267-285.

(56) References Cited

OTHER PUBLICATIONS

Chung, C. T., et al. "Single photon emission computed tomography (SPECT) for low back pain induced by extension with no root sign." J. Chin. Med. Assoc. vol. 67, pp. 349-354 (2004).
Lusins, J. O., et al. "SPECT and lumbar MRI in back pain with emphasis on changes in end plates in association with disc degeneration (abstract)." J. Neuroimaging, vol. 8, No. 2, pp. 78-82 (1998).
McDonald, M., et al. "Use of computer tomography—single-photon emission computed tomography fusion for diagnosing painful facet arthropathy." Neurosurg. Focus, vol. 22, No. 1, E2 (2007).
Mulconrey, D. S., et al. "Interobserver reliability in the interpretation of diagnostic lumbar MRI and Nuclear imaging." The Spine Journal, vol. 6, pp. 177-184 (2006).
Keshari, K., et al. "Potential metabolic markers for intervertebral disc pain." Proc. Intl. Soc. Mag. Reson. Med. 14, p. 1710. May 9, 2006.
Savvopoulou, V., et al. "Degenerative Endplate Changes of the Lumbosacral Spine: Dynamic Contrast-Enhanced MRI Profiles Related to Age, Sex, and Spinal Level." Journal of Magnetic Resonance Imaging 33:382-389 (2011).
Hassler, O. "The Human Intervertebral Disc: A Micro-Angiographical Study on Its Vascular Supply at Various Ages." Acta Orthop. Scandinav. 40, 765-772, 1970.
Niinimaki, J., et al. "Association of lumbar artery narrowing, degenerative changes in disc and endplate and apparent diffusion in disc on postcontrast enhancement of lumbar intervertebral disc." Magn. Reson. Mater Phy. 22:101-109 (2009).
Rajasekaran, S., et al. "ISSLS Prize Winner: A Study of Diffusion in Human Lumbar Discs: A Serial Magnetic Resonance Imaging Study Documenting the Influence of the Endplate on Diffusion in Normal and Degenerate Discs." SPINE vol. 29, No. 23, pp. 2654-2667 (2004).
Liu, Y., et al. "Intervertebral Disk Degeneration Related to Reduced Vertebral Marrow Perfusion at Dynamic Contrast-Enhanced MRI." AJR:192: 974-979, Apr. 2009.
Bolan, Patrick J., et al., "Measurement and Correction of Repiration-Induced Bo Variations in Breast 1H MRS at 4 Tesla," Magnetic Resonance in Medicine 52:000-000 (2004).
Lorenz, C., et al. "3D Statistical Shape Models for Medical Image Segmentation," pp. 414-423, Second International Conference on 3-D Imaging and Modeling (3DIM '99), 1999.
Lin C S et al: "2D CSI proton MR spectroscopy of human spinal vertebra: feasibility studies.", Journal of Magnetic Resonance Imaging : JM RI Mar. 2000, vol. II, No. 3, Mar. 2000, pp. 287-293.
"Spectroscopy reconstruction" and "Spectroscopy processing" In: "Intera Spectroscopy—Instructions for Use", Jul. 2002 (Jul. 2002), Philips Medical Systems, Netherlands, pp. 6-1 to 7-6.
Dubey P. et al.: "Proton MR Spectroscopic Imaging of the Human Cervical Spine at 3 Tesla", Proceedings of the International Society for Magnetic Resonance in Medicine, 13th Meeting Proceedings, May 7, 2005 (May 7, 2005), p. 812.
Majumdar, "Review Article Magnetic resonance imaging and spectroscopy of the intervertebral disc," NMR in Biomed (2006) 19: 894-903.
Carragee et al., "Prospective Controlled Study of the Development of Lower Back Pain in Previously Asymptomatic Subjects Undergoing Experimental Discography." SPINE vol. 29, No. 10, pp. 1112-1117 (2004).
Carrino et al., "Prospective evaluation of contrast-enhanced MR imaging after uncomplicated lumbar discography." Skeletal Radiol (2007) 36:293-299.
Derincek et al., "Discography: can pain in a morphologically normal disc be due to an adjacent abnormal disc?" Arch Orthop Trauma Surg (2007) 127:699-703.
Boden et al., "Abnormal magnetic-resonance scans of the lumbar spine in asymptomatic subjects. A prospective investigation." The Journal of Bone & Joint Surgery (1990) 72:403-408.
Boos et al., "Natural History of Individuals With Asymptomatic Disc Abnormalities in Magnetic Resonance Imaging; Predictors of Low Back Pain-Related Medical Consultation and Work Incapacity." SPINE vol. 25, No. 12, pp. 1484-1492 (2000).
Borenstein et al., "The Value of Magnetic Resonance Imaging of the Lumbar Spine to Predict Low-Back Pain in Asymptomatic Subjects: A Seven-Year Follow-up Study." The Journal of Bone & Joint Surgery (2001) 83:1306-1311.
Carragee et al., "2004 Outstanding Paper Award: Nonoperative Science; Discographic, MRI and psychosocial determinants of low back pain disability and remission: a prospective study in subjects with benign persistent back pain." The Spine Journal 5 (2005) 24-35.
Cherkin et al., "Physician Variation in Diagnostic Testing for Low Back Pain." Arthritis & Rheumatism, vol. 37, No. 1, Jan. 1994, pp. 15-22.
Freeborn et al., Primary Care Physicians' Use of Lumbar Spine Imaging Tests: Effects of Guidelines and Practice Pattern Feedback. JGIM, vol. 12, Oct. 1997, pp. 619-625.
Peng Z, "Automated Vertebra Detection and Segmentation from the Whole Spine MR Images," Proceedings of the 2005 IEEE Engineering in Medicine and Biology 27th Annual Conference, Shanghai, China, Sep. 1-4, 2005.
Wu M et al., "Quantitative comparison of AIR, SPM, and the fully deformable model for atlas-based segmentation of functional and structural MR images." Hum Brain Mapp. Sep. 2006; 27(9):747-54.
Liu J et al., "Rigid model-based 3D segmentation of the bones of joints in MR and CT images for motion analysis." Med Phys. Aug. 2008;35(8):3637-49.
Liu J et al., "Oriented active shape models." IEEE Trans Med Imaging. Apr. 2009; 28(4):571-84.
Chevrefils C et al., "Texture analysis for automatic segmentation of intervertebral disks of scoliotic spines from MR images." IEEE Trans Inf Technol Biomed. Jul. 2009; 13(4):608-20.
Huang SH et al., "Learning-based vertebra detection and iterative normalized-cut segmentation for spinal MRI." IEEE Trans Med Imaging. Oct. 2009; 28(10):1595-605.
Michopoulou SK et al., "Atlas-based segmentation of degenerated lumbar intervertebral discs from MR images of the spine." IEEE Trans Biomed Eng. Sep. 2009; 56(9):2225-31.
Kadoury S et al., "Personalized X-ray 3-D reconstruction of the scoliotic spine from hybrid statistical and image-based models." IEEE Trans Med Imaging. Sep. 2009; 28(9):1422-35.
Koh J et al., "Automatic segmentation of the spinal cord and the dural sac in lumbar MR images using gradient vector flow field." Conf Proc IEEE Eng Med Biol Soc. 2010; 2010:3117-20.
Hao S et al., "[Spine disc MR image analysis using improved independent component analysis based active appearance model and Markov random field]." Sheng Wu Yi Xue Gong Cheng Xue Za Zhi. Feb. 2010;27(1):6-9, 15.
Horsfield MA et al., "Rapid semi-automatic segmentation of the spinal cord from magnetic resonance images: application in multiple sclerosis." Neuroimage. Apr. 1, 2010; 50(2):446-55.
Bechara BP et al., "Application of a semiautomated contour segmentation tool to identify the intervertebral nucleus pulposus in MR images." AJNR Am J Neuroradiol. Oct. 2010; 31(9):1640-4.
Ben Ayed I et al., "Graph cuts with invariant object-interaction priors: application to intervertebral disc segmentation." Inf Process Med Imaging. 2011;22:221-32.
Dalca A et al., "Segmentation of nerve bundles and ganglia in spine MRI using particle filters." Med Image Comput Comput Assist Interv. 2011; 14(Pt 3):537-45.
Michopoulou S et. al., "Texture-based quantification of lumbar intervertebral disc degeneration from conventional T2-weighted MRI," Acta Radiologica 2011; 52: 91-98.
Neubert A, "Automated 3D Segmentation of Vertebral Bodies and Intervertebral Discs from MRI," 2011 International Conference on Digital Image Computing: Techniques and Applications.
Strickland CG et al., "Development of subject-specific geometric spine model through use of automated active contour segmentation and kinematic constraint-limited registration." J Digit Imaging. Oct. 2011; 24(5):926-42.
Giulietti G et al., "Semiautomated segmentation of the human spine based on echoplanar images," Magn Reson Imaging. Dec. 2011; 29(10):1429-36.

(56) References Cited

OTHER PUBLICATIONS

Stern D et al., "Parametric modelling and segmentation of vertebral bodies in 3D CT and MR spine images." Phys Med Biol. Dec. 7, 2011; 56(23):7505-22.
Neubert A et. al., "Automated detection, 3D segmentation and analysis of high resolution spine MR images using statistical shape models." Phys Med Biol. Dec. 21, 2012; 57(24):8357-76.
Egger J et al., "Square-cut: a segmentation algorithm on the basis of a rectangle shape." PLoS One. Dated Feb. 2012. 7(2).
Vrtovec T et al., "Automated curved planar reformation of 3D spine images." Phys Med Biol. Oct. 7, 2005; 50(19):4527-40.
Bandettini, Patricia et al., "MultiContrast Delayed Enhancement (MCODE) improves detection of subendocardial myocardial infarction by late gadolinium enhancement cardiovascular magnetic resonance: a clinical validation study", Journal of Cardiovascular Magnetic Resonance, vol . 14, No. I, Nov. 30, 2012 (Nov. 30, 2012).
Comments Regarding U.S. Appl. No. 12/579,371, filed Oct. 14, 2009 and PCT Patent Application No. PCT/US2010/052737 (Filed Oct. 14, 2010).
Vos T, Flaxman AD, Naghavi M, et al. Dec. 2012. Years lived with disability (YLDs) for 1160 sequelae of 289 diseases and injuries 1990-2010: a systematic analysis for the Global Burden of Disease Study 2010. Lancet 380(9859):2163-96.
Thompson KJ, Dagher AP, Eckel TS, et al. Mar. 2009. Modic changes on MR images as studied with provocative diskography: clinical relevance—a retrospective study of 2457 disks. Radiology 250(3):849-55.
Modic MT, Steinberg PM, Ross JS, et al. Jan. 1988. Degenerative disk disease: assessment of changes in vertebral body marrow with MR imaging. Radiology 166(1 Pt 1): 193-9.
Jensen TS, Karppinen J, Sorensen JS, et al. Sep. 12, 2008. Vertebral endplate signal changes (Modic change): a systematic literature review of prevalence and association with non-specific low back pain. Eur. Spine J. 17(11): 1407-22.
Jensen OK, Nielsen CV, Sorensen JS, Stengaard-Pedersen K. Nov. 1, 2014. Type 1 Modic changes was a significant risk factor for 1-year outcome in sick-listed low back pain patients: a nested cohort study using magnetic resonance imaging of the lumbar spine. Spine J. 14(11):2568-81.
Schistad EL, Espeland A, Rygh LJ, et al. Jun. 26, 2014. The association between Modic changes and pain during 1-year follow-up in patients with lumbar radicular pain. Skeletal Radiol. 43(9):1271-9.
Jarvinen J, Karppinen J, Niinimäki J, et al. Apr. 22, 2015. Association between changes in lumbar Modic changes and low back symptoms over a two-year period. BMC Musculoskelet. Disord. 16(1):98.
Albert HB, Lambert P, Rollason J, et al. Feb. 10, 2013. Does nuclear tissue infected with bacteria following disc herniations lead to Modic changes in the adjacent vertebrae? Eur. Spine J. 22(4):690-6.
Vowels BR, Yang S, Leyden JJ. Aug. 1995. Induction of proinflammatory cytokines by a soluble factor of Propionibacterium acnes: implications for chronic inflammatory acne. Infect. Immun. 63(8):3158-65.
McDowell A, Barnard E, Nagy I, et al. Jul. 2012. An expanded multilocus sequence typing scheme for propionibacterium acnes: investigation of "pathogenic", "commensal" and antibiotic resistant strains. PLoS One 7(7):e41480.
Valanne S, McDowell A, Ramage G, et al. May 2005. CAMP factor homologues in Propionibacterium acnes: A new protein family differentially expressed by types I and II. Microbiology 151(5):1369-1379.
Stirling A, Worthington T, Rafiq M, et al. Jun. 23, 2001. Association between sciatica and Propionibacterium acnes. Lancet 357(9273):2024-5.
Rollason J, McDowell A, Albert HB, et al. Aug. 2013. Genotypic and antimicrobial characterisation of Propionibacterium acnes isolates from surgically excised lumbar disc herniations. Biomed Res. Int. 2013:530382.

Albert HB, Sorensen JS, Christensen BS, Manniche C. Feb. 13, 2013. Antibiotic treatment in patients with chronic low back pain and vertebral bone edema (Modic type 1 changes): a double-blind randomized clinical controlled trial of efficacy. Eur. Spine J. 22(4):697-707.
Fritzell P, Bergstrom T, Welinder-Olsson C. May 8, 2004. Detection of bacterial DNA in painful degenerated spinal discs in patients without signs of clinical infection. Eur. Spine J. 13(8):702-6.
Wedderkopp N, Thomsen K, Manniche C, et al. Jul. 9, 2009. No evidence for presence of bacteria in modic type I changes. Acta Radiol. 50(1):65-70.
Arndt J, Charles YP, Koebel C, et al. Oct. 2012. Bacteriology of degenerated lumbar intervertebral disks. J. Spinal Disord. Tech. 25(7):E211-6.
Bhanji S, Williams B, Sheller B, et al. Jul.-Aug. 2002. Transient bacteremia induced by toothbrushing a companson of the Sonicare toothbrush with a conventional toothbrush. Pediatr. Dent. 24(4):295-9.
Urquhart DM, Zheng Y, Cheng AC, et al. Jan. 22, 2015. Could low grade bacterial infection contribute to low back pain? A systematic review. BMC Med. 13(1):13.
Weiner BK, Vilendecic M, Ledic D, et al. 2015. Published online Dec. 28, 2014. Endplate changes following discectomy: natural history and associations between imaging and clinical data. Eur. Spine J. 24(11):2449-57.
Kerttula L, Luoma K, Vehmas T, et al. Jan. 17, 2012. Modic type I change may predict rapid progressive, deforming disc degeneration: a prospective 1-year follow-up study. Eur. Spine J. 21(6):1135-42.
Holm S, Baranto A, Kaigle Holm A, et al. 2007. Reactive changes in the adolescent porcine spine with disc degeneration due to endplate injury. Vet. Comp. Orthop. Traumatol. 20(1):12-7.
McDowell A, Valanne S, Ramage G, et al. Jan. 2005. Propionibacterium acnes types I and II represent phylogenetically distinct groups. J. Clin. Microbial. 43(1):326-34.
Nadkarni MA, Martin FE, Jacques NA, Hunter N. Jan. 2002. Determination of bacterial load by real-time PCR using a broad-range (universal) probe and primers set. Microbiology 148(1):257-266.
Mühl H, Kochem A-J, DisquéC, Sakka SG. Jan. 2010. Activity and DNA contamination of commercial polymerase chain reaction reagents for the universal 16S rDNA real-time polymerase chain reaction detection of bacterial pathogens in blood. Diagn. Microbial. Infect. Dis. 66(1):41-9.
Burke J, Watson R, McCormack D, et al. Feb. 21, 2003. Endplate changes are associated with increased disc inflammatory mediator production. J Bone Jt. Surg Br 85-B(Supp II): 164.
Klawitter M, Hakozaki M, Kobayashi H, et al. Jul. 5, 2014. Expression and regulation of toll-like receptors (TLRs) in human intervertebral disc cells. Eur. Spine J. 23(9):1878-91.
Quero L, Klawitter M, Schmaus A, et al. Aug. 22, 2013. Hyaluronic acid fragments enhance the inflammatory and catabolic response in human intervertebral disc cells through modulation of toll-like receptor 2 signaling pathways. Arthritis Res. Ther. 15(4):R94.
Ellman MB, Kim J-S, An HS, et al. Jun. 10, 2012. Toll-like receptor adaptor signaling molecule MyD88 on intervertebral disk homeostasis: In vitro, ex vivo studies. Gene 505(2):283-90.
Wang J, Tian Y, Phillips KLE, et al. Mar. 2013. Tumor necrosis factor α- and interleukin-1β-dependent induction of CCL3 expression by nucleus pulposus cells promotes macrophage migration through CCR1. Arthritis Rheum. 65(3):832-42.
Le Maitre CL, Hoyland JA, Freemont AJ. Aug. 9, 2007. Catabolic cytokine expression in degenerate and herniated human intervertebral discs: 1L-1β, and TNFα expression profile. Arthritis Res. Ther. 9(4):R77.
Burke JG, G Watson RW, Conhyea D, et al. Dec. 2003. Human nucleus pulposis can respond to a pro-inflammatory stimulus. Spine (Phila. Pa. 1976). 28(24):2685-93.
Li B, Dong Z, Wu Y, et al. Jul. 2016. Association between Lumbar Disc degeneration and Propionibacterium Acnes Infection: Clinical Research and Preliminary Exploration of Animal Experiment. Spine (Phila. Pa. 1976). [Epub ahead of print].

(56) References Cited

OTHER PUBLICATIONS

Ferguson SJ, Ito K, Nolte LP. Feb. 2004. Fluid flow and convective transport of solutes within the intervertebral disc. J. Biomech. 37(2):213-21.
Mirantes C, Passegue E, Pietras EM. Aug. 19, 2014. Pro-inflammatory cytokines: Emerging players regulating HSC function in normal and diseased hematopoiesis. Exp. Cell Res. :1-7.
Dudli S, Sing D, Burch S, et al. Mar. 2, 2016. Molecular and Cellular Changes in Vertebral Bone Marrow Lesions. In: Annual Meeting American Academy of Orthopaedic Surgeons. Orlando; Paper 454.
Dudli S, Haschtmann D, Ferguson SJ. 2012. Published online Oct. 24, 2011. Fracture of the vertebral endplates, but not equienergetic impact load, promotes disc degeneration in vitro. J. Orthop. Res. 30(5):809-16.
Torkki M, Majuri M-L, Wolff H, et al. Mar. 27, 2015. Osteoclast activators are elevated in intervertebral disks with Modic changes among patients operated for herniated nucleus pulposus. Eur. Spine J. [Epub ahead of print].
Perilli E, Parkinson IH, Truong L-H, et al. Jul. 26, 2014. Modic (endplate) changes in the lumbar spine: bone micro-architecture and remodelling. Eur. Spine J. 24(9):1926-34.
Mackiewicz Z, Salo J, Konttinen YT, et al. Mar.-Apr. 2009. Receptor activator of nuclear factor kappa B ligand in an experimental intervertebral disc degeneration. Clin. Exp. Rheumatol. 27(2):299-306.
Laasonen LS, Karvonen SL, Reunala TL. May 1994. Bone disease in adolescents with acne fulminans and severe cystic acne: radiologic and scintigraphic findings. AJR. Am. J. Roentgenol. 162(5):1161-1165.
Ziegler P, Boettcher S, Takizawa H, et al. 2016. Published online Nov. 11, 2015. LPS-stimulated human bone marrow stroma cells support myeloid cell development and progenitor cell maintenance. Ann. Hematol. 95(2): 173-8.
Wan Y, Chong L-W, Evans RM. Dec. 2007. PPAR-gamma regulates osteoclastogenesis in mice. Nat. Med. 13(12):1496-503.
Piccinini AM, Midwood KS. Jul. 2010. DAMPening inflammation by modulating TLR signalling. Mediators Inflamm. 2010.
Oegema TR, Johnson SL, Aguiar DJ, Ogilvie JW. Nov. 2000. Fibronectin and its fragments increase with degeneration in the human intervertebral disc. Spine (Phila. Pa. 1976). 25(21):2742-7.
Patel KB, Poplawski MM, Pawha PS, et al. Aug. 2014. Diffusion-weighted MRI "claw sign" improves differentiation of infectious from degenerative modic type 1 signal changes of the spine. AJNR. Am. J. Neuroradiol. 35(8):1647-52.
Di Martino A, Merlini L, Faldini C. Aug. 30, 2013. Autoimmunity in intervertebral disc herniation: from bench to bedside. Expert Opin. Ther. Targets 17(12):1461-70.
Ulrich JA, Liebenberg EC, Thuillier DU, et al. Dec. 2007. ISSLS prize winner: repeated disc injury causes persistent inflammation. Spine (Phila. Pa. 1976). 32, 2812-9.
Bendix T, Sorensen JS, Henriksson GAC, et al. Sep. 15, 2012. Lumbar modic changes-a comparison between findings at low- and high-field magnetic resonance imaging. Spine (Phila. Pa. 1976). 37, 1756-62.
McDowell A, Perry AL, Lambert PA, er al. Feb. 2008. A new phylogenetic group of Propionibacterium acnes. J. Med. Microbial. 57, 218-24.
Sharif, H. S. Role of MR imaging in the management of spinal infections. Jun. 1992. AJR Am J Roentgenol 158, 1333-1345.
Bertok L. Apr. 2005. Natural immunity, First Edit. Elsevier Science; 291 p.
Inagawa H, Kohchi C, Soma G-1. Jul. 2011. Oral administration of lipopolysaccharides for the prevention of various diseases: benefit and usefulness. Anticancer Res. 31(7):2431-6.
Chen Z, Zheng Y, Yuan Y, et al. (Jan. 26, 2016) Modic Changes and Disc Degeneration Caused by Inoculation of Propionibacterium acnes inside Intervertebral Discs of Rabbits: A Pilot Study. Biomed Res Int 2016:9612437.
Zuo, Assessment of Intervertebral Disc Degeneration With Magnetic Resonance Single-Voxel Spectroscopy, Magnetic Resonance in Medicine, 62: 1140-1146 (Sep. 24, 2009).
Freemont, A J., The cellular pathobiology of the degenerate intervertebral disc and discogenic back pain, (2009) Rheumatology; 48:5-10. (Advanced access publication Oct. 14, 2008).
Dudli, S. et al. "Propionibacterium acnes infected intervertebral discs cause vertebral bone marrow lesions consistent with Modic changes." J. Orthop. Res. Aug. 2016 34(8):1447-55.
International Search Report and Written Opinion dated Jul. 27, 2011 issued to international application No. PCT/US2010/052737.
International Search Report and Written Opinion dated Jul. 26, 2013 for international application No. PCT/US2013/036014.
International Search Report and Written Opinion dated Aug. 1, 2012 for PCT Application No. PCT/US2011/062137.
International Search Report and Written Opinion dated Sep. 25, 2014 for PCT Application No. PCT/US2014/022845.
International Search Report and Written Opinion dated Aug. 18, 2017 for PCT Application No. PCT/US2017/038034.

* cited by examiner

Using Pain='+' to be the positive level
Area Under Curve = 0.99121

MR SPECTROSCOPY SYSTEM AND METHOD FOR DIAGNOSING PAINFUL AND NON-PAINFUL INTERVERTEBRAL DISCS

CROSS-REFERENCE TO RELATED APPLICATIONS

This application is a continuation of U.S. patent application Ser. No. 15/185,597, filed Jun. 17, 2016, and titled "MR SPECTROSCOPY SYSTEM AND METHOD FOR DIAGNOSING PAINFUL AND NON-PAINFUL INTERVERTEBRAL DISCS," which is a continuation of U.S. patent application Ser. No. 14/310,721, filed Jun. 20, 2014, and titled "MR SPECTROSCOPY SYSTEM AND METHOD FOR DIAGNOSING PAINFUL AND NON-PAINFUL INTERVERTEBRAL DISCS," which is a continuation of U.S. patent application Ser. No. 12/579,371, filed Oct. 14, 2009, and titled "MR SPECTROSCOPY SYSTEM AND METHOD FOR DIAGNOSING PAINFUL AND NON-PAINFUL INTERVERTEBRAL DISCS." The entirety of each of the above-identified applications is hereby incorporated by reference and made a part of this specification for all that it discloses.

BACKGROUND

Field of the Disclosure

This disclosure relates to systems, processors, devices, and methods for measuring chemical constituents in tissue for diagnosing medical conditions. More specifically, it relates to systems, pulse sequences, signal and diagnostic processors, diagnostic displays, and related methods using novel application of nuclear magnetic resonance, including magnetic resonance spectroscopy, for diagnosing pain such as low back pain associated with degenerative disc disease.

Description of the Related Art

While significant effort has been directed toward improving treatments for discogenic back pain, relatively little has been done to improve the diagnosis of painful discs.

Magnetic resonance imaging (MRI) is the primary standard of diagnostic care for back pain. An estimated ten million MRIs are done each year for spine, which is the single largest category of all MRIs at an estimated 26% of all MRIs performed. MRI in the context of back pain is sensitive to changes in disc and endplate hydration and structural morphology, and often yields clinically relevant diagnoses such as in setting of spondlyolesthesis and disc herniations with nerve root impingement (e.g. sciatica). In particular context of axial back pain, MRI is principally useful for indicating degree of disc degeneration. However, degree disc degeneration has not been well correlated to pain. In one regard, people free of back pain often have disc degeneration profiles similar to those of people with chronic, severe axial back pain. In general, not all degenerative discs are painful, and not all painful discs are degenerative. Accordingly, the structural information provided by standard MRI exams of the lumbar spine is not generally useful for differentiating between painful and non-painful degenerative discs in the region as related to chronic, severe back pain.

Accordingly, a second line diagnostic exam called "provocative discography" (PD) is often performed after MRI exams in order to localize painful discs. This approach uses a needle injection of pressurized dye in awake patients in order to intentionally provoke pain. The patient's subjective reporting of pain level experienced during the injection, on increasing scale of 0-10, and concordancy to usual sensation of pain, is the primary diagnostic data used to determine diagnosis as a "positive discogram"—indicating painful disc—versus a "negative discogram" for a disc indicating it is not a source of the patient's chronic, severe back pain. This has significant limitations including invasiveness, pain, risks of disc damage, subjectivity, lack of standardization of technique. PD has been particularly challenged for high "false+" rates alleged in various studies, although recent developments in the technique and studies related thereto have alleged improved specificity of above 90%. (Wolfer et al., SPINE 2008) However, the significant patient morbidity of the needle-based invasive procedure is non-trivial, as the procedure itself causes severe pain and further compromises time from work. Furthermore, in another recent study PD was shown to cause significant adverse effects to long term disc health, including significantly accelerating disc degeneration and herniation rates (on the lateral side of needle puncture). (Carragee et al., SPINE 2009). Controversies around PD remain, and in many regards are only growing, despite the on-going prevalence of the invasive, painful, subjective, harmful approach as the secondary standard of care following MRI. PD is performed an estimated 400,000 times annually world-wide, at an estimated total economic cost that exceeds $750 Million Dollars annually. The need for a non-invasive, painless, objective, non-significant risk, more efficient and cost-effective test to locate painful intervertebral discs of chronic, severe low back pain patients is urgent and growing.

A non-invasive radiographic technique to accurately differentiate between discs that are painful and non-painful may offer significant guidance in directing treatments and developing an evidence-based approach to the care of patients with lumbar degenerative disc disease (DDD).

Previously reported lab experiments used 11T HR-MAS Spectroscopy to compare chemical signatures of different types of ex vivo disc nuclei removed at surgery. (Keshari et al., SPINE 2008) These studies demonstrated that certain chemicals in disc nuclei, e.g. lactic acid (LA) and proteoglycan (PG), may provide spectroscopically quantifiable metabolic markers for discogenic back pain. This is consistent with other studies that suggest DDD pain is associated with poor disc nutrition, anaerobic metabolism, lactic acid production (e.g. rising acidity), extracellular matrix degradation (e.g. reducing proteoglycan), and increased enervation in the painful disc nuclei. In many clinical contexts, ischemia and lowered pH cause pain, likely by provoking acid-sensing ion channels in nociceptor sensory neurons.

The previous disclosures evaluating surgically removed disc samples ex vivo with magnetic resonance spectroscopy (MRS) in a laboratory setting is quite encouraging for providing useful diagnostic tool based on MRS. However, an urgent need remains for a reliable system and approach for acquiring MRS signatures of the chemical composition of the intervertebral discs in vivo in a readily adoptable clinical environment, and to provide a useful, clinically relevant diagnostic tool based on these acquired MRS signatures for accurately diagnosing discogenic back pain. A significant need would be met by replacing PD with an alternative that, even if diagnostically equivalent, overcomes one or more of the significant shortcomings of the PD procedure by being non-invasive, objective, pain-free, risk-free, and/or more cost-effective.

SUMMARY

One aspect of the present disclosure is a MRS pulse sequence configured to generate and acquire a diagnostically useful MRS spectrum from a voxel located principally within an intervertebral disc of a patient.

According to one mode of this aspect, the pulse sequence is configured to generate and acquire the MRS spectrum from a single voxel principally located within the disc.

According to another mode of this aspect, the pulse sequence is configured to generate and acquire the MRS spectrum from the voxel located principally within a nucleus of the disc.

According to another mode of this aspect, the pulse sequence is configured to generate and acquire the MRS spectrum with sufficient signal-to-noise ratio (SNR) upon appropriate post-signal processing to perform at least one of: detect and measure at least one chemical constituent within the disc; and diagnose a medical condition based upon one or more identifiable signal features along the spectrum.

According to another mode, the pulse sequence is configured to generate and acquire the MRS spectrum from a single voxel principally located within a nucleus of the disc.

According to another mode, the pulse sequence is configured to generate and acquire the MRS spectrum from a voxel principally located within an intervertebral disc of the lumbar spine.

According to another mode, the pulse sequence is configured to generate and acquire at least one MRS spectrum from at least one voxel principally located within at least one of L3-L4, L4-L5, and L5-S1 intervertebral discs.

According to another mode, the pulse sequence is configured to generate and acquire multiple MRS spectra from multiple voxels, respectively, principally located within each of L3-L4, L4-L5, and L5-S1 intervertebral discs.

According to another mode, the pulse sequence is configured to generate and acquire multiple MRS spectra from multiple voxels, respectively, principally located within each of L3-L4, and L4-L5 intervertebral discs.

According to another mode, the pulse sequence is configured to generate and acquire the MRS spectrum from the voxel located principally within the L5-S1 intervertebral disc.

According to another mode, the pulse sequence is configured to generate and acquire the MRS spectrum via an NMR system of at least 1.5 tesla (T) field strength.

According to another mode, the pulse sequence is configured to generate and acquire the MRS spectrum via an NMR system of 1.5 tesla (T) field strength.

According to another mode, the pulse sequence is configured to generate and acquire the MRS spectrum via an NMR system of at least 3.0 tesla (T) field strength.

According to another mode, the pulse sequence is configured to generate and acquire the MRS spectrum via an NMR system of 3.0 tesla (T) field strength.

According to another mode, the pulse sequence comprises a chemical shift selective (CHESS) sequence.

According to another mode, the pulse sequence comprises a point resolved spectroscopy (PRESS) sequence.

According to another mode, the pulse sequence comprises a combination CHESS-PRESS sequence.

According to another mode, the pulse sequence comprises at least one control variable (CV) parameter setting as disclosed in Table 1.

According to another mode, the pulse sequence comprises all the control variable (CV) parameter settings disclosed in Table 1.

According to another mode, the pulse sequence comprises an echo time (TE) of about 28 milliseconds.

According to another mode, the pulse sequence comprises a repetition time (TR) of about 1000 milliseconds (1 second).

According to another mode, the pulse sequence comprises an acquisition matrix size setting of about 1 in each dimension, with a number of spatial slices setting of 1.

According to another mode, the pulse sequence comprises at least one of the following CHESS flip angles: about 105 (angle 1); about 80 (angle 2); about 125 (angle 3).

According to another mode, the pulse sequence comprises at least one of the following PRESS correction settings: about 1.2 for each of X, Y, and Z axes.

According to another mode, the pulse sequence comprises at least one of the following PRESS flip angles: about 90 (angle 1); about 167 (angle 2); about 167 (angle 3).

According to another mode, the pulse sequence is configured to generate and acquire a repetitive frame MRS acquisition series from the voxel with signal-to-noise ratio (SNR) in the water region along the spectrum of multiple said frames that is sufficiently high to be identified, yet sufficiently low to provide adequate dynamic range with sufficient signal-to-noise ratio (SNR) along other chemical regions of diagnostic interest along the spectral frames to allow the other regions to be identified and evaluated, post-signal processing and post-averaging of the frames, for diagnostic use.

Another aspect of the present disclosure is an MRS signal processor that is configured to select a sub-set of multiple channel acquisitions received contemporaneously at multiple parallel acquisition channels, respectively, of a multi-channel detector assembly during a repetitive-frame MRS pulse sequence series conducted on a region of interest within a body of a subject.

According to one mode of this aspect, the MRS signal processor is configured to select a sub-set of multiple channel acquisitions received contemporaneously at multiple parallel acquisition channels, respectively, of a multi-channel detector assembly during the repetitive-frame MRS pulse sequence series conducted on a voxel principally located within an intervertebral disc within the body of the subject.

According to one mode of this aspect, the MRS signal processor is configured to automatically differentiate relatively stronger from weaker channel acquisitions received.

According to another mode of this aspect, the MRS signal processor is configured to determine and select a strongest single channel acquisition signal among the multiple channel acquisitions.

According to one embodiment of this mode, the MRS signal processor is configured to determine and select the strongest single channel acquisition based upon a highest measured parameter of the single channel acquisition spectral series comprising at least one of amplitude, power, or signal-to-noise ratio (SNR) of water signal in the spectrum in the selected channel relative to the other channel.

According to one variation of this embodiment, the selection is based upon the frame averaged spectrum of the series acquired from the channel.

According to another variation of this embodiment, the MRS signal processor is configured to determine and select a sub-set of strongest channels based upon a range threshold based from the highest measured parameter of the strongest single channel.

According to another embodiment, the MRS signal processor is configured to determine and select one or more "strongest" channels among the series based upon a threshold criteria for a feature of the channel acquisition data.

Another aspect of the present disclosure is an MRS signal processor comprising a phase shift corrector configured to recognize and correct phase shifting within a repetitive multi-frame acquisition series acquired by a multi-channel detector assembly during an MRS pulse sequence series conducted on a region of interest within a body of a subject.

According to one mode of this aspect, the phase shift corrector is configured to recognize and correct the phase shifting within a repetitive multi-frame acquisition series acquired by a multi-channel detector assembly during an MRS pulse sequence series conducted on a voxel within an intervertebral disc in the body of the patient.

According to another mode, the phase shift corrector is configured to recognize and correct the phase shifting in the time domain.

Another aspect of the present disclosure is a MRS signal processor comprising a frequency shift corrector configured to recognize and correct frequency shifting between multiple acquisition frames of a repetitive multi-frame acquisition series acquired within an acquisition detector channel of a multi-channel detector assembly during a MRS pulse sequence series conducted on a region of interest within a body of a subject.

According to one mode of this aspect, the frequency shift corrector is configured to recognize and correct frequency shifting between multiple acquisition frames of a repetitive multi-frame acquisition series acquired within an acquisition detector channel of a multi-channel detector assembly during a MRS pulse sequence series conducted on a voxel within an intervertebral disc in the body of the subject.

According to another mode, the frequency shift corrector is configured to recognize and correct the frequency shifting in the time domain.

According to another mode, the frequency shift corrector is configured to recognize and correct the frequency shifting in the frequency domain.

According to one embodiment of this mode, the frequency shift corrector is configured to identify and locate a water peak in each of multiple acquisition frames of the series, compare the location of the located water peaks against a reference baseline location to determine a separation shift therebetween for each frame, and to correct the shift to align the location to the baseline location by applying an appropriate offset to all the spectral data of each frame.

According to one variation of this embodiment, the location of the water peak is estimated based upon a location range where the water signal exceeds a threshold amplitude value.

Another aspect of the present disclosure is a MRS signal processor comprising a frame editor configured to recognize at least one poor quality acquisition frame, as determined against at least one threshold criterion, within an acquisition channel of a repetitive multi-frame acquisition series received from a multi-channel detector assembly during a MRS pulse sequence series conducted on a region of interest within a body of a subject.

According to one mode of this aspect, the frame editor is configured to edit out the poor quality frame from the series.

According to another mode, the frame editor is configured to recognize the poor quality acquisition frame based upon a threshold value applied to error in peak location of recognized water signal from an assigned baseline location.

According to another mode, the frame editor is configured to recognize the poor quality acquisition frame based upon a threshold confidence interval applied to the ability to recognize the peak location of water signal in the frame spectrum.

Another aspect of the present disclosure is an MRS signal processor that comprises an apodizer configured to apodize an MRS spectrum otherwise generated and acquired by via an MRS aspect otherwise herein disclosed, and/or signal processed by one or more of the various MRS signal processor aspects also otherwise herein disclosed.

Another aspect of the present disclosure is an MRS diagnostic processor configured to process information extracted from an MRS spectrum for a region of interest in a body of a subject, and to provide the processed information in a manner that is useful for diagnosing a medical condition associated with the region of interest.

According to one mode of this aspect, the MRS diagnostic processor is configured to process the extracted information from the MRS spectrum for a voxel principally located in an intervertebral disc of the subject, and to provide the processed information in a manner that is useful for diagnosing a medical condition associated with the intervertebral disc.

According to one embodiment of this mode, the MRS diagnostic processor is configured to process the extracted information from the MRS spectrum for a voxel principally located in a nucleus of the intervertebral disc, and to provide the processed information in a manner that is useful for diagnosing a medical condition associated with the intervertebral disc.

According to another embodiment, the MRS diagnostic processor is configured to provide the processed information in a manner that is useful for diagnosing the intervertebral disc as painful.

According to another embodiment, the MRS diagnostic processor is configured to provide the processed information in a manner that is useful for diagnosing the intervertebral disc as severely painful.

According to another embodiment, the MRS diagnostic processor is configured to provide the processed information in a manner that is useful for diagnosing the intervertebral disc as not severely painful.

According to another embodiment, the MRS diagnostic processor is configured to provide the processed information in a manner that is useful for diagnosing the intervertebral disc as substantially non-painful.

According to another embodiment, the MRS diagnostic processor is configured to diagnose the disc as painful.

According to another embodiment, the MRS diagnostic processor is configured to diagnose the disc as severely painful.

According to another embodiment, the MRS diagnostic processor is configured to diagnose the disc as not severely painful.

According to another embodiment, the MRS diagnostic processor is configured to diagnose the disc as substantially non-painful.

According to another embodiment, the MRS diagnostic processor is configured diagnose the disc as not severely painful.

According to another embodiment, the MRS diagnostic processor is configured to assign a value for the disc that is referenced against a range for use in determining presence, absence, or level of pain.

According to another embodiment, the MRS diagnostic processor is configured to provide the diagnostically useful information in a display overlay onto an MRI image.

According to one variation of this embodiment, the display overlay associates the diagnostically useful information with one or more intervertebral discs evaluated.

According to another variation, the display overlay comprises a scaled legend of values along a range, and an indicator of a result referenced against the range in the legend and associated with an intervertebral disc evaluated.

According to another variation, the display overlay comprises both color coding and numerical coding of results in a legend and for at least one indicator of processed information associated with at least one intervertebral disc evaluated by the diagnostic processor.

According to another embodiment, the diagnostic processor comprises a diagnostic algorithm empirically created by comparing acquired and processed MRS spectra for multiple intervertebral discs against control measures for pain, and that is configured to determine whether discs evaluated with the MRS spectra are painful or non-painful.

According to one variation, the diagnostic algorithm comprises at least one factor related to spectral information extracted from MRS spectral regions associated with at least one of proteoglycan, lactate, and alanine chemicals.

According to one feature of this variation, the extracted information related to at least one said region is divided by voxel volume.

According to another feature of this variation, the extracted information related to at least one said region comprises a peak value in the region.

According to another feature of this variation, the extracted information related to at least one said region comprises a power value in the region.

According to another applicable feature, the diagnostic algorithm comprises at least two factors related to spectral information extracted from the MRS spectral regions associated with at least two of said chemicals.

According to another applicable feature, the diagnostic algorithm comprises three factors related to spectral information extracted from the MRS spectral regions associated with all three of said chemicals.

According to another applicable feature, the diagnostic algorithm comprises at least two said factors related to spectral information extracted from the MRS spectral regions associated with all three of said chemicals.

According to still another applicable feature, at least one said factor is weighted by a constant.

According to another applicable feature, at least one said factor comprises a ratio of at least two values associated with information extracted from the MRS spectra at regions associated with at least two of proteoglycan, lactate, and alanine chemicals.

According to still a further variation, the algorithm comprises four factors associated with MRS spectral data associated with proteoglycan region, lactate region, proteoglycan:lactate region ratio, and proteoglycan:alanine region ratio.

According to one applicable feature of this variation, the algorithm comprises four factors associated with MRS spectral data associated with proteoglycan region divided by voxel volume, lactate region divided by voxel volume, proteoglycan:lactate region ratio, and proteoglycan:alanine region ratio.

According to still another applicable feature, the four factors are weighted by constants.

According to still a further variation, the algorithm is configured to calculate a diagnostically useful value as follows:

$$\text{Value} = -[\log(PG/LA*(0.6390061) + PG/AL*(1.45108778) + PG/\text{vol}*(1.34213514) + LA/\text{VOL}*(-0.5945179) - 2.8750366)];$$

wherein PG=peak measurement in proteoglycan spectral region, AL=peak measurement in alanine region, LA=peak measurement in LA region, and vol=volume of prescribed voxel in disc used for MRS data acquisition.

According to still a further applicable feature, the calculated diagnostically useful value is compared against a threshold value of zero (0) to determine pain diagnosis.

According to still a further applicable feature, positive calculated values are considered painful and negative calculated values are considered non-painful diagnoses.

According to another variation, the diagnostic algorithm is based at least in part upon a feature associated with a combined spectral region associated with lactate and alanine chemicals.

According to another variation, the diagnostic algorithm is based at least in part upon a power measurement taken along an MRS spectral region that combines regions associated with lactate and alanine chemicals.

Another aspect of the present disclosure is an MRS system comprising an MRS pulse sequence, MRS signal processor, and MRS diagnostic processor, and which is configured to generate, acquire, and process an MRS spectrum for providing diagnostically useful information associated with a region of interest in a body of a patient.

According to one mode of this aspect, the MRS system comprising the MRS pulse sequence, MRS signal processor, and MRS diagnostic processor, is configured to generate, acquire, and process the MRS spectrum for a voxel principally located in an intervertebral disc in the body of the patient and to provide diagnostically useful information associated with the disc.

According to one embodiment of this mode, the voxel is principally located in a nucleus of the disc.

According to another embodiment of this mode, the diagnostically useful information is useful for diagnosing pain or absence of pain associated with the disc.

Various further modes of this aspect are contemplated that comprise one or more of the various aspects, modes, embodiments, variations, and features of the MRS pulse sequence, MRS signal processor, and MRS diagnostic processor as described above.

According to one such further mode, the MRS pulse sequence comprises a combination CHESS-PRESS sequence.

According to another such further mode, the MRS pulse sequence comprises a TE of about 28 ms and a TR of about 1000 ms.

According to another such further mode, the MRS signal processor comprises at least one of a channel selector, a phase shift corrector, a frequency shift corrector, and a frame editor.

According to another such further mode, the MRS diagnostic processor is configured to calculate and provide diagnostically useful information for diagnosing pain associated with at least one intervertebral disc based upon at least one MRS spectral region associated with at least one of proteoglycan, lactate, and alanine chemicals.

According to another mode of the various aspects above, each or all of the respective MRS system components described is provided as user or controller operable software in a computer readable storage medium configured to be installed and operated by a processor.

According to one embodiment of this mode, a computer operable storage medium is provided and stores the operable software.

Still further aspects of the present disclosure comprise various MRS method aspects associated with the other MRS system, sequence, and processor aspects described above.

Each of the foregoing aspects, modes, embodiments, variations, and features noted above is considered to represent independent value for beneficial use, whereas their various combinations and sub-combinations as may be made by one of ordinary skill based upon a thorough review of this disclosure in its entirety are further contemplated aspects also of independent value for beneficial use.

BRIEF DESCRIPTION OF THE DRAWINGS

These and other features, aspects, and advantages of the present disclosure will now be described with reference to the drawings of embodiments, which embodiments are intended to illustrate and not to limit the disclosure.

DETAILED DESCRIPTION

Figure 1A:
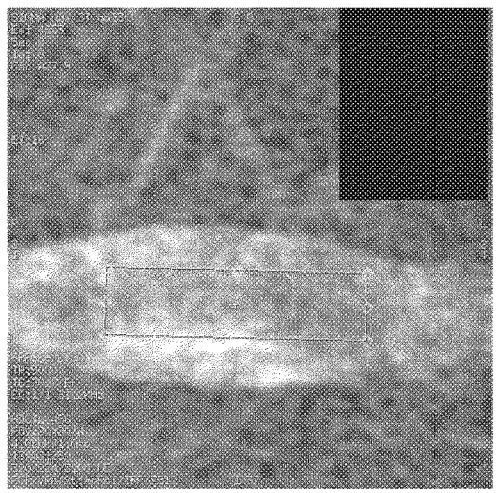
FIGS. 1A-C illustrate an example of a voxel prescription within a disc for performing a DDD-MRS exam according to one aspect of the disclosure, in coronal, sagittal, and axial imaging planes, respectively.

Certain aspects of the current disclosure relate to new & improved system approaches, techniques, processors, & methods for conducting clinical magnetic resonance spectroscopy (MRS) on human intervertebral discs, in particular according to a highly beneficial mode of this disclosure for using acquired MRS information to diagnose painful and/or non-painful discs associated with chronic, severe axial lumbar (or "low") back pain associated with degenerated disc disease (or "DDD pain"). For purpose of clarity in this disclosure, the current aspects, modes, embodiments, variations, and features disclosed with particular benefits for this purposed are generally assigned the label "DDD-MRS."

Various aspects of this disclosure relate to highly beneficial advances in three aspects useful in particular for conducting a DDD-MRS exam: (1) MRS sequence for generating & acquiring robust MRS spectra; (2) signal processor configured to improve signal-to-noise ratio (SNR) of the acquired MRS spectra; and (3) diagnostic processor configured to use information from the acquired & processed MRS spectra for diagnosing painful and/or non-painful discs on which the MRS exam is conducted in a DDD pain patient.

Several configurations & techniques related to the DDD-MRS pulse sequence & signal processor have been created, developed, and evaluated for conducting 3T MRS on human intervertebral discs for diagnosing DDD pain. A novel "DDD" MRS pulse sequence was developed & evaluated for this purpose, and with certain parameters specifically configured to allow robust application of the signal processor for optimal processed final signals in a cooperative relationship between the pulse sequence & post-signal processing conducted. These approaches can be used, with a 3 Tesla (3T) "Signa" MR system commercially available from General Electric (GE). Highly beneficial results have been observed using the current disclosed application technologies on this MR platform, which alone is considered to propose significant benefit to pain management in the patients requiring diagnosis. However, the current disclosure contemplates these aspects broadly applicable according to one of ordinary skill to a variety of MR platforms commercially available or that may be developed by various different manufacturers.

In conducting the DDD-MRS sequence, a single three dimensional "voxel" is prescribed by an operator at a control consul, using 3 imaging planes (mid-sagittal, coronal, axial) to define the "region of interest" (ROI) in the patient's body for MR excitation by the magnet & data acquisition by the acquisition channel/coils designated for the lumbar spine exam within the spine detector coil assembly. The DDD-MRS pulse sequence pulses an applied & released magnetic field to the ROI, which causes unique bonds of various chemicals within the ROI to resonate at different "signature resonant frequencies" across a range. The amplitudes of frequencies at various locations along this range are plotted along a curve as the MRS "spectrum" for the ROI. This is done iteratively across multiple acquisitions for a given ROI, typically representing over 100 acquisitions, and often between about 200 and about 600 acquisitions, such as between 300 and 400 acquisitions for a given exam of a ROI. One acquisition spectrum among these iterations is called a "frame" for purpose of this disclosure. These multiple acquisitions are conducted in order to average their respective acquired spectra/frames to reduce the amplitudes of acquired signal components representing noise (typically more random or "incoherent" & thus reduced by averaging) while better maintaining the amplitudes of signal components representing resonant chemical frequencies in the ROI (typically repeatable and "coherent" and thus not reduced by averaging). By reducing noise while maintaining true target signal, this process is thus conducted for the primary objective to increase SNR. These acquisitions are also conducted at various acquisition channels selected at the detector coils, generally 6 channels corresponding with the lumbar spine area. The 3T MRI Signa (GE) system, in standard operation conducting one beneficial mode of DDD-MRS sequence evaluated, is configured to average all acquired frames across all acquisition channels to produce a single averaged MRS curve for the ROI.

This unmodified approach has been observed to provide a relatively low signal/noise ratio, with low confidence in many results regarding data extraction at spectral regions of interest, such as for example and in particular regions associated with proteoglycan or "PG" (n-acetyl) and lactate or lactic acid (LA). Sources of potential error and noise inherent in this imbedded signal acquisition & processing configuration of the 3T Signa, as operated under the sequence used, were observed. These various sources of potential error or signal-to-noise ratio (SNR) compromise were determined to be correctable—either by altering certain structures or protocols of coil, sequence, or data acquisition, or in post-processing of otherwise standard protocols and structures used. Among these approaches, various post-processing approaches were developed & observed to produce significantly improved & highly favorable results using otherwise un-modified GE Signa operation pre-processing. In particular, various improvements developed and applied under the current post-signal processor disclosed hereunder have been observed to significantly improve signal quality and SNR.

The improvements advanced under the post-signal processor configurations disclosed hereunder include embodiments related to the following: (1) acquisition channel selection; (2) Phase correction; (3) Frequency correction; (4) Frame editing and (5) Apodization. While any one of these is considered highly beneficial, their combination has been observed to provide significantly advantageous results. Various examples are provided to illustrate sources of error or "noise" observed, and corrections employed to improve signal quality. Strong signals typically associated with normal healthy discs were evaluated first to assess the signal processing approach. Signals from the Signa that were considered more "challenged" for robust data processing & diagnostic use were evaluated for further development to evaluate if more robust metabolite signal can be elicited from otherwise originally poor SNR signals from the Signa.

Defining the Voxel (Voxel Prescription)

The current embodiment of this disclosure relates principally to "single voxel" MRS, where a single three dimensional region of interest (ROI) is defined as a "voxel" for MRS excitation & data acquisition. The spectroscopic voxel is selected based on T2-weighted high-resolution spine images acquired in the sagittal, coronal and axial planes. The patient is placed into the scanner in a supine position, head first. The axial spine images acquired are in the oblique plane in order to better encompass the disc of interest. This voxel is prescribed within a disc nucleus for purpose of using acquired MRS spectral data to diagnose DDD pain, according to the present preferred embodiments. Typical voxel dimensions (Z-axis, X-axis, Y-axis) are 5 mm (thick) by 14 mm (width) by 16 mm (length), though may vary any or all of these dimensions by operator prescription to suit a particular anatomy. In general for DDD-MRS application evaluating disc nucleus chemical constituents, the objective for voxel prescription is to capture as much of the nuclear volume as possible (e.g. maximizing magnitude of relevant chemical signals acquired), while restricting the voxel borders from capturing therewithin structures of the outer annulus or bordering vertebral body end-plates (where lipid contribution may be captured and may shroud chemical spectral regions of interest such as lactate or alanine, as further developed elsewhere hereunder. In fact, the actual operation may not exactly coincide with acquiring signal from only within the voxel, and may include some bordering region contribution. This some degree of spacing between the borders and these structures is often desired. These objectives may be more difficult to achieve for some disc anatomies than others, e.g. L5-S1 may be particularly challenging as frequently highly angulated, irregularly shaped, and collapsed as to disc height.

Accordingly, an initial prescription may not be appropriate, though may not be known until the sequence is begun. Accordingly, further aspects of the present disclosure contemplate a voxel prescription protocol which prescribes a first prescription, monitors results (either during scan or after completion), and if a lipid signature or other suspected signal degradation from expected results is observed, re-prescribe the voxel to avoid suspected source of contaminant (e.g. make the voxel smaller or adjust its dimensions, tilt, or location) and re-run an additional DDD-MRS acquisition series (retaining the signal considered more robust and with least suspected signal degradation suspected to be voxel error). According to still a further mode, a pre-set protocol for re-prescribing in such circumstances may define when to accept the result vs. continue re-trying. In one exemplary embodiment, the voxel may be re-prescribed and acquisition series re-run once, or perhaps twice, and then the best result is to be accepted. It is to be appreciated, as with many technology platforms, that operator training and techniques in performing such user-dependent operations may be relevant to results, and optimal (or conversely sub-optimal) results may track skill levels and techniques used.

Figure 1B:
Figure 1C:

In most voxel prescriptions, the thickness is limited by the scanner's ability to generate the magnetic gradient that defines the Z-axis (axial plane) dimension. For example, a minimum thickness limit is pre-set to 4 mm on the GE Signa 3T. While such pre-set limits of interfacing, cooperative equipment & related software certainly result in limits on the current application's ability to function in that environment outside of these limits, the broad aspects of the current disclosure should not be considered so limited, and functionality may flourish within other operating ranges in cases where such other imparted limitations may be released. An example of a single voxel prescription according to the three images is shown in FIGS. 1A-1C as follows. FIG. 1A shows a coronal view oriented aspect of the voxel prescription. FIG. 1B shows a sagittal view oriented aspect of the voxel prescription. FIG. 1C shows an axial view oriented aspect of the voxel prescription.

The "DDD" MRS Pulse Sequence

The DDD-MRS pulse sequence shares certain similarities, though with some significant modifications defined hereunder, with another pulse sequence called "PROSE". PROSE is primarily intended for use for diagnosing prostate cancer, and is approved for use and sale and available from GE. The DDD-MRS pulse sequence of the present embodiments, and PROSE for further reference, employ a sequence approach called Point RESolved Spectroscopy. This involves a double spin echo sequence that uses a 90° excitation pulse with two slice selective refocusing radio frequency (RF) pulses, combined with 3D chemical shift imaging (CSI) phase encoding gradients to generate 3-D arrays of spectral data or chemical shift images. Due to the small size, irregular shape, and the high magnetic susceptibility present when doing disc spectroscopy for DDD pain, the 3D phase encoding option available under PROSE is not an approach typically to be utilized under the current disclosed version of DDD-MRS sequence, and single voxel spectra are acquired by this version of DDD-MRS. This can be accomplished by setting the user control variables (CVs) for the matrix acquisition size of each axis to 1 (e.g., in the event the option for other setting is made available). Further aspects of pulse sequence approaches contemplated are disclosed elsewhere hereunder.

Coil and Patient Positioning

Figure 2:
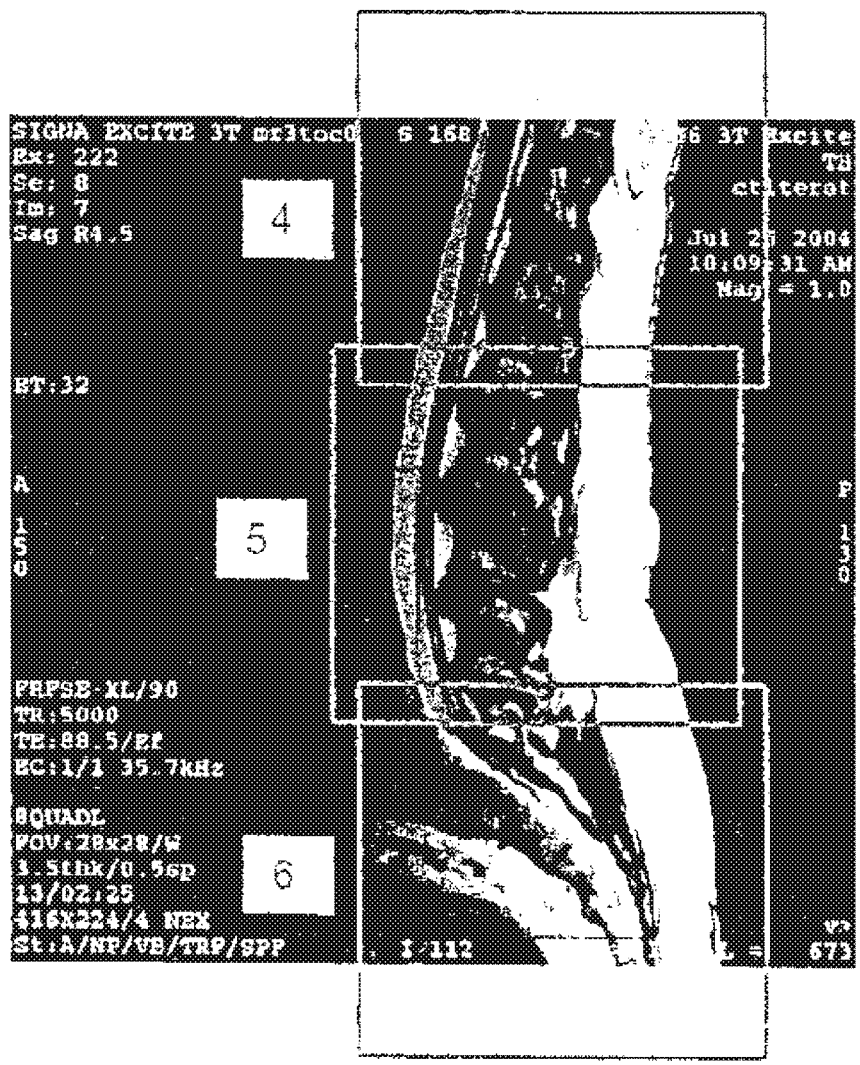
FIG. 2 shows an example of the sectional deployment in a GE phased array spine coil with which certain aspects of the present disclosure are configured to interface for cooperative operation and use.

The primary source of MRS signals obtained from a Signa 3T scanner, according to the physical embodiments developed & evaluated hereunder this disclosure, are from the GE HDCTL 456 Spine Coil. This is a "receive-only" coil with twelve coils configured into six sections (FIG. 2). Each section contains a loop and saddle coil. For lumbar (and thoracic) coverage, such as associated with lumbar DDD pain diagnosis, sections 4, 5, and 6 are deployed to provide six individual channel signals.

Water and Lipid Signal Suppression

Figure 5:
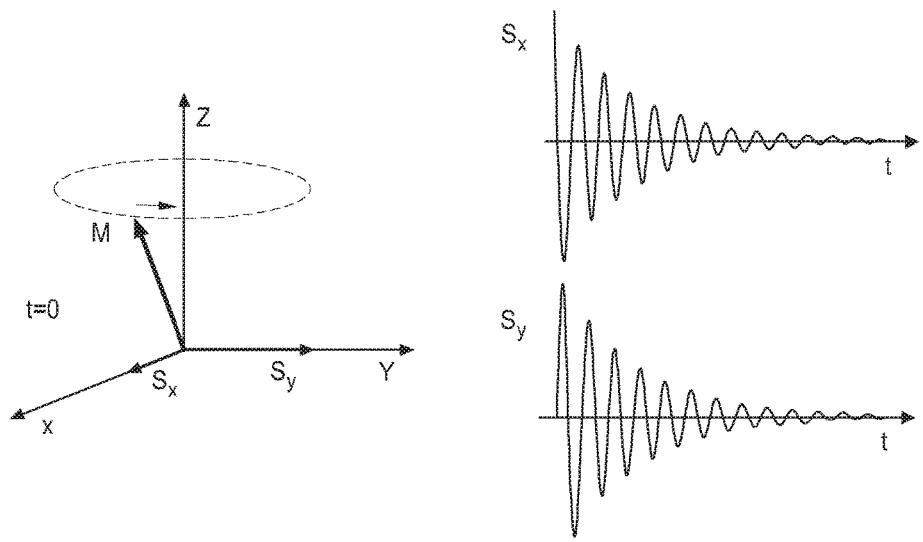
FIG. 5 shows Real (Sx) and imaginary (Sy) parts of an FID (right) that correspond to x and y components of the rotating magnetic moment M (left).
Figure 6:
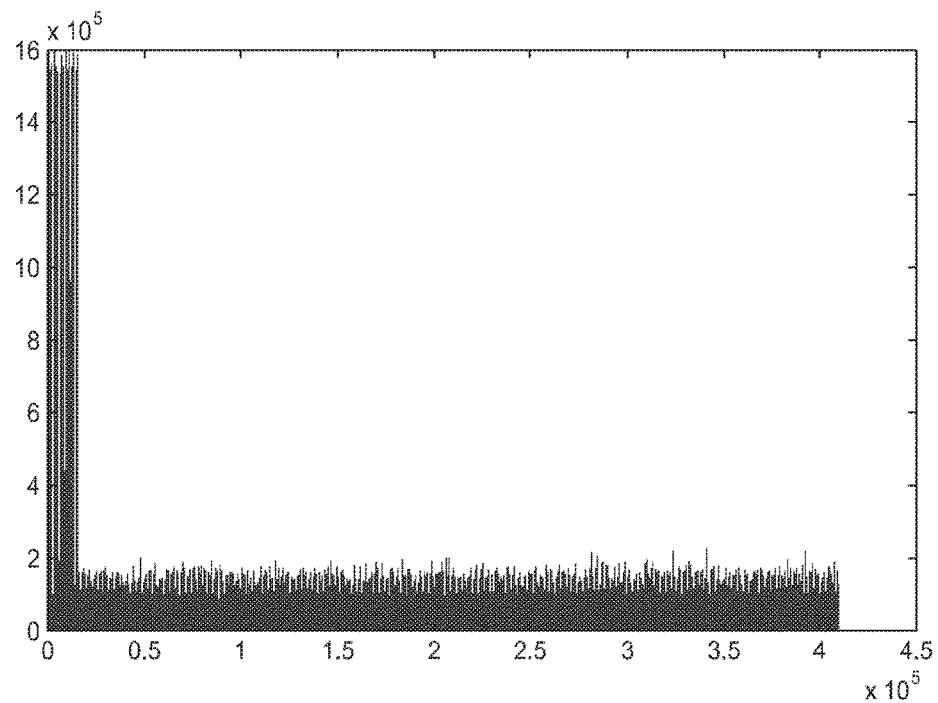
FIG. 6 shows an amplitude plot of complex data from a standard MRS series acquisition of multiple frame repetitions typically acquired according to certain present embodiments, and shows amplitude of signal on the y-axis and time on the x-axis.

In another sequence called "PROBE" commercially available by GE, and which is a CSI sequence used for brain spectroscopy, the lipid/fat signals are resolved through the use of long TE (144 ms) periods and 2 dimensional transformations (2DJ). These acquisition and signal processing techniques are facilitated by the large voxel volumes prescribed in the brain as well as the homogeneity of the brain tissue resulting in narrow spectral line widths. In the prostate region targeted by PROSE, however, the voxel prescriptions are much smaller and it is often impossible to place the voxel so as to exclude tissues that contain lipid/fat. Therefore, two robust water and lipid suppression approaches are available and used, if warranted, in the PROSE sequence: "BASING" and "SSRF" (Spectral Spatial Radio Frequency). An even more challenging environment of bordering lipid and reduced homogeneity has been observed with the current DDD pain application where the current ROI within disc nuclei are closely bordered by vertebral bodies with bone marrow rich in lipid content. However, due both to the desire to use short TE times (e.g. 28 ms) for the current DDD pain application in lumbar spine, and the desire to observe MRS signatures of other chemicals within disc nuclei that may overlap with lipid signal contribution along the relevant DDD-MRS spectrum, these water/lipid suppression approaches as developed for brain and prostate application are not necessarily optimized for DDD-MRS application in many circumstances. While a SSRF suppression approach for lipid resonances may be employed in the DDD-MRS sequence, the narrow band RF pulse required for this may require a long RF period and amplitude that will exceed the SAR level for the imager. Water suppression is provided by a CHESS sequence interleaved or otherwise combined in some manner with the PRESS sequence in order to provide appropriate results. Optimization of the residual water spectral line for frequency correction is done, according to on hightly beneficial further aspect, with the setting prescribed for the third flip angle. The angle is lowered to reduce the water suppression function which increases the residual water spectral line amplitude. A particular flip angle for this purpose may be for example about 125, though may be according to other examples between about 125 degrees and about 45 degrees. This flip angle is another example where some degree of customization may be required, in order to optimize water signal for a given disc. As some discs may be more dehydrated or conversely more hydrated than others, the water suppression may be more appropriate at one level for one disc, and at another level for another disc. This may require some iterative setting & acquisition protocol to optimize, whereas the exemplary angle described hereunder is considered appropriate for most circumstances and may be a pre-defined starting place for "first try." For further clarity and understanding of the present embodiments, FIG. 5 shows an example of a CHESS water suppression pulse sequence diagram, whereas FIG. 6 shows an example of a combined CHESS-PRESS pulse sequence diagram.

Outer Voxel Suppression

Another feature that is hereunder contemplated according to a further mode of the DDD-MRS sequence is the use of very selective saturation (VSS) pulses for removal of signal contamination that may arise from chemical shift error within the voxel as well as outside the selected ROI or voxel in the disc nuclei. In the default operating mode of one DDD-MRS sequence approach sharing some similarities with PROSE, for example, multiple pairs of VSS RF suppression bands are placed symmetrically around the prescribed DDD-MRS voxel. The DDD-MRS sequence according to this mode uses the VSS bands to define the DDD-MRS volume. It is believed that up to six additional VSS bands may be prescribed (each consisting of three VSS RF pulses) graphically in PROSE, with the goal of reducing the chemical shift error that can occur within the voxel as well as suppress excitation of out of voxel tissue during the PRESS localization of the voxel. According to some observations in applying DDD-MRS to disc spectroscopy, these additional graphic VSS pulses were found to not significantly improve the volume selection. Accordingly, while they may provide benefit in certain circumstances, they also may not be necessary or even desired to be used in others.

Figure 33A:
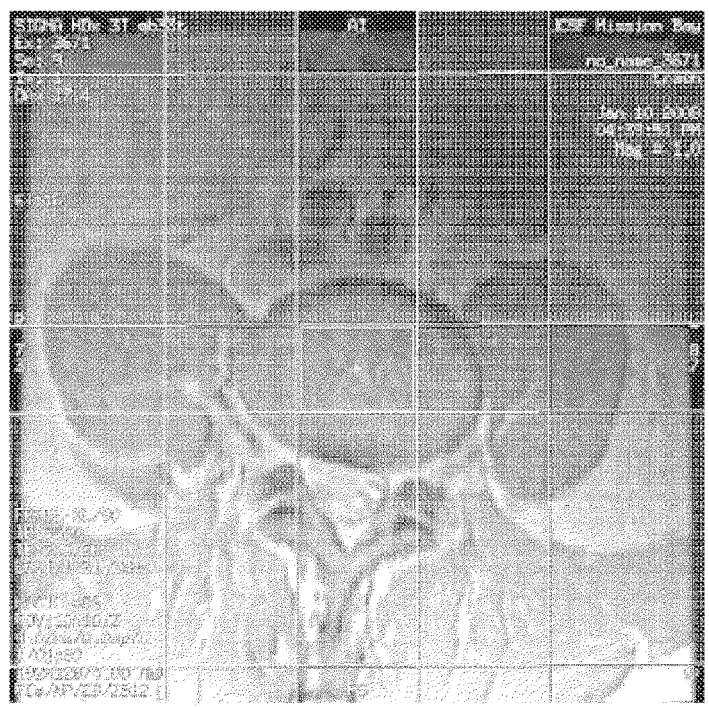
FIGS. 33A-C show three respective planar views of a very selective saturation (VSS) prescription for a voxelated acquisition series conducted via an MRS pulse sequence according to further aspects hereunder.
Figure 33B:
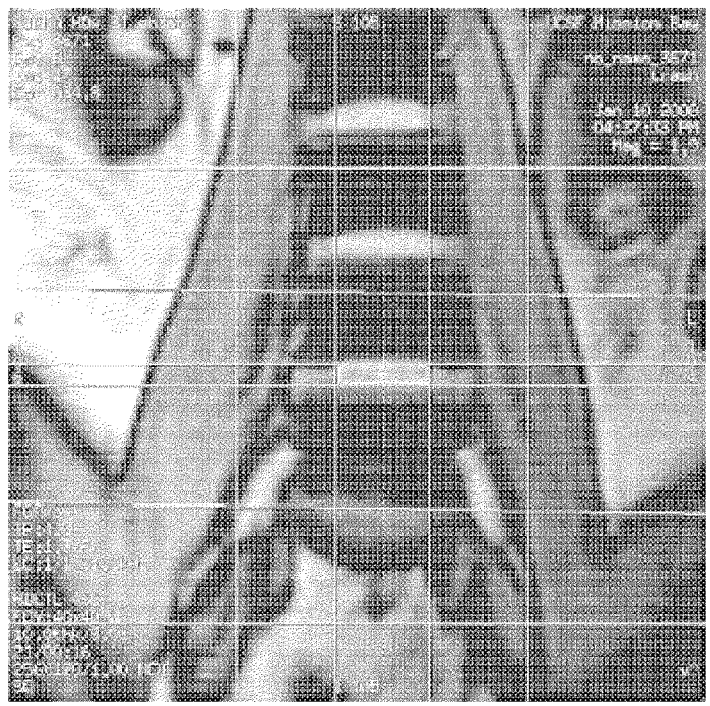
Figure 33C:
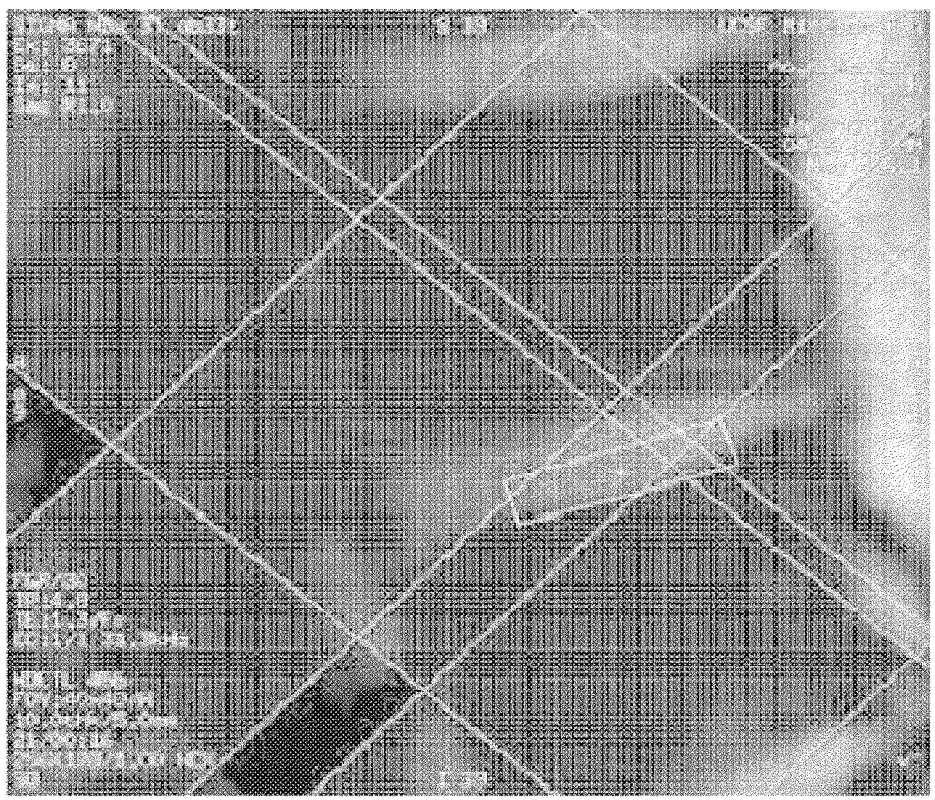

As shown in FIGS. 33A-C, multiple VSS bands are placed around the voxel prescription in each plane to reduce out of voxel excitation and chemical shift error present during the PRES localization of the voxel.

PRESS Timing Parameters

For purpose of comparative reference, the echo time (TE) of about 130 ms is believed to be the default selection typically used for PROSE data acquisitions. This echo time is typically considered too long for disc spectra due to the shorter $T_2$ relaxation times of the chemical constituents of lumbar intervertebral discs, leading to a dramatic decrease in signal to noise in long echo PRESS spectra. Therefore a shorter echo time setting for the scanner, such as for example 28 milliseconds, is generally considered more appropriate & beneficial for use in the current DDD-MRS sequence & DDD pain application. A frame repetition time (TR) of for example about 1000 ms provides sufficient relaxation of the magnetic dipoles in the ROI and leads to reasonable acquisition times and is believed to represent a beneficial compromise between short acquisition times and signal saturation at shorter values of TR. Other appropriately applicable timing values for PRESS spectra applicable to the DDD-MRS sequence may be, for example: number of data points equal to about 1024, number of repetitions equal to about 300, and typical voxel size of $4 \times 18 \times 16$ mm$^3$. First, second, and third flip angles of PRESS for the current exemplary DDD-MRS sequence embodiment may be for example 90, 167, and 167, respectively.

Summary of Exemplary User Control Variables (CV) for DDD-MRS Sequence

The foregoing disclosure describes various user controllable sequence settings observed to be appropriate and of particular benefit for use in an exemplary DDD-MRS sequence according to the current disclosure and for use for diagnosing DDD pain, as contemplated under the preferred embodiments hereunder. These are further summarized in Table 1 below.

TABLE 1

Exemplary CV Variables for DDD-MRS sequence for generating MRS spectra useful for post-processing & diagnosing DDD pain

| CV Variable | Value |
|---|---|
| TE (usec) | 28000 |
| TR (usec) | 1000000 |
| Acquisition Matrix Size | 1 |
| Acquisition Matrix Size | 1 |
| Number of spatial slices | 1 |
| Water Suppression Method | 1 |
| CHESS Flip Angle 1 | 1050 |
| CHESS Flip Angle 2 | 800 |
| CHESS Flip Angle 3 | 125 |
| VSS Band Configuration | 7 |
| PRESS Correction –X axis | 1.2 |
| PRESS Correction –Y axis | 1.2 |
| PRESS Correction –Z axis | 1.2 |
| Number of Frames | 300 |
| PRESS Flip Angle 1 | 90 |
| PRESS Flip Angle 2 | 167 |
| PRESS Flip Angle 3 | 167 |
| PRESS Correction Function | 0 |

One or more of these may comprise modifications from similar settings that may be provided for PROSE, either as defaults or as user defined settings for a particular other application than as featured in the various aspects hereunder this disclosure. These CV settings, in context of use as modifications generally to a sequence otherwise sharing significant similarities to PROSE, are believed to result in a highly beneficial resulting DDD-MRS sequence for the intended purpose of later signal processing, according to the DDD-MRS signal processor embodiments herein described, and performing a diagnosis of DDD pain in discs examined (the latter according for example to the DDD-MRS diagnostic processor aspects & exemplary embodiments also herein disclosed). However, it is also appreciated that these specific settings may be modified by one of ordinary skill and still provide highly beneficial results, and are also contemplated within the broad intended scope of the various aspects of this present disclosure.

Data Acquisition

The signal detected in the MR spectrometer in the receiving "detector" coil assembly, after exposing a sample to a radio frequency pulse, is called the Free Induction Decay (FID). In modern MR spectrometers the MR signal is detected using quadrature detection. As a result, the acquired MR signal is composed of two parts, often referred as real and imaginary parts of FID. The time domain FID waveform is shown in FIG. 5, which shows the real (Sx) and imaginary (Sy) parts of an FID (right) that correspond to x and y components of the rotating magnetic moment M.

FIDs are generated at the period defined by TR. Thus a TR of about 1000 milliseconds, according to the exemplary embodiment described above, equals a rate of about 1 Hz (about one FID per second). The FID signal received from each coil channel is digitized by the scanner to generate a 1024 point complex number data set or acquisition frame. An MRS scan session consists of sixteen frames of unsuppressed water FIDs and up to 368 frames of suppressed water FIDs, which together are considered an acquisition series. The unsuppressed water FIDs provide a strong water signal that is used by the signal processing to determine which coils to use in the signal processing scheme as well as the phase information from each coil. However, due to gain and dynamic range in the system these high water content unsuppressed frames do not typically provide appropriate resolution in the target biomarker regions of the associated spectra to use them for diagnostic data purposes. The suppressed water FIDs are processed by the DDD-MRS processor to obtain this spectral information, though utilizing the unsuppressed frames for certain processing approaches taken by the processor. FIG. 6 shows the plot of all the FIDs obtained in an MRS scan, and is an amplitude plot of complex data from a standard DDD-MRS acquisition with the y-axis representing the magnitude of FID data and the x-axis representing serial frame count over time.

Data Transfer

The scanner generates the FIDs using the defined sequences to energize the volume of interest (VOI), digitizes them according to the defined data acquisition parameters, and stores the data as floating point numbers. A data descriptor header file (DDF) with all the aforementioned parameters along with voxel prescription data is appended to the data to generate the archive file. Examples of parameters from the GE Signa DDF are shown below as follows:

BW=2000 (Bandwidth of complex sampled data, in Hz)

FS=2000 (Sample frequency rate, in complex samples per second)

TE=28 (Echo time, in mS)

TR=1000 (Repetition time, in mS)

NWUF=16 (Number of initial Water-Unsuppressed frames)

The archive file may then be transferred to another computer running an application, such as Matlab® R2009a (e.g. with "Image Processing Toolbox" option, such as to generate time-intensity plots such as shown in various Figures hereunder), which opens the archive file. The Matlab application is programmable, and is further programmed to signal process the acquired and transferred DDD-MRS information contained in the archive file, such as according to the various signal processing embodiments hereunder. Other packages, such as "C," "C+," or "C++" may be suitably employed for similar purpose. This application, subsequently referred to as the DDD-MRS signal processor, parses information pertinent to the signal processing of the data from the data description header, and imports the FID data acquired at each detector coil for subsequent signal processing. It will be understood that the DDD-MRS signal processor can be implemented in a variety of manners, such as using computer hardware, firmware, or software, or some combination thereof. In some embodiments, the DDD-MRS signal processor can comprise a computer processor configured to execute a software application as computer-executable code stored in a computer-readable medium. In some embodiments, the computer processor can part of a general purpose computer. In some embodiments, the DDD-MRS signal processor can be implemented using specialized computer hardware such as integrated circuits instead of computer software.

Signal Processing

Figure 7:
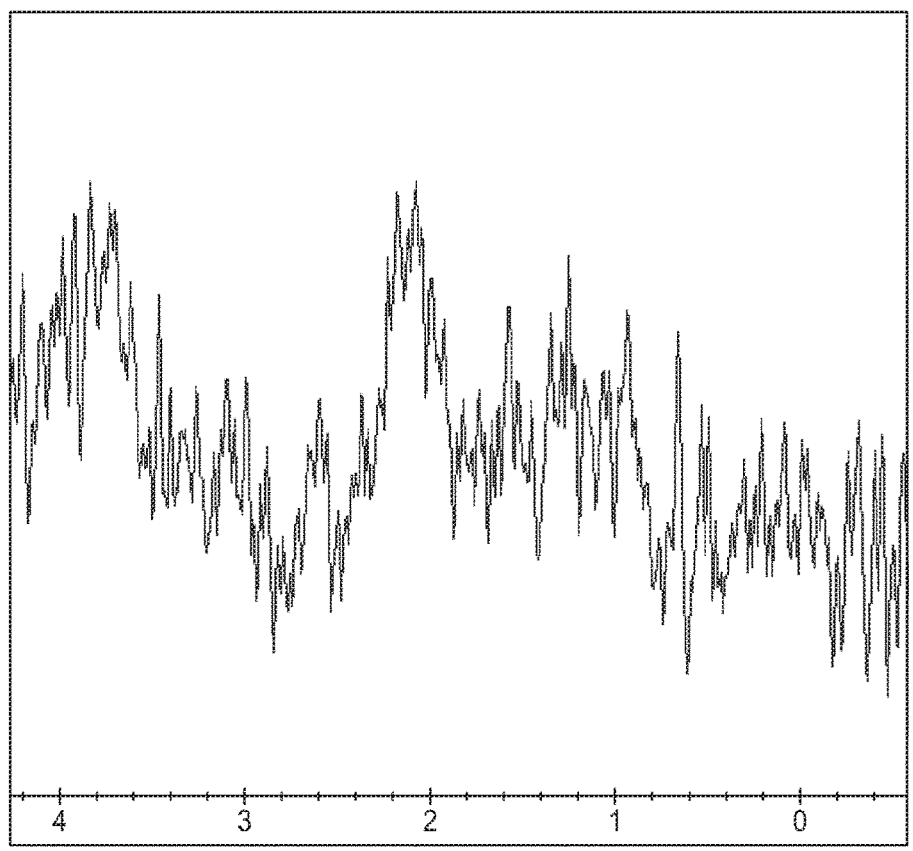
FIG. 7 shows a graph of an exemplary spectrum produced as the output average after combining all of 6 activated acquisition channels and averaging all frames, such as typically provided in display by a GE Signa, and is pre-applying the various signal processing approaches of the present disclosure.
Figure 8:
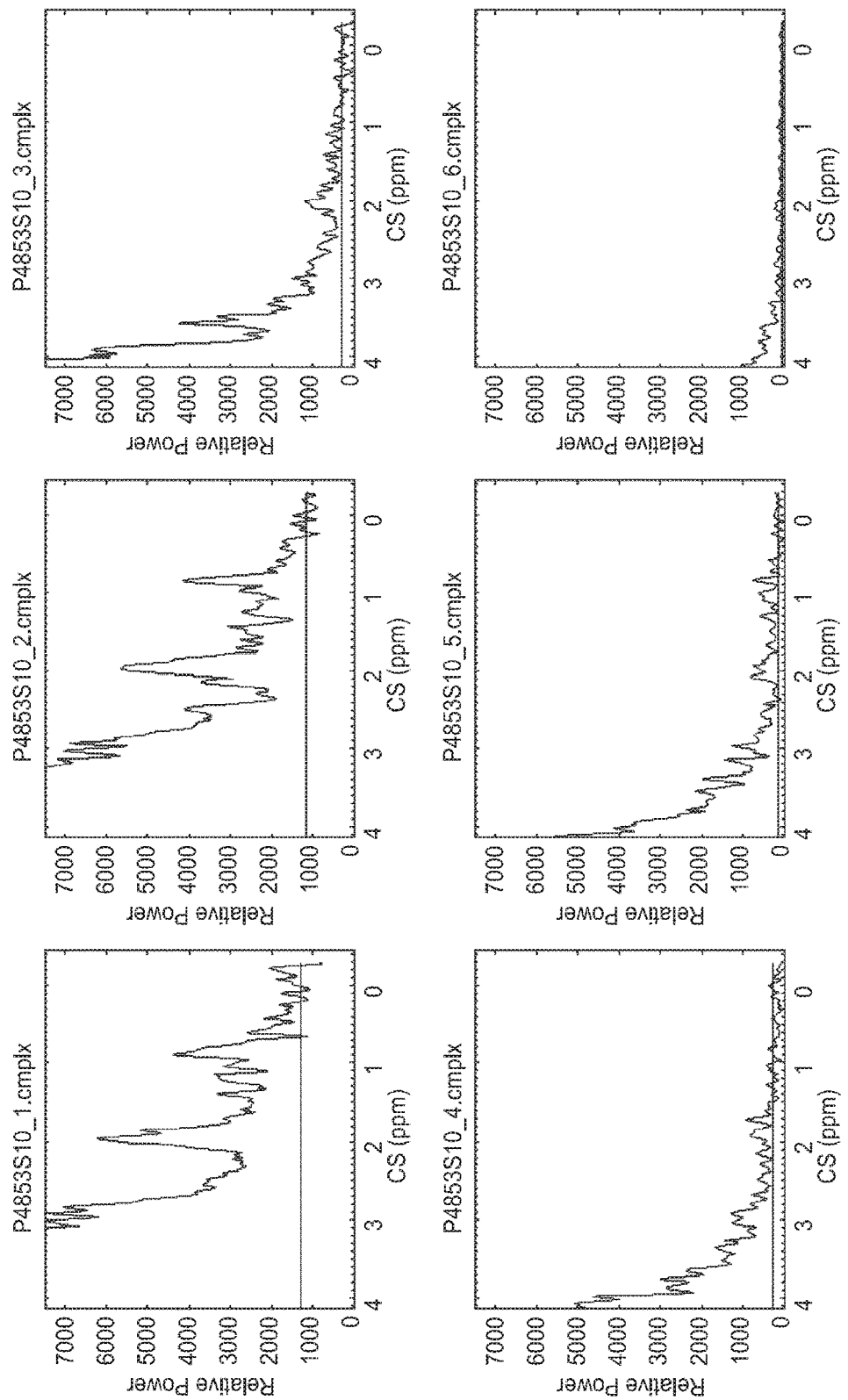
FIG. 8 shows a graphical display of individual channel spectra of all uncorrected channels of the same MRS acquisition featured in FIG. 7 prior to combining the channels, and is also pre-processing according to the signal processing approaches of the present disclosure.
Figure 9:
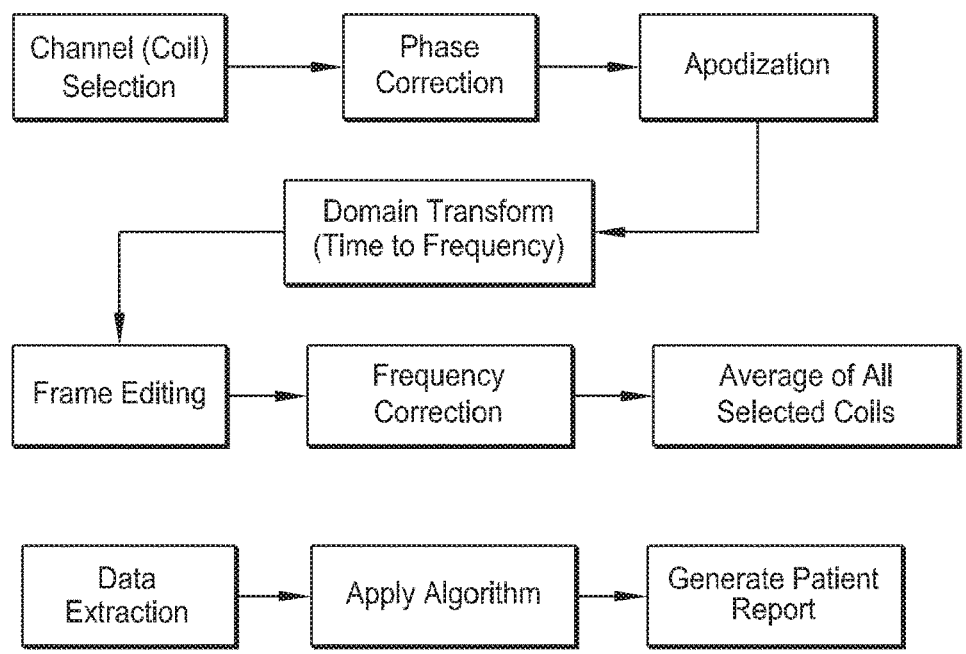
FIG. 9 shows a schematic flow diagram of one DDD-MRS processor configuration and processing flow thereunder, first operating in DDD-MRS signal processor mode by conducting optimal channel (coil) selection, then phase correcting, then apodizing, then transforming domain (from time to frequency), then editing out poor frames, then correcting for frequency shifts, then averaging of all selected coils, and then followed by DDD-MRS diagnostic processor & processing flow of data extraction, then apply the algorithm, then generate a patient report.

Upon the acquisition of all MRS data, the scanner will typically provide the operator with a spectral image that is the averaged combination of all frames across all the 6 detection channels (coils). An example of such a waveform is shown in FIG. 7, which shows a typical scanner-processed spectral signal plot of combined, averaged channels. FIG. 8 shows the magnitude only (no correction) images of each of the six channels which form the output from the Signa system shown in FIG. 7, and thus input to the DDD-MRS signal processor.

According to one highly beneficial mode, the DDD-MRS signal processor is configured to conduct a series of operations in temporal fashion as described hereunder. While this configuration is considered highly beneficial, these same or similar tasks may be performed in different order, as would be apparent to one of ordinary skill.

According to the current exemplary embodiment, the first operation of the DDD-MRS processor assesses the SNR of each coil. This is done to determine which coils have acquired sufficiently robust signal to use for data processing & averaging—the result may produce one single coil that is further processed, or multiple coils later used combination under multi-coil averaging. In the majority of acquired signals observed, only a subset of the 6 lumbar acquisition coils were determined to be sufficiently robust for use. However, the standard system output averages all 6 coils. Accordingly, this filtering process alone—removing poor signal coils and working with only stronger signal coils—has been observed to dramatically improve processed spectra for diagnostic use. While various techniques may be suitable according to one of ordinary skill, and thus contemplated hereunder, according to the present exemplary embodiment the SNR is calculated by obtaining the average power in the first 100 data points (the signal) and the last 100 points (the noise) of the unsuppressed water FID. The unsuppressed water FIDs signals are used because of the strong water signal. The coil channel with the greatest SNR, and channels within 3 dB of that strongest one, are preserved as candidates for multi-coil averaging—other coil channels falling below this range are removed from further processing.

Further to the exemplary present embodiment, a second operation conducted by the DDD-MRS processor is phase alignment. This is performed to support coherent summation of the signals from the selected coil channels and the extraction of the absorption spectra. This is necessary because a systemic phase bias is present in the different coil channels. This systemic phase bias is best estimated by analysis of the 16 data frames collected at the beginning of each scan without water suppression. This operation, according to one exemplary mode, analyzes the phase sequence of the complex samples and fits a polynomial to that sequence. A first-order (linear) fit is used. This provides a better estimate of the offset than simply using the phase of the first sample, as is often done. This is because eddy current artifacts, if present, will be most prominent in the first part of the frame. The offset of the linear fit is the initial phase. Observation has indicated that the first 150 samples (75 mS at the typical 2000 samples-per-second rate) typically provide reliable phase data. The fit is performed on each of the 16 water-unsuppressed frames for each coil channel and the mean phase of these 16 is used to phase adjust the data for the corresponding coil channel. This is accomplished by performing a phase rotation of every complex sample in each frame to compensate for the phase offset as estimated above, setting the initial phase to zero.

Figure 10:
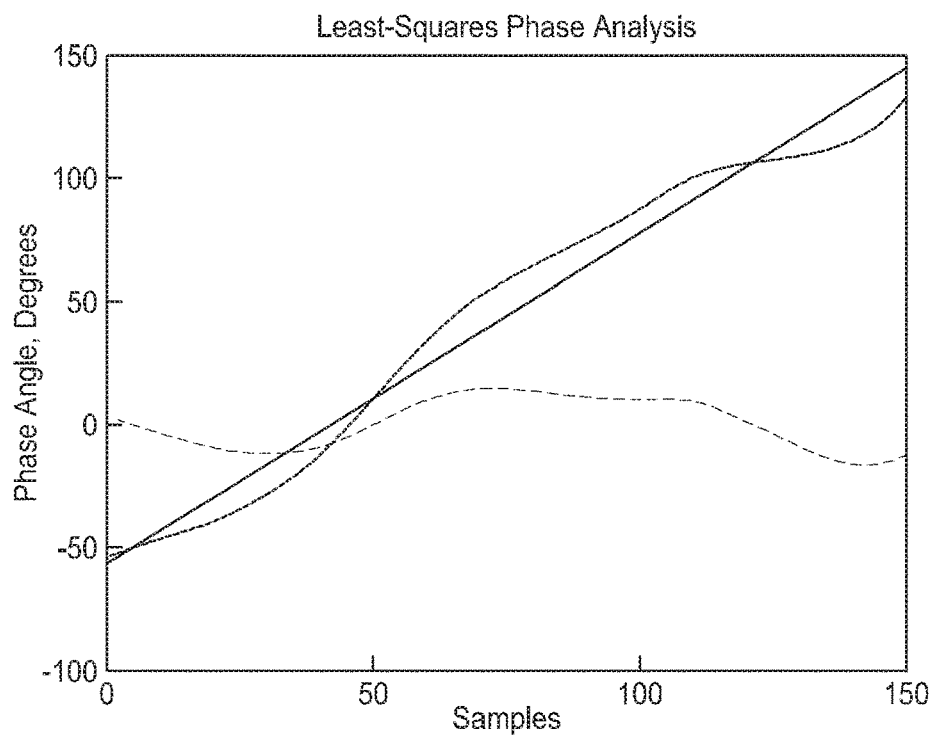
FIG. 10 shows a plot of phase angle pre- and post-phase correction for an exemplary acquisition series for a disc such as that featured in different modes of spectral processing in FIGS. 6-9.
Figure 11:
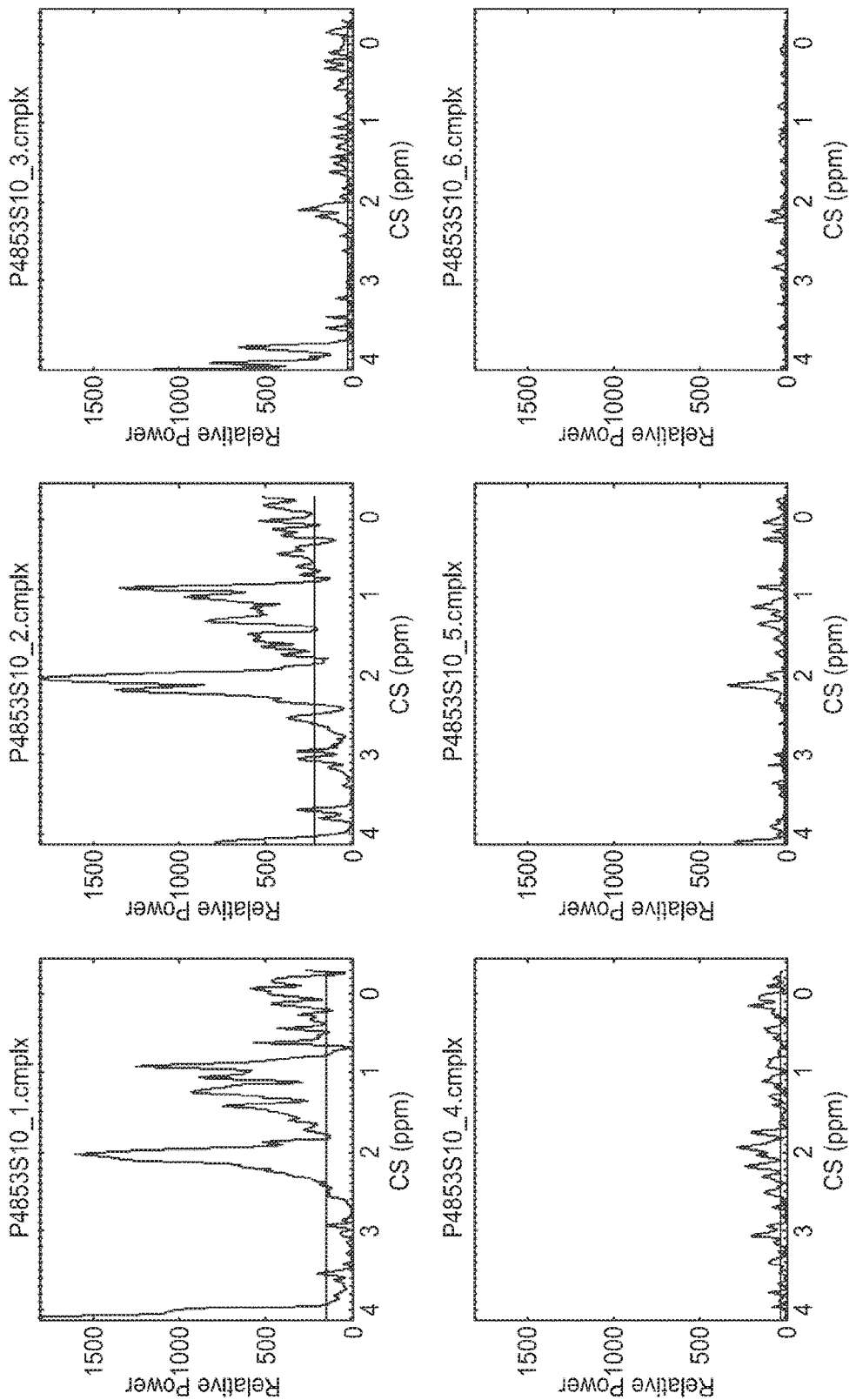
FIG. 11 shows the individual channel averages shown in FIG. 8, but after phase correcting consistent with the signal processing flow shown in FIG. 9 and phase-correction approach illustrated in FIG. 10.
Figure 12:
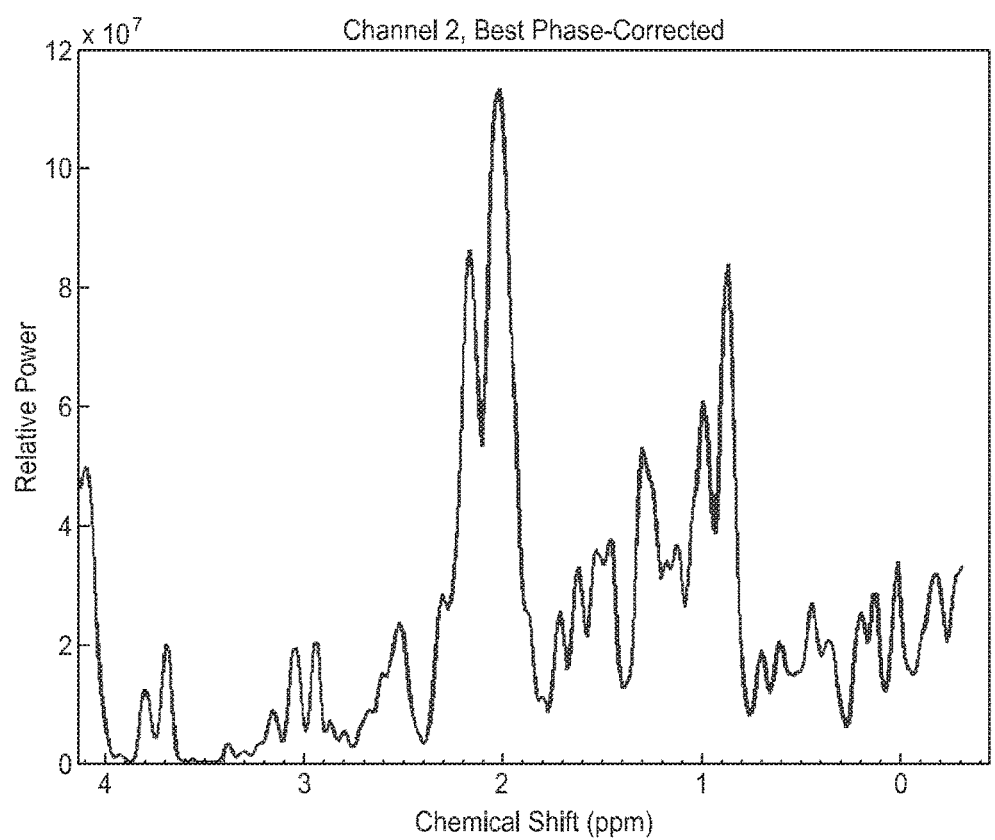
FIG. 12 shows the frame-averaged spectrum after combining the strongest two channels (channels 1 and 2) selected among the 6 phase-corrected frame-averaged channel spectra shown in FIG. 11 using a channel selection approach and criterion according to a further aspect of the current disclosure.

The offset of the linear fit is the phase bias with respect to zero and the slope is the frequency error with respect to perfect center-tuning on the water signal. Only the offset portion of the curve fit is used to phase correct the data. An example of this is shown in FIG. 10, which shows phase angle before and after phase correction. The phase angle signal is shown as the dotted line. The solid line is the least squares fit estimate. The dashed line is the phase and frequency corrected signal, though the offset component is used to phase correct and frequency correction is performed subsequently in the temporal process according to the present exemplary DDD-MRS processor embodiment. The results of phase correction for each of all the six channels is shown in FIG. 11, with channels 1-3 indicated from left to right at the top, and channels 4-6 indicated from left to right at the bottom of the figure. The averaged spectrum of the selected, phase corrected channels (channels 1 and 2) is shown in FIG. 12.

Frequency Correction

During the course of a typical acquisition cycle (e.g. about 4 minutes), frequency errors can occur due to patient motion and changes in susceptibility (respiration, cardiac cycle etc.). In this environment where the acquired spectral signals "shift" along the x-axis between multiple sequential frames in an exam series, their subsequent averaging becomes "incoherent"—as they are mis-aligned, their averaging compromises signal quality. Unless this is corrected to "coherently" align the signals prior to averaging, this error can result in an increase in line width, split spectral peaks and reduced peak amplitudes for diminished spectral resolution relative between signal peaks themselves (as well as SNR). Accordingly, the DDD-MRS processor performs frequency correction prior to averaging frames. This is performed according to one exemplary embodiment in the frequency domain. This is done by transforming the time domain data for each frame into frequency domain absorption spectra, locating the water absorption peaks, and shifting the spectrum to align them to an assigned center reference location or bin. Once shifted, the frame spectra are averaged in the frequency domain to generate the corrected or "coherent" channel spectra. In another embodiment, the desired frequency shift correction for a frame may be applied to the time domain data for that frame. The time domain data for all the frames would then be averaged with the final average then transformed back to spectra. While the processes are linear and thus not dependent upon sequence of operation, it is believed in some circumstances that the latter embodiment may present slightly increased spectral resolution. In difficult signal acquisition situations, some of the frames do not have sufficient signal quality to support frequency correction. More specifically, water signal is insufficiently robust to accurately "grab" its peak with high degree of confidence. This circumstance is addressed by another operation of the DDD-MRS processor, frame editing, described in the next section.

Figure 13:
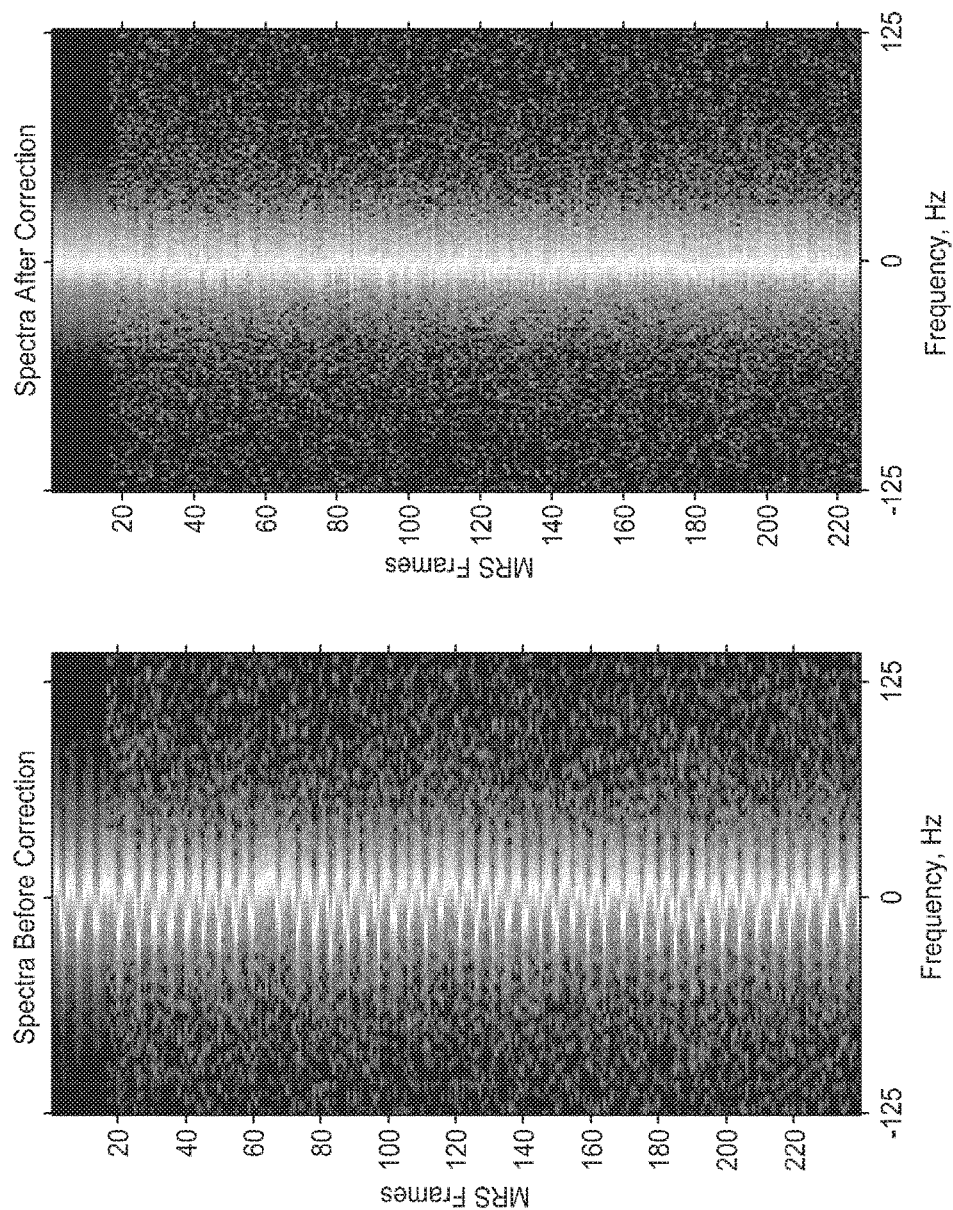
FIG. 13 shows time-intensity plots of an exemplary series acquisition for a disc pre-(left) and post-(right) frequency correction according to a further aspect of the present disclosure, and shows each acquisition frame as a horizontal line along a horizontal frequency range with brightness indicating signal amplitude (bright white indicating higher amplitude, darker indicating lower), and shows the series of related repetitive frames in temporal relationship stacked from top to bottom e.g. top is time zero).
Figure 14:
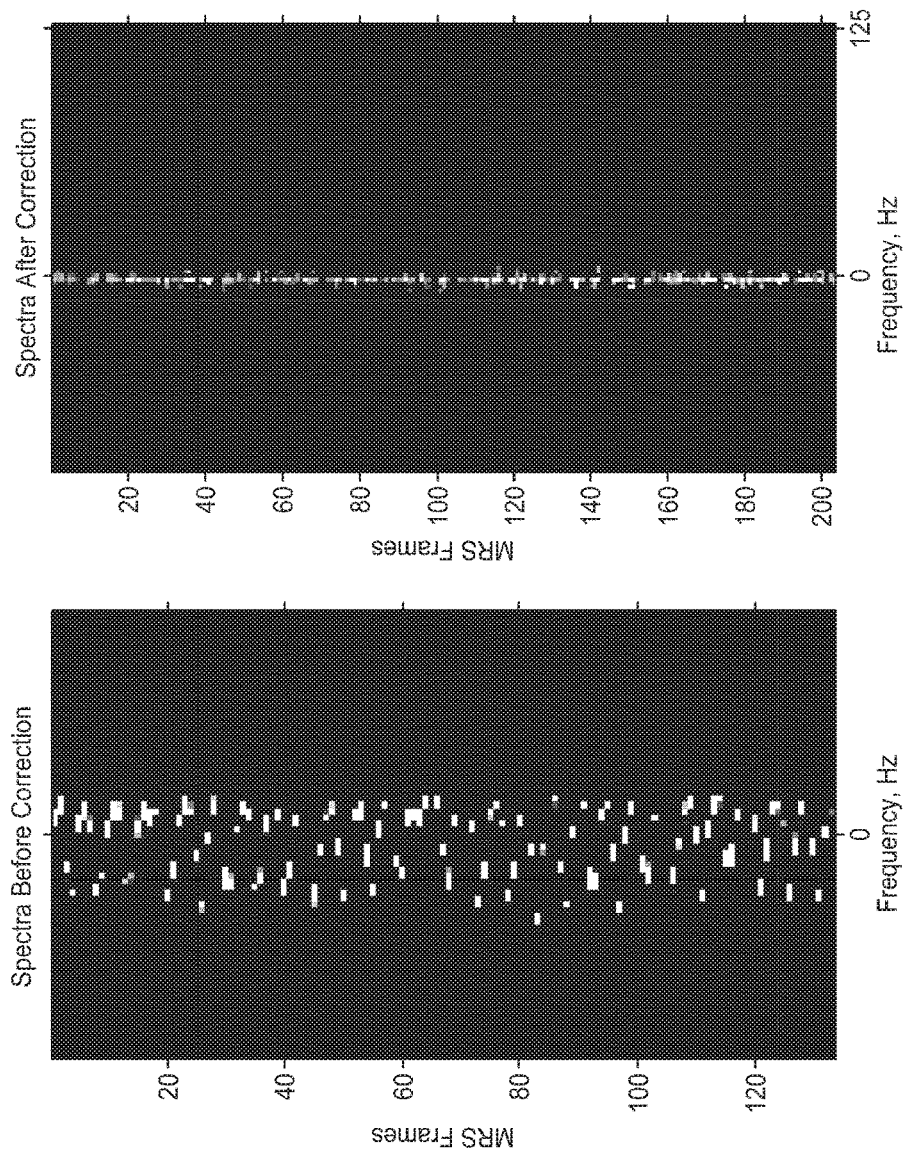
FIG. 14 shows the same time-intensity plots shown in FIG. 13 pre-(left) and post-(right) frequency correction, but in enhanced contrast format.

Frequency error can be visualized using a time-intensity plot of the absorption spectra of all the frames in an acquisition cycle. As shown in FIG. 13, each acquisition frame is represented by a horizontal line, with amplitude of signal intensity across the frequency spectrum indicated by brightness in grey scale (brighter shade/white designates higher amplitude, darker signal intensity indicates lower relative amplitude). The horizontal lines representing individual acquisition frames are displayed in vertically "stacked" arrangement that follows their temporal sequence as acquired, e.g. time zero is in the upper left corner and frequency incremented from left to right. The top 16 lines represent unsuppressed water frames, with the remainder below representing suppressed water acquisitions. The brightest portion of each line is reliably recognized as the water peak absorption, typically the strongest signal of acquired MRS spectra in body tissues. Further to FIG. 13, this plot for the original acquired sequence of frames from an acquisition series intended to be averaged is shown pre-frequency correction (e.g. with original frequency locations) on the left, and post-frequency correction on the right. Shifting of the location of this bright white water peak region, as observed between vertically stacked frames, indicates frequency shift of the whole MRS spectrum between those frames—including thus the peaks of spectral regions of interest related to chemicals providing markers for pain. The rhythmic quality observed in this frequency shifting, per the alternating right and left shifts seen around a center in the uncorrected plot (left side of figure) shift, remarkably approximates frequency of respiration—and thus is believed to represent respiration-induced susceptibility artifact. The contrasted plots seen in the pre and post frequency corrected time intensity plots shown in FIG. 13 reveal the corrected "alignment" of the previously shifted signals for coherent averaging. For further clarity, an enhanced contrast image (FIG. 14) shows the original frequency shifted, incoherent mis-alignment (left pane) and frequency corrected, coherent alignment (right pane) of the water peaks from this same acquisition series. In this exemplary case shown in FIGS. 13-14, all of the frames were of sufficient quality to support frequency correction.

Figure 15:
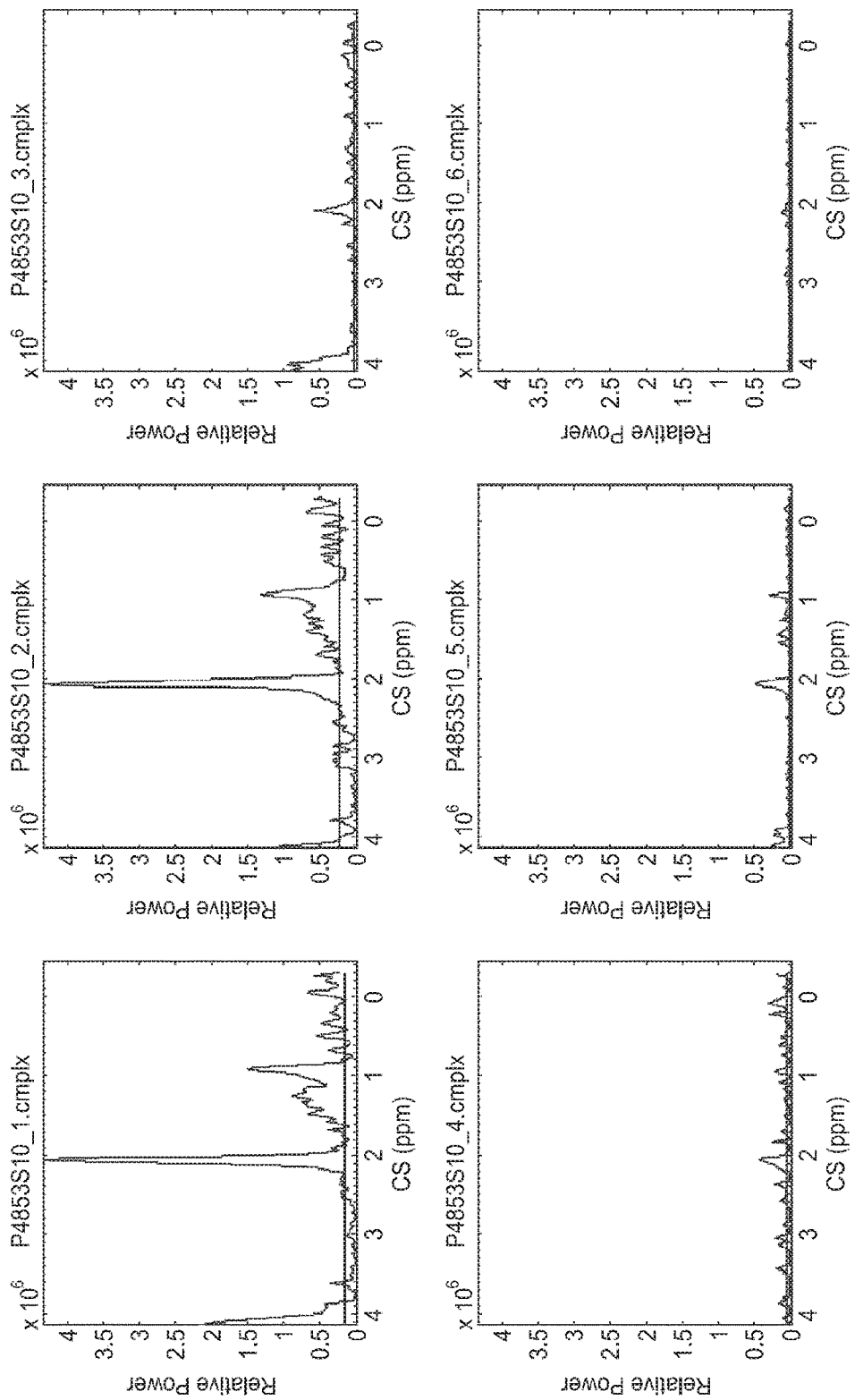
FIG. 15 shows spectral plots for 6 frame-averaged acquisition channels for the same acquisition shown in FIGS. 8 and 11, except post phase and frequency correction and prior to optimal channel selection and/or combination.
Figure 16:
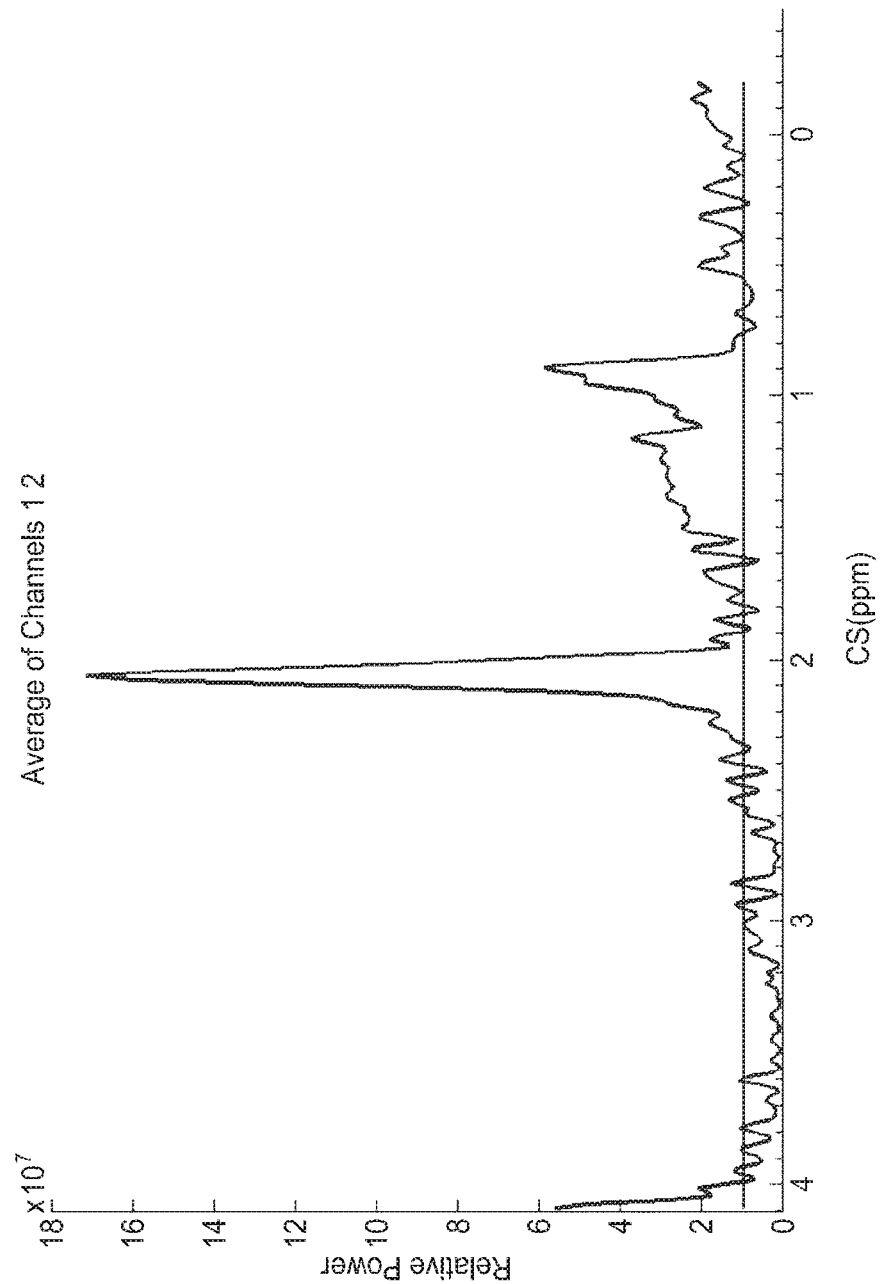
FIG. 16 shows a spectral plot for averaged combination of frame-averaged, phase and frequency corrected channels 1 and 2 selected from FIG. 15.

The frequency corrected absorption spectra for each acquisition cycle are averaged to generate an average frequency (and phase) corrected spectra for each channel, as is shown in FIG. 15. The selected channels (channels 1 and 2) are then averaged to produce the final spectra (FIG. 16) used for extraction of data along spectral regions of interest that are considered relevant to DDD pain diagnosis.

Frame Editing

While it is contemplated that in some circumstances individual MRS acquisition frames may provide some useful information, frame averaging is prevalently indicated in the vast majority of cases to achieve a spectrum with sufficient SNR and interpretable signal at regions of interest for pathology assessment. It is, at most, quite rare that an individual frame will have sufficient SNR for even rudimentary metabolite analysis to the extent providing reliable diagnostic information. Often individual frames along an acquisition series will have such low SNR, or possess such artifacts, that they make no improvement to the average—and in fact may even degrade it. To the extent these "rogue" frames may be recognized as such, they may be excluded from further processing—with only robust frames remaining, the result should improve.

Figure 17:
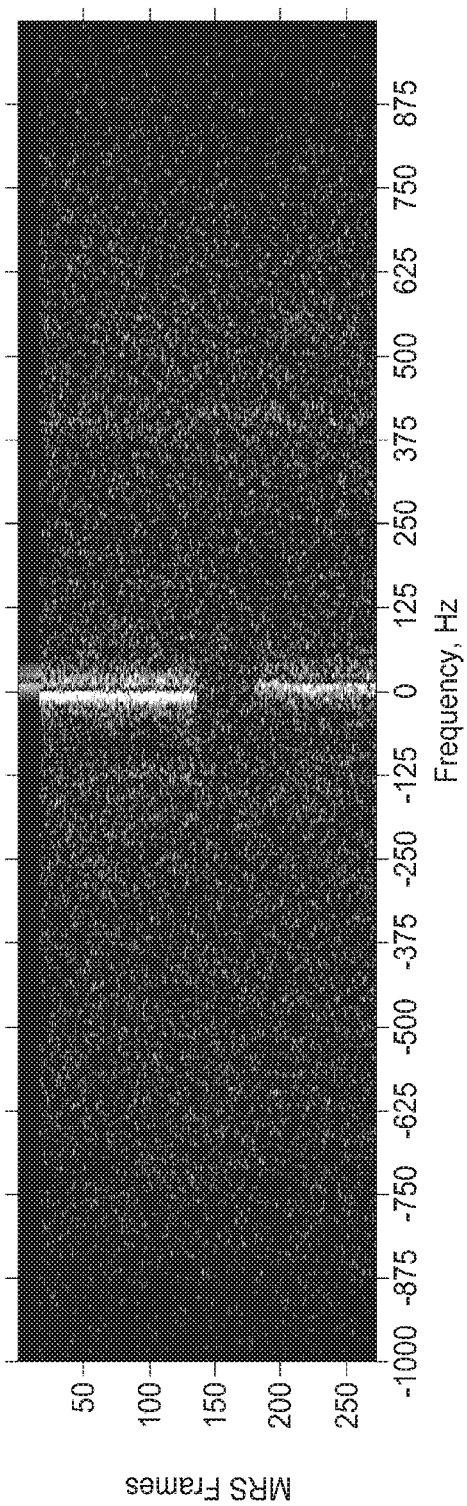
FIG. 17 shows an exemplary time intensity plot for a DDD-MRS acquisition similar to that shown in FIG. 13 (left), except for an acquisition series with corrupted frames.

Accordingly, a further mode of the present exemplary DDD-MRS processor embodiment utilizes frame editing to identify those frames which vary sufficiently from the expected or otherwise observed acquisition results such that they should be excluded. In one aspect of the underlying concern, certain patient motions during an acquisition may result in signal drop-out as well as frequency shifts (e.g. susceptibility artifact). While involuntary motion, e.g. respiration, is a common cause of frequency shifts, these are typically sufficiently minor and within a range that they are not believed to implicate signal quality other than the shift itself (which can be corrected). However, other more significant movements (e.g. voluntary) may cause sufficiently significant shifts to seriously degrade the acquired spectrum (e.g. may move the voxelated region to include adjacent tissues versus only the intended ROI upon prescription prior to the motion). If the salient artifact is frequency shift, a correction may be applied and the frame can be used to make a positive contribution to the averaged spectrum. If a frame is discarded its contribution is lost, and across sufficient number of discarded frames across a series the result may not include a sufficient number of frames in the average for a reliable SNR in the resulting spectrum. The DDD-MRS processor, according to the current exemplary embodiment, analyzes the residual water signal in each frame to determine if it is of sufficient quality to support frequency correction. FIG. 17 is a time-intensity plot which illustrates a scan series with frequency shifts and "drop outs" with SNR changes considered to represent corrupted frames due to patient motion. In this particular example, after excluding the "drop out" frames (center of time sequence between about 75 and 175 MRS frames, it was still possible to obtain a high quality final averaged spectrum from this scan using the remaining robust frames.

Figure 18:
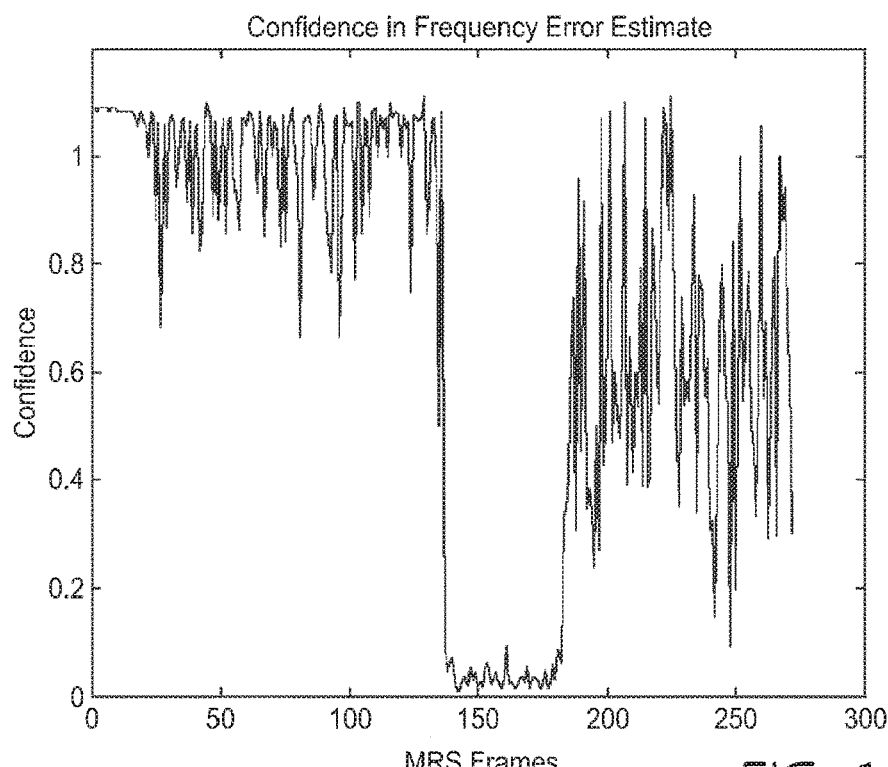
FIG. 18 shows confidence in frequency error estimate vs. MRS frames temporally acquired across an acquisition series for a disc, as plotted for the series acquisition shown in different view in FIG. 17.
Figure 19:
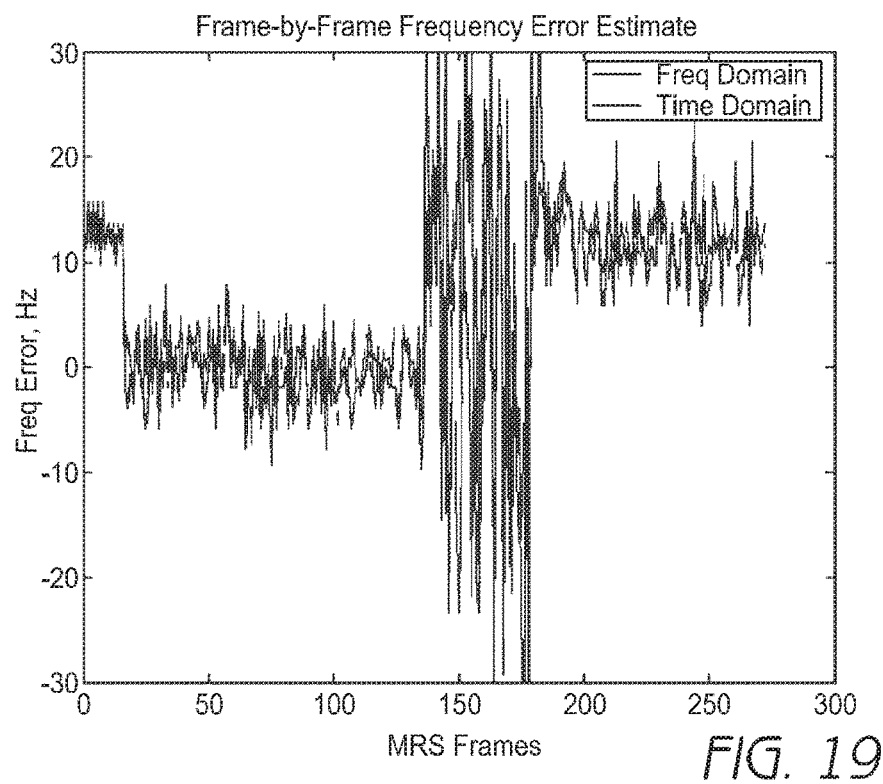
FIG. 19 shows a frame by frame frequency error estimate of the acquisition series featured in FIG. 18.

FIGS. 18 and 19 show the confidence in the frequency error estimate and the frequency error, respectively, which are used according to the present exemplary embodiment for frame editing. More specifically, FIG. 18 shows confidence in the frequency error estimate, with confidence level on the Y-axis, and the sequential series of frame acquisitions along a scan indicated along the X-axis. FIG. 19 shows the actual frequency error along the Y-axis, for the same frame series along the X-axis, while the frequency error is reflected in both frequency domain and time domain contexts. This is based on analyzing the characteristics of the residual water peak and the noise in a band 80 Hz wide (for 3T processing, it would be 40 Hz wide at 1.5T) around the center-tuned frequency. The largest peak is assumed to be the water signal and the assumption is qualified by the confidence estimate. If the confidence value is above 0.7, the frequency error estimate is considered valid and the frame is flagged as a candidate for frequency correction. As seen from the plots, when the confidence is low, the variance of the frequency error estimate is greatly increased. The final qualification step is to determine if there are enough qualified candidate frames to achieve sufficient SNR improvement when averaged. This threshold has been empirically established as 90 frames, according to the present exemplary embodiment, though other limits may be appropriate in various circumstances.

Figure 20:
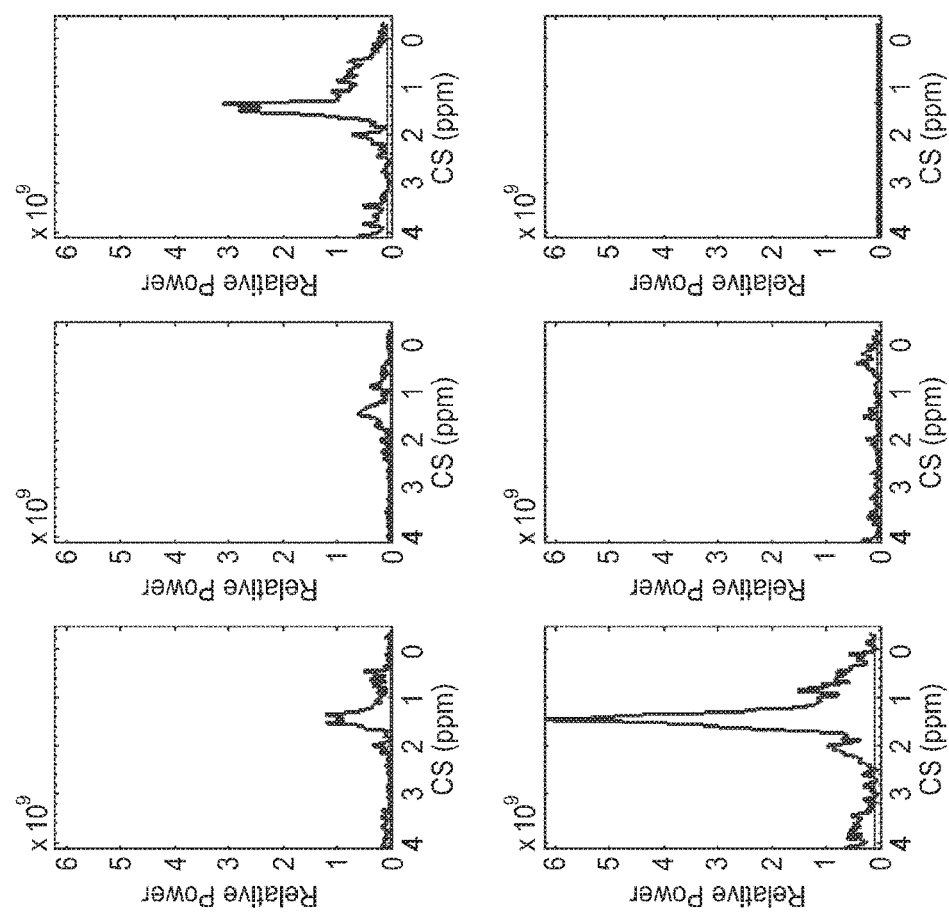
FIG. 20 shows all 6 frame-averaged acquisition channels for the series acquisition conducted on the disc featured in FIGS. 17-19, prior to correction.
Figure 21:
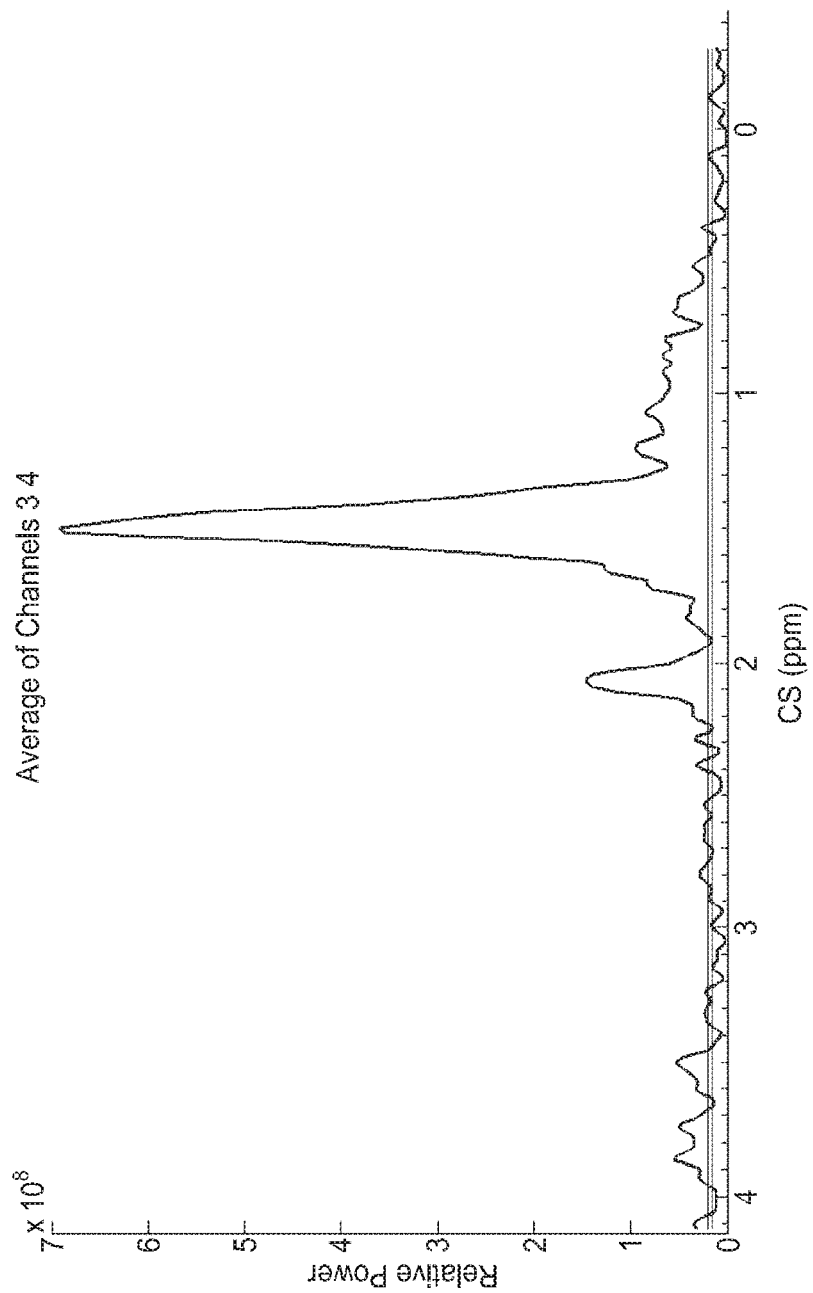
FIG. 21 shows phase, frequency, and frame edited spectral average combining channels 3 & 4 after optimal channel selection, for the same series acquisition featured in FIGS. 17-20.

For further understanding & clarity re: the ultimate impact frame editing as described hereunder, the unprocessed power plot for all six channels from the patient with the compromised frames examined in various views in prior Figures is shown in the FIG. 20, whereas the frequency and phase corrected, and frame edited, spectra is shown in FIG. 21 (averaged channels 3 and 4).

The following documents are herein incorporate in their entirety by reference thereto:

1. Bottomley P A. Spatial localization in NMR spectroscopy in vivo. Ann N Y Acad Sci 1987; 508:333-348.
2. Brown T R, Kincaid B M, Ugurbil K. NMR chemical shift imaging in three dimensions. Proc. Natl. Acad. Sci. USA 1982; 79:3523-3526.
3. Frahm J, Bruhn H, Gyngell M L, Merboldt K D, Hanicke W, Sauter R. Localized high-resolution proton NMR spectroscopy using stimulated echoes: initial applications to human brain in vivo. Magn Reson Med 1989; 9:79-93.
4. Star-Lack J, Nelson S J, Kurhanewicz J, Huang L R, Vigneron D B. Improved water and lipid suppression for 3D PRESS CSI using RF band selective inversion with gradient dephasing (BASING). Magn Reson Med 1997; 38:311-321.
5. Cunningham C H, Vigneron D B, Chen A P, Xu D, Hurd R E, Sailasuta N, Pauly J M. Design of symmetric-sweep spectral-spatial RF pulses for spectral editing. Magn Reson Med 2004; 52:147-153.
6. Pauly J, Le Roux P, Nishimura D, Macovski A. Parameter relations for the Shinnar-Le Roux selective excitation pulse design algorithm [NMR imaging]. IEEE Trans Med Imaging 1991; 10:53-65.
7. F. Jiru, Europeant Journal of Radialogy 67, (2008) 202-217

The following U.S. Patent Application Publications are herein incorporated in their entirety by reference thereto: US2008/0039710 to Majumdar et al.; and US2009/0030308 to Bradford et al.

DDD-MRS Diagnostic Processor and Use for Diagnosing DDD Pain

Development, application, and evaluation of a DDD-MRS diagnostic processor configured for use for diagnosing DDD pain based upon DDD-MRS acquisition series acquired from discs according to a DDD-MRS pulse sequence and DDD-MRS signal processor applications is disclosed by reference to Example 1 below and according to other disclosure provided elsewhere hereunder. It will be understood that the DDD-MRS diagnostic processor can be implemented in a variety of manners, such as using computer hardware, software, or firmware, or some combination thereof. In some embodiments, the DDD-MRS diagnostic processor can include a computer processor configured to execute a software application as computer-executable code stored in a computer-readable medium. In some embodiments, the computer processor can be part of a general purpose computer. The computer processor used by the DDD-MRS diagnostic processor can be the same computer processor used by the DDD-MRS signal processor, or it can be one or more separate computer processors. In some embodiments, the DDD-MRS diagnostic processor can be implemented using specialized computer hardware such as integrated circuits instead of computer software.

Example 1

A DDD-MRS pulse sequence & signal processor were constructed to incorporate various aspects of the present embodiments disclosed hereunder and were used and evaluated in clinical experience across a population of discs in chronic, severe low back pain patients and asymptomatic control volunteers. Various data extracted from features of interest along the acquired & processed DDD-MRS acquisition series for discs evaluated in these subjects were compared against control diagnoses for severe disc pain vs. absence severe disc pain, in order to develop & characterize a DDD-MRS diagnostic processor with the highest possible correlation to the control diagnoses.

Methods:

Clinical Study Population: The study included 65 discs from 36 total subjects. Thirty-eight discs were from 17 patients with a clinical diagnosis of chronic, severe low back pain (LBP group), and 27 discs were from 19 asymptomatic volunteers (ASY Group). 25 discs in 12 of the LBP patients also received PD (PD Group) sufficiently contemporaneous with the DDD-MRS exam to provide appropriate comparison basis. All 65 discs were evaluated for single voxel magnetic resonance spectroscopy pulse sequence & data acquisition (DDD-MRS), and signal processor parameter development of the new DDD-MRS approach. 52 discs from 31 subjects were considered appropriate and used as controls for developing and assessing the DDD-MRS diagnostic processor for diagnostic application of the overall DDD-MRS system and approach. Thirteen discography positive (PD+) discs from the PD Group were used as positive control (PC) discs, and 12 discography negative (PD−) discs from the PD Group plus all the ASY discs were used as negative control (NC) discs. A breakdown summary analysis of demographics among and between these groups is shown in Table 2.

TABLE 2

DDD-MRS Clinical Study Group Demographics & Comparison

| | DDD-MRS Clinical Study - Group Demographics | | |
|---|---|---|---|
| | Pain Patients | Asymptomatics | p value |
| By SUBJECT (n = 31) | | | |
| n = | 12 | 19 | |
| Male | 7 (58%) | 9 (47%) | |
| Female | 5 (42%) | 10 (53%) | |
| Age | 46.6 ± 9.4 | 32.4 ± 11.3 | ** 0.0006 |
| Height | 68.3 ± 4.1 | 66.8 ± 4.5 | 0.1805 |
| Weight | 172.5 ± 38.5 | 151 ± 36.3 | 0.0639 |
| BMI | 25.9 ± 4.4 | 23.7 ± 3.99 | 0.0824 |
| By DISCS (n = 52) | | | |
| n = | 25 | 27 | |
| Male | 16 (64%) | 16 (59%) | |
| Female | 9 (36%) | 11 (41%) | |
| Age | 46.2 ± 9.04 | 35.2 ± 14.6 | ** 0.0010 |
| Height | 68.7 ± 4.03 | 67.9 ± 4.5 | 0.2584 |
| Weight | 177.4 ± 39.3 | 157.6 ± 39.5 | * 0.0381 |
| BMI | 26.2 ± 4.4 | 23.8 ± 4.3 | * 0.0280 |
| | Pos. Controls | Neg. Controls | p value |
| By DISCS (n = 52) | | | |
| n = | 13 | 39 | |
| Male | 8 (62%) | 24 (62%) | |
| Female | 5 (38%) | 15 (38%) | |
| Age | 46 ± 9.7 | 38.7 ± 13.9 | * 0.0445 |
| Height | 68.9 ± 3.7 | 68.1 ± 4.4 | 0.2661 |
| Weight | 182.4 ± 35.9 | 162 ± 40.8 | 0.0570 |
| BMI | 26.9 ± 4.2 | 24.4 ± 4.5 | * 0.0402 |

Figure 22:
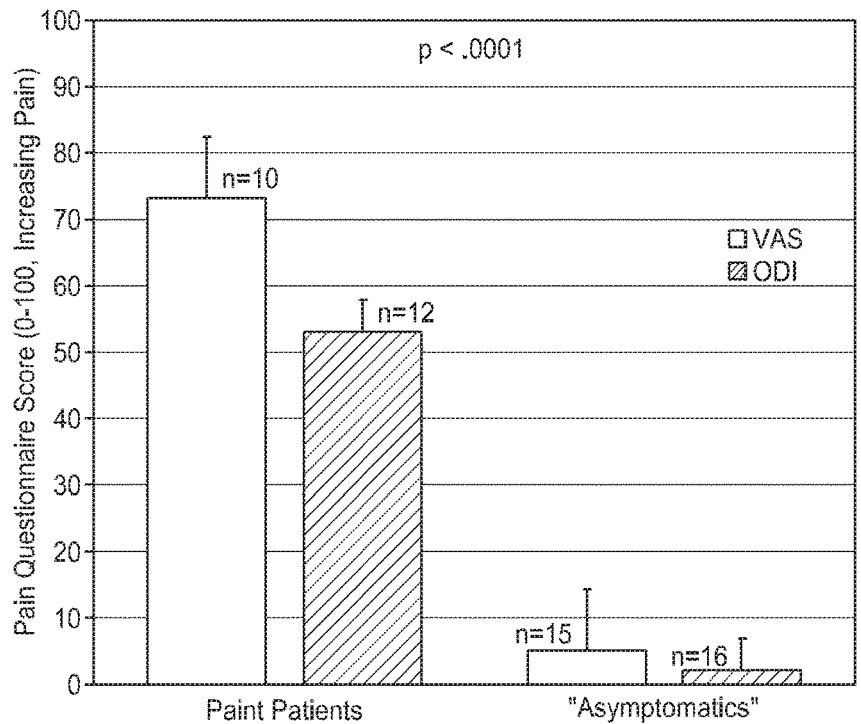
FIG. 22 shows a bar graph of mean values, with standard deviation error bars, of Visual Analog Scale (VAS) and Oswestry Disability Index (ODI) pain scores calculated for certain of the pain patients and asymptomatic volunteers evaluated in a clinical study conducted using certain physical embodiments of a diagnostic system constructed according to various aspects of the present disclosure.
Figure 23:
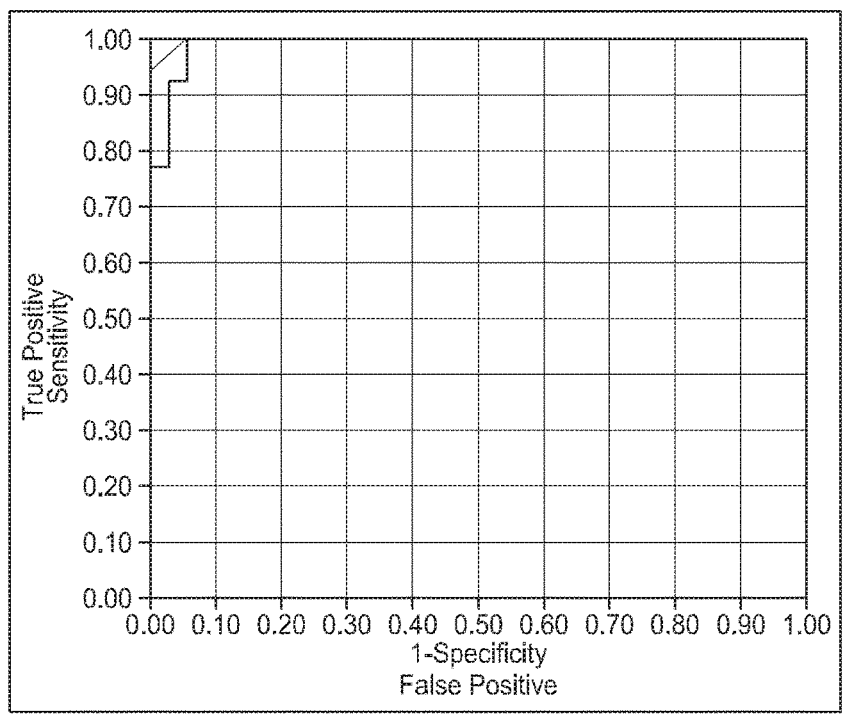
FIG. 23 shows a Receiver Operator Characteristic (ROC) curve representing the diagnostic results of the diagnostic system used in the clinical study with human subjects featured in part in FIG. 22, as compared against standard control diagnostic measures for presumed true diagnostic results for painful vs. non-painful discs.
Figure 24:
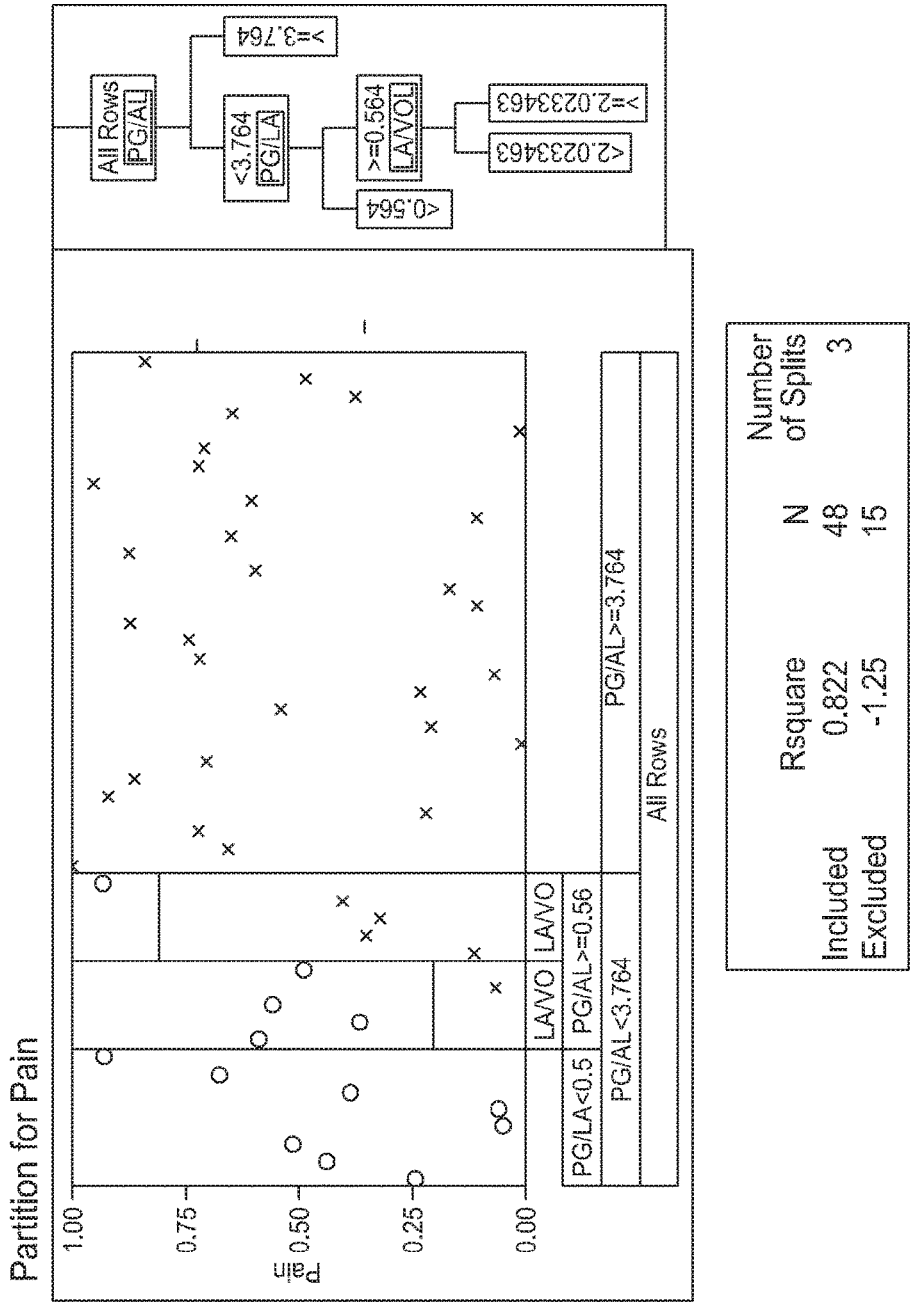
FIG. 24 shows a partition analysis plot for cross-correlation of a portion of the clinical diagnostic results of the DDD-MRS system under the same clinical study also addressed in FIGS. 22-23, based on partitioning of the data at various limits attributed to different weighted factors used in the DDD-MRS diagnostic processor, with "x" data point plots for negative control discs and "o" data point plots for positive control discs, also shows certain statistical results including correlation coefficient (R2).

Study Design: Standard lumbar MRI was performed on all subjects. PD performed within the PD Group was conducted by discographers per their discretionary techniques, and in all cases was performed blinded to DDD-MRS exam information. However, all PD+criteria included: >=6 pain intensity score concordant to typical back pain on PD; <=50 psi above opening pressure (where measured); and a negative control PD-disc in the same patient (except one). All PD-discs had <6 pain intensity scores per PD. Pain questionnaires, including ODI and VAS, were completed by all subjects, with PD Group significantly higher than the ASY Group according to both measures as shown in FIG. 22 (PD Group VAS & ODI on left side of graph, ASY Group VAS & ODI on right side of graph; VAS shown to left, ODI shown on right, within each group). The DDD-MRS pulse sequence and signal processor constructed according to the various present embodiments hereunder was used for each series acquisition for each disc, with data extracted from voxels prescribed at regions of interest within nuclei of all discs included in the study. A 3.0T GE Signa MRI system and 8-channel local spine detector coil were used with the DDD-MRS package and approach (lower 6 of the 8 channels activated for lumbar signal acquisition). Information along spectral regions of the acquired DDD-MRS signals and associated with various chemicals of interest were evaluated against control diagnoses across the PC and NC groups. Multi-variate logistic regression analyses were performed to fit the dicotomous response (PC vs NC) to the continuous spectral measures and develop a binary DDD-MRS diagnostic set of criteria and threshold for determining positive (MRS+) and negative (MRS−) pain diagnoses. A receiver operator characteristic (ROC) curve was generated, and area under the curve (AUC) was calculated to assess the accuracy of the developed test (FIG. 23). Five-fold cross-validation was performed to assess the generalizability of the predictive relationship (FIG. 24).

DDD-MRS diagnostic outcomes for each disc were based on a single number calculated via the developed set of criteria based upon four weighted factors derived from regions of the acquired MRS signals and associated with three chemicals—PG, LA, and alanine (AL). It is noted, however, that LA and AL regions are relatively narrow and immediately adjacent to each other, and in some cases the true respective signals representing these actual chemical constituents may overlap with each other and/or into the adjacent region's location. Furthermore, either or both of the LA and AL regions may also overlap with possible lipid contribution, which is believed to be observed in some cases (which may include signal from adjacent tissues such as bone marrow of bordering vertebral body/s). Positive numerical threshold results were assigned "MRS+" as severely painful, and negative results were assigned "MRS−" as not severely painful. Accordingly, the threshold for severely painful vs. otherwise non-painful diagnostic result is zero (0). The set of diagnostic criteria used to determine MRS+ vs. MRS− diagnostic values around this threshold with the most robust statistical correlation and fit to the control data observed across the disc population evaluated for this purpose is summarized as follows:

$$\text{Threshold} = -[\log(PG/LA*(0.6390061) + PG/AL*(1.45108778) + PG/\text{vol}*(1.34213514) + LA/\text{VOL}*(-0.5945179) - 2.8750366)];$$

wherein:
PG=peak measurement in PG region, AL=peak measurement in AL region, LA=peak measurement in LA region, and vol=volume of prescribed voxel in disc used for MRS data acquisition.

The distribution of DDD-MRS results according to these calculated thresholds were compared against all PC and NC diagnoses, PD results alone, and portion of the NC group represented by the ASY group alone. Sensitivity, specificity, and positive (PPV) and negative (NPV) predictive values were also calculated per control comparisons.

Results:

DDD-MRS data demonstrated a strong correlation with the clinical diagnoses ($R^2=0.89$, $p<0.00001$), with ROC analysis yielding an AUC of 0.99 (FIG. 23) and cross-validation through partition analysis resulting in only deminimus variance in the $R^2$ (FIG. 24). Tables 3 and 4, and FIGS. 25A-27, show various aspects of the resulting clinical comparison data for DDD-MRS vs. control diagnostic data, which data and comparisons are further described as follows.

TABLE 3

Comparison of Clinical DDD-MRS Results (MRS+/−) vs. Positive & Negative Controls, per Disc

|  | DDD-MRS Results Presumed TRUE | DDD-MRS Results Presumed FALSE | % Match |
|---|---|---|---|
| 3T Pain (All Discs) | 23 | 2 | 92.0% |
| 3T Pos Control (Pain, PD+) | 12 | 1 | 92.3% |
| 3T Neg Control (Pain, PD−) | 11 | 1 | 91.7% |
| 3T Neg Control (Asymptomatic) | 27 | 0 | 100.0% |
| 3T Neg Control (All, PD− + Asymptomatics) | 38 | 1 | 97.4% |
| 3T All | 50 | 2 | 96.2% |

TABLE 4

Comparison of Clinical DDD-MRS Results (MRS+/−) vs. Positive & Negative Controls, per Conventional Diagnostic Performance Measures: Sensitivity, Specificity, Positive Predictive Value (PPV), Negative Predictive Value (NPV), Global Performance Accuracy (GPA).

|  | DDD-MRS Diagnostic Performance |
|---|---|
| Sensitivity | 92.3% |
| Specificity | 97.4% |
| PPV | 92.3% |
| NPV | 97.4% |
| GPA | 96.2% |

Figure 25A:
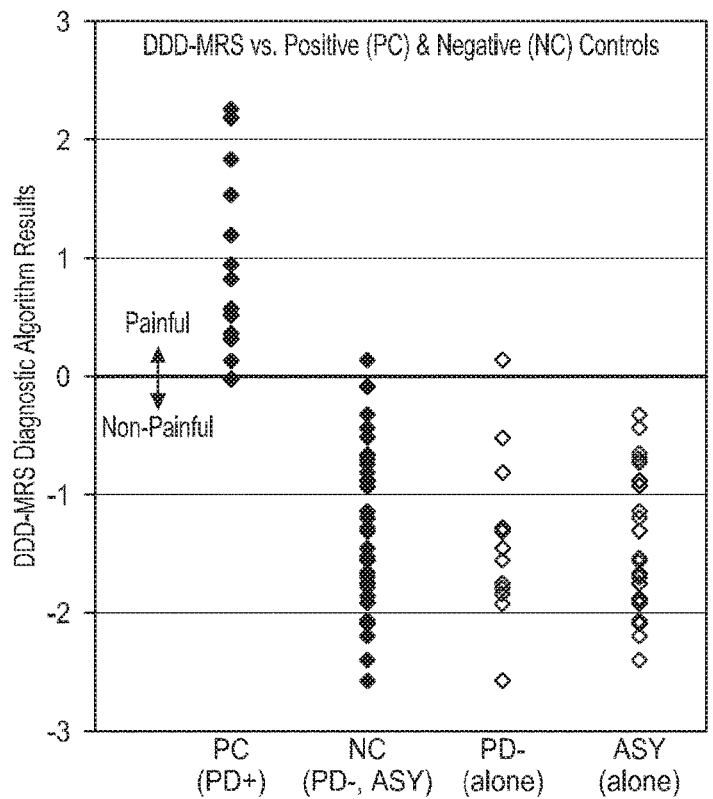
FIG. 25A shows a scatter plot histogram of DDD-MRS diagnostic results for each disc evaluated in the clinical study also addressed in FIGS. 22-24, and shows the DDD-MRS results separately for positive control (PC) discs (positive on provocative discography or "PD+"), negative control (NC) discs (negative on provocative discography or "PD−", plus discs from asymptomatic volunteers or "ASY"), PD− alone, and ASY alone.
Figure 25B:
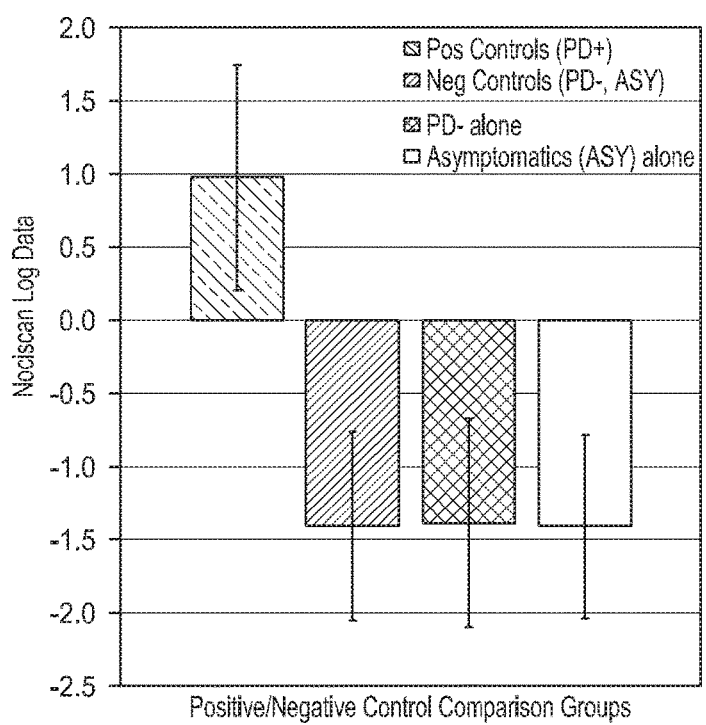
FIG. 25B shows a bar graph of the same DDD-MRS diagnostic results shown in FIG. 25A across the same subject groups, but shows the mean values with standard deviation error bars for the data.
Figure 26:
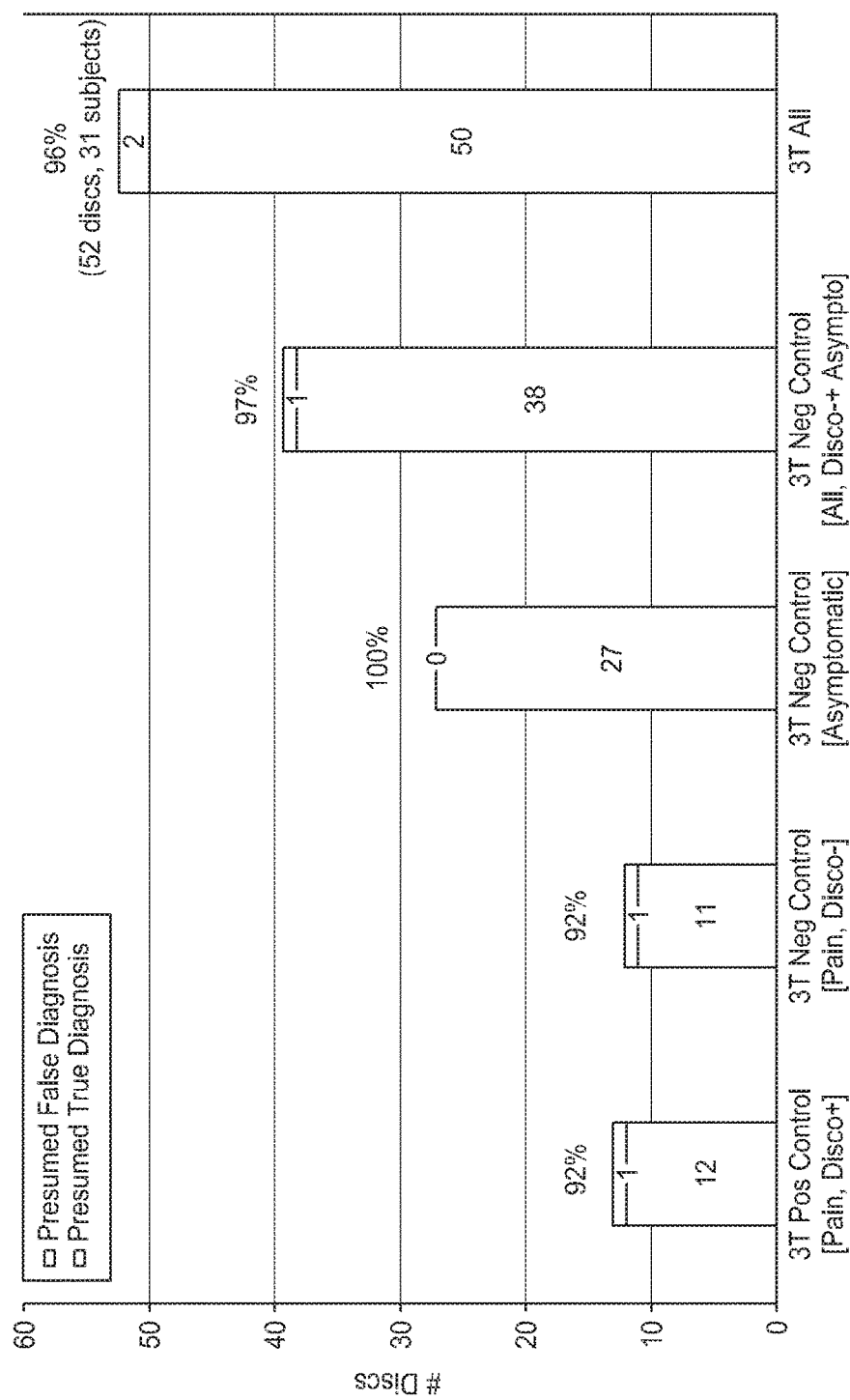
FIG. 26 shows a bar graph of presumed true and false binary "positive" and "negative" diagnostic results produced by the DDD-MRS system for painful and non-painful disc diagnoses in the clinical study, as compared against standard control diagnostic measures across the positive controls, negative controls (including sub-groups), and all discs evaluated in total in the study.
Figure 27:
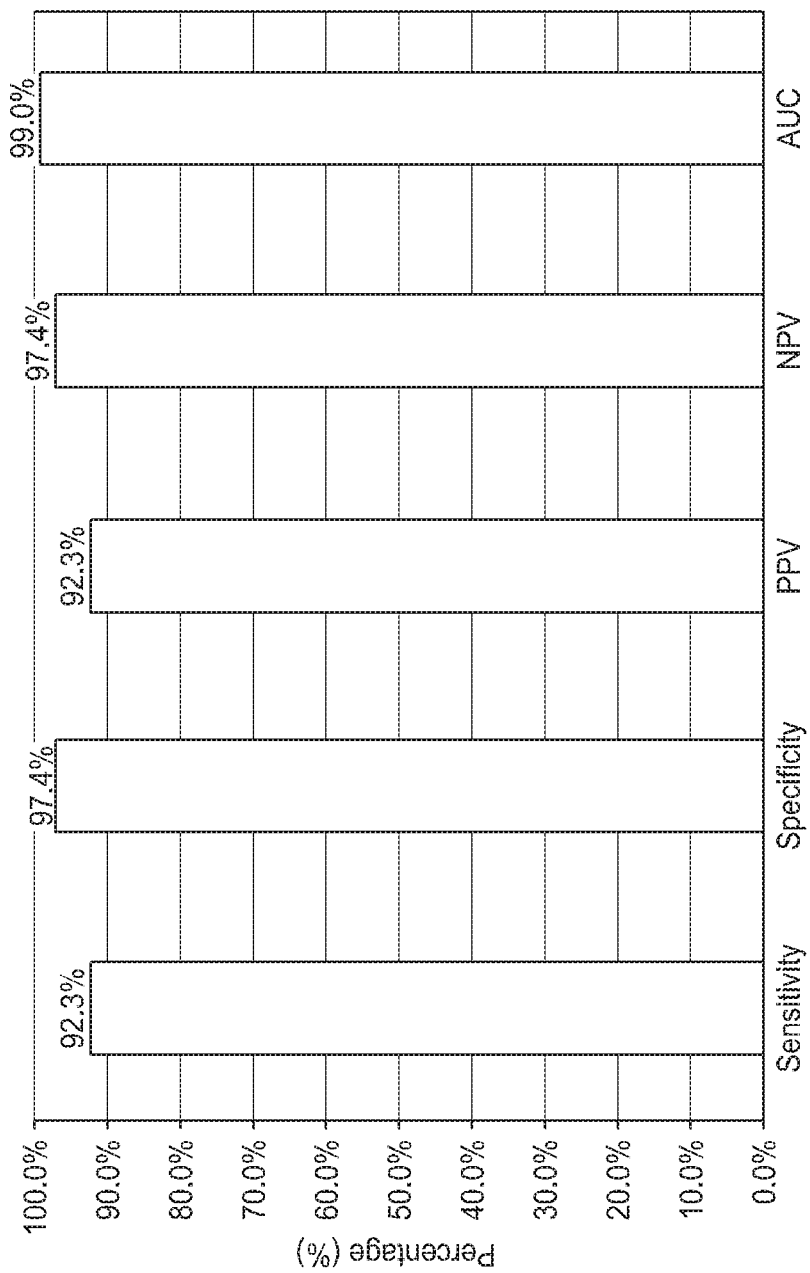
FIG. 27 shows diagnostic performance measures of Sensitivity, Specificity, Positive Predictive Value (PPV), Negative Predictive Value (NPV), and Global Performance Accuracy (GPA) for the DDD-MRS diagnostic results in the clinical study.

DDD-MRS results, with respect to binary MRS+ and MRS− diagnoses, correctly matched binary PC & NC diagnoses of painful/non-painful for 50/52 (96.2%) discs evaluated across the PD and ASY groups. Of the 13 MRS+ discs, 12 discs were from the PC group (PPV=92%). Of the 40 discs that were MRS−, 39 were from the NC group (NPV=97%). DDD-MRS sensitivity was about 92% and specificity was about 97%. Mean DDD-MRS results for the PC and NC groups were 0.97±0.77 and −1.40±0.65 (R2=0.89, p<0.00001, FIG. 1). DDD-MRS results matched PD results in 23/25 (92.0%) discs of the PD Group: 12/13 (96.2%) PD+ and 11/12 (91.7%) PD−. Mean DDD-MRS algorithm results for PD+ and PD− groups were 0.97±0.77 and −1.39±0.72 (p<0.00001). DDD-MRS results correlated with PD pain intensity scores ($R^2=0.73$). DDD-MRS results matched all 27/27 (100%) NC results represented by the ASY group. The mean DDD-MRS algorithm results for the ASY group were −1.4±0.63, which differed significantly vs. PD+ (p<0.0001), but were not significantly distinguishable vs. PD-results (p=0.46)(FIGS. 25A-B).

Figure 28:
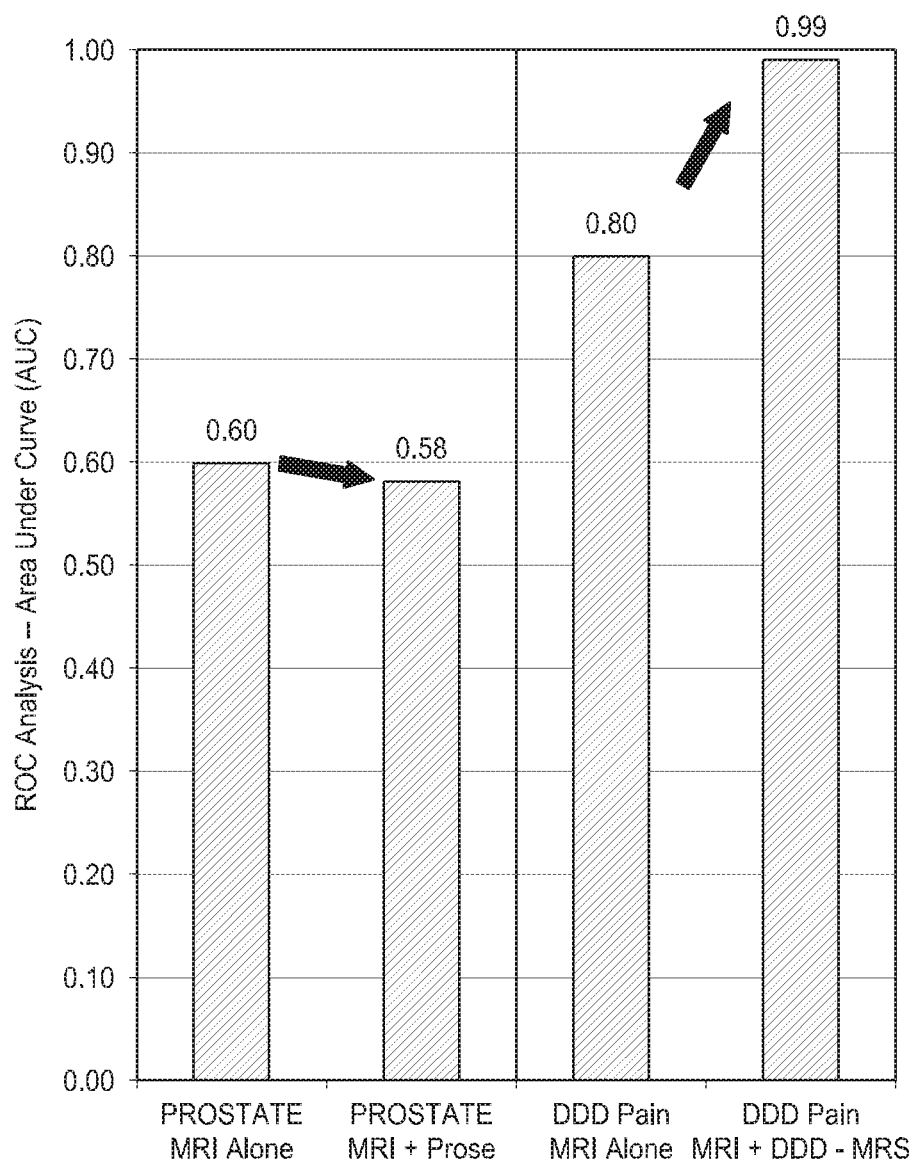
FIG. 28 shows a bar graph comparing areas under the curve (AUC) per ROC analysis of MRI alone (for prostate cancer diagnosis), MRI+PROSE (MRS package for prostate cancer diagnosis), MRI alone (for discogenic back pain or DDD pain), and MRI+DDD-MRS (for discogenic back pain or DDD pain), with bold arrows showing relative impact of PROSE vs. DDD-MRS on AUC vs. MRI alone for the respective different applications and indications.
Figure 29:
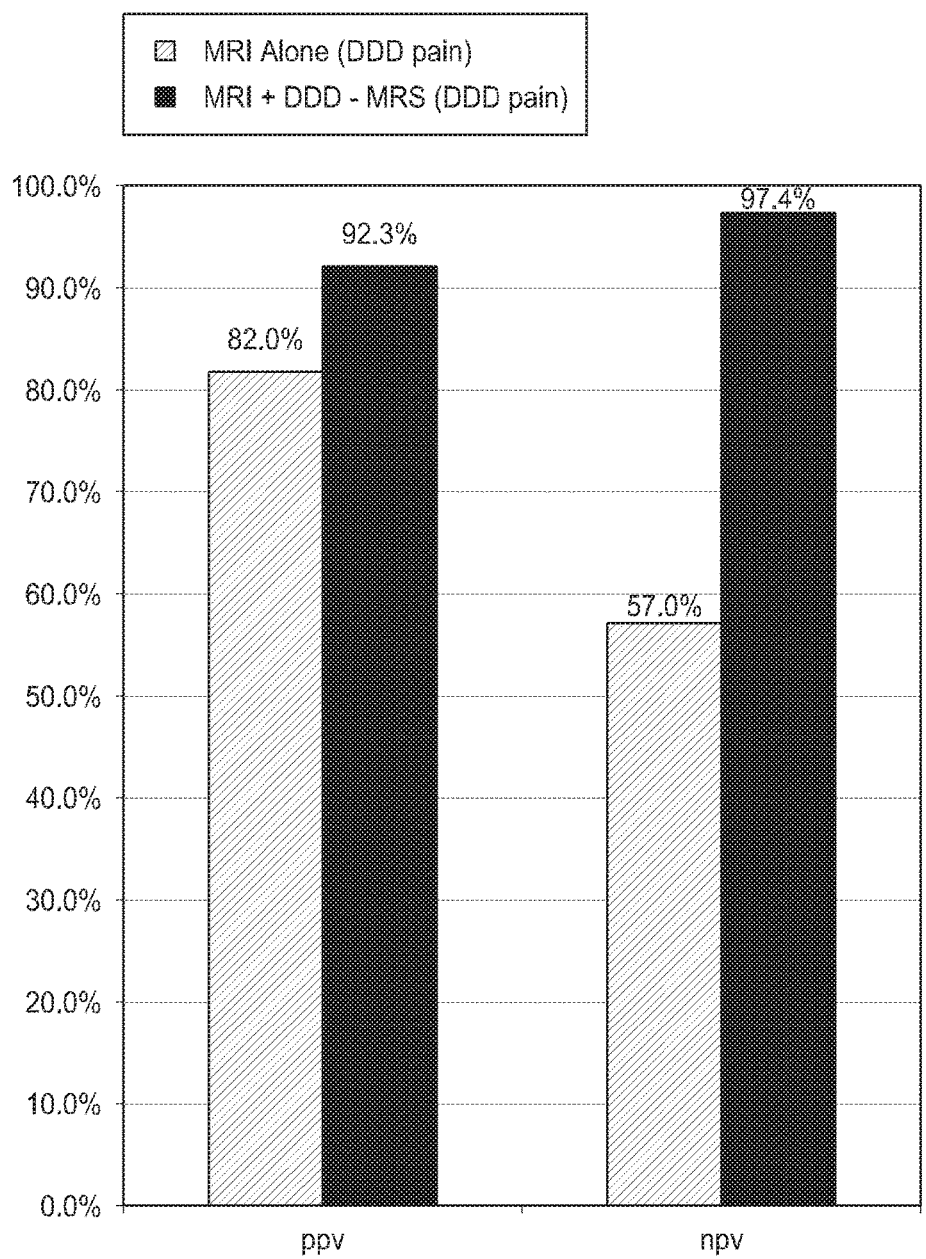
FIG. 29 shows PPV and NPV for MRI alone and MRI+DDD-MRS for diagnosing DDD pain, vs. standard control measures such as provocative discography.

As shown in FIGS. 28-29, the DDD-MRS results according to this study provided highly favorable improvement vs. the diagnostic accuracy typically attributed to MRI alone for diagnosing painful vs. non-painful DDD. More specifically, FIG. 28 (two bars on right side of graph) shows a comparison of the AUC for MRI alone vs. MRI+ DDD-MRS, per meta analysis of previously reported AUC data for MRI for this indication. This is further compared in the graph against a recent study reporting AUC for MRI alone vs. MRI+ PROSE for prostate cancer diagnosis (as compared to histopathological diagnosis of biopsy samples), where no improvement was shown by the additional inclusion of PROSE application of MRS within the MR-based diagnostic regimen. While the prostate data reflected within the graph reflects a larger relative population of samples in multi-center study, and the DDD-MRS pain diagnostic results shown reflects a smaller population within single center experience, the dramatic relative improvement presented by the DDD-MRS approach in the single center experience is expected to carry over to a significant degree into larger, multi-center context for this application. Further to FIG. 29, this additionally shows improvement to positive and negative predictive values by enhancing standard MRI alone with the addition of the DDD-MRS diagnostic—per meta analysis of the current data vs. previously published data for MRI for this purpose.

Certain benefits provided by the DDD-MRS processor for post-processing acquired MRS signals were also evaluated across a sub-set sampling of the DDD-MRS data derived from the clinical population under this study. In particular, for each series acquisition the SNR of the processed DDD-MRS signals ("DDD-MRS spectra/spectrum") was characterized, and compared against the 6 channel average, non-phase or frequency corrected, GE Signa output spectra as acquired "pre-processing" according to the present embodiments (e.g. "input combined spectra/spectrum"). This SNR characterization and comparison exercise was conducted as follows.

Figure 3:
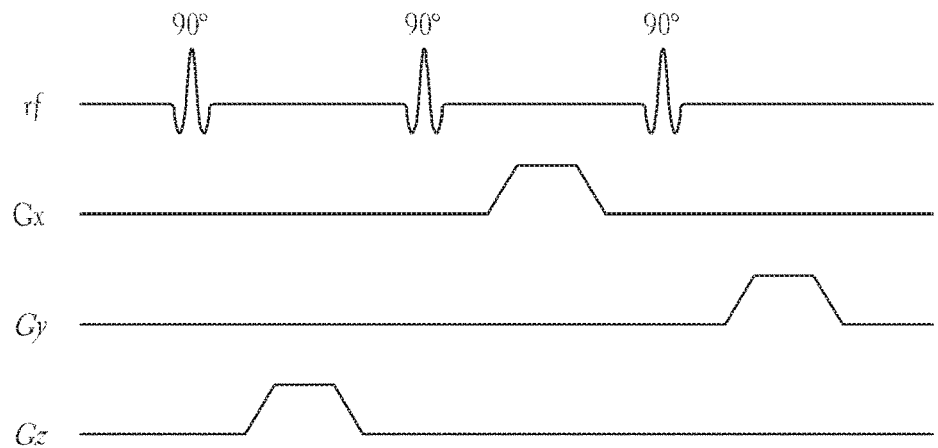
FIG. 3 shows an example of a CHESS water suppression pulse sequence diagram representing certain pulse sequence aspects contemplated by certain aspects of the present disclosure.
Figure 4:
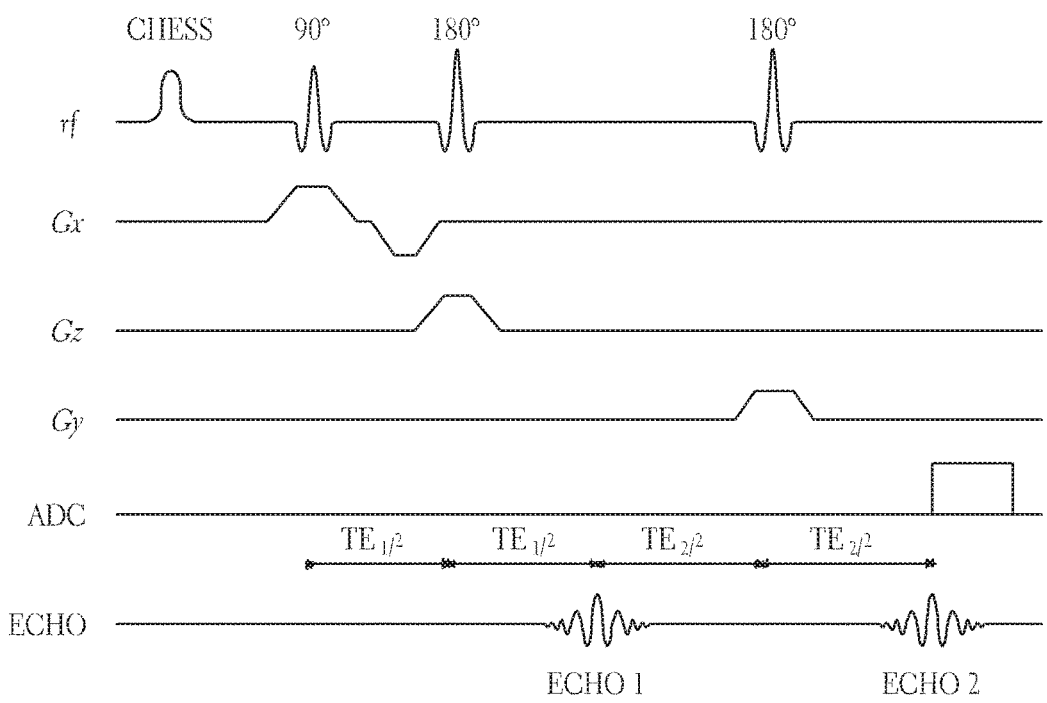
FIG. 4 shows various different aspects of an exemplary combined CHESS-PRESS pulse sequence diagram also consistent with certain aspects of the present disclosure.

A freeware digitization program (WinDIG™, Ver 2.5, copyright 1996, D. Lovy)) was used to digitize both final DDD-MRS results and "screen shot" images. The "screen shot" images were reverse-imaged using MS Paint prior to digitization. The output of the digitizer program is an array of integers in a CSV file format. The CSV data files were imported to Microsoft™ Excel™ and re-plotted as shown in FIGS. 3 and 4. A "region of interest" on the chemical shift (CS) axis (x-axis) pertaining to metabolite proteoglycan (PG, CS=2.11 PPM) was deemed to be the "signal". A region of interest to the far right (CS=0.5 PPM) which would not typically contain any spectral activity was deemed to be the "noise". In the event there was not a significant spectral peak in the PG region which is the often the case on pain patient discs, then the lactate/Lipid region of interest (CS=1.33 PP) was used as the signal. The "ranges of interest" were visually determined on both images resulting in sections of the data array. The SNR of a waveform is expressed as:

$$10*\log_{10}(RMS\ signal/RMS\ noise).$$

The RMS value was calculated by taking the sum of squares of the data section, calculating the mean of the sum of squares, and then taking the square root of the mean. Since the spectra are power amplitude plots, the log base 10 of the ratio of the RMS values is then multiplied by 10 to generate the SNR in dB.

Figure 30A:
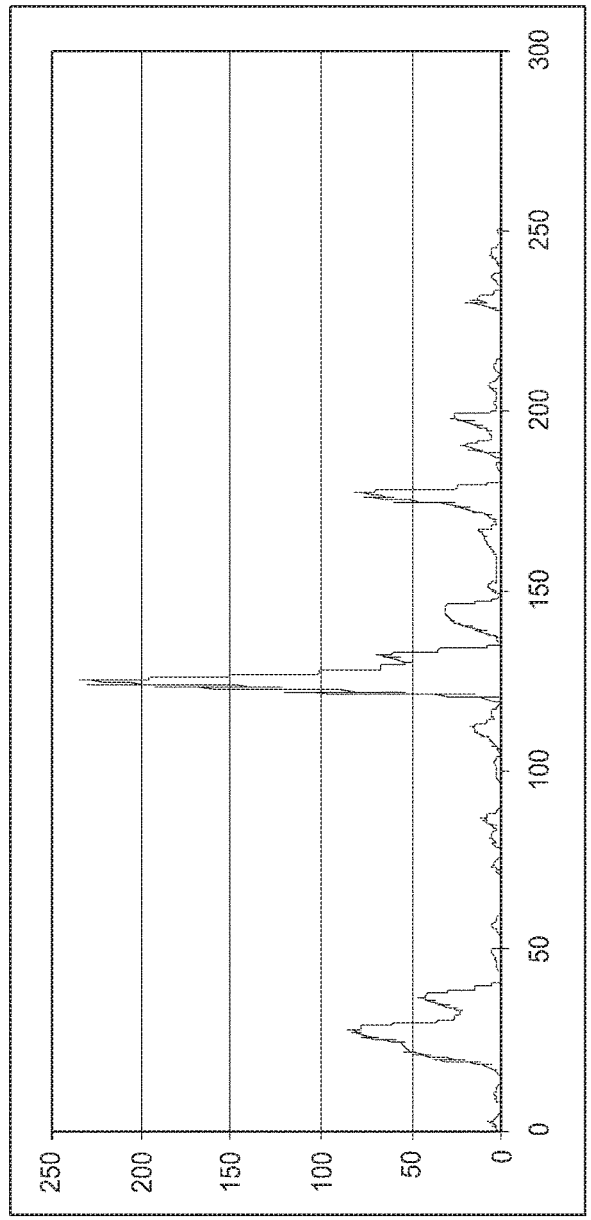
FIG. 30A shows a digitized post-processed DDD-MRS spectrum and certain calculated data derived therefrom as developed and used for calculated signal-to-noise ratio (SNR) of the processed result.
Figure 30B:
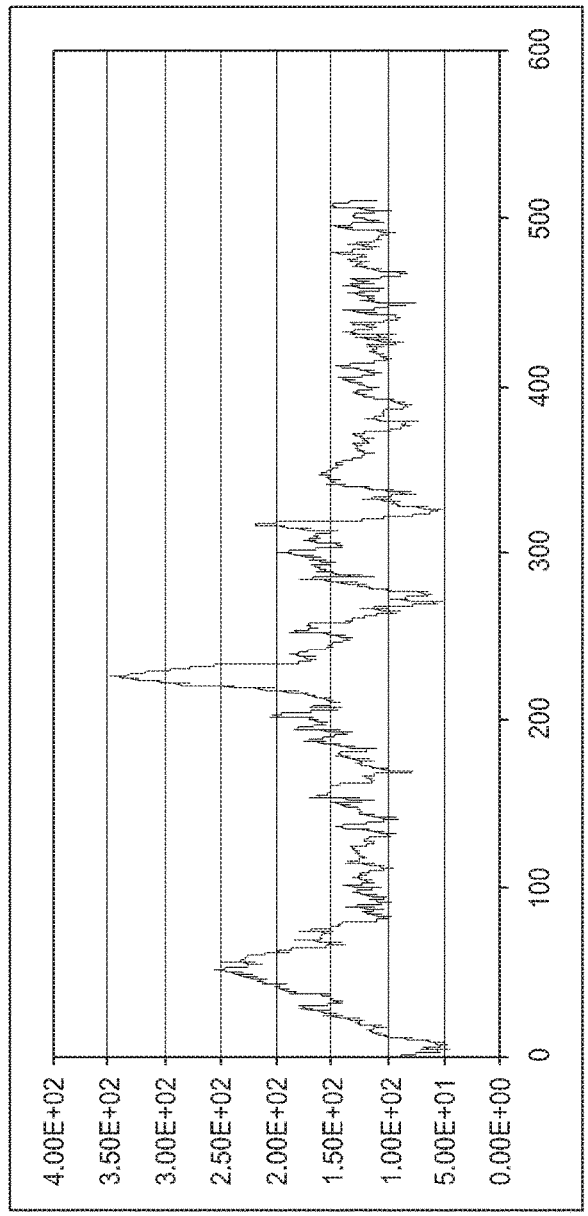
FIG. 30B shows a digitized pre-processed DDD-MRS spectrum and certain calculated data derived therefrom as developed and used for calculated signal-to-noise ratio (SNR) of the processed result.

For further understanding of this approach and examples of the digitized spectra and information extracted therefrom, FIG. 30A shows a digitized DDD-MRS spectral plot and accompanying SNR information, whereas FIG. 30B shows similar views for a digitized pre-processed channel averaged output spectral plot and related SNR information for the same acquisition series.

Figures 31A, 31B:
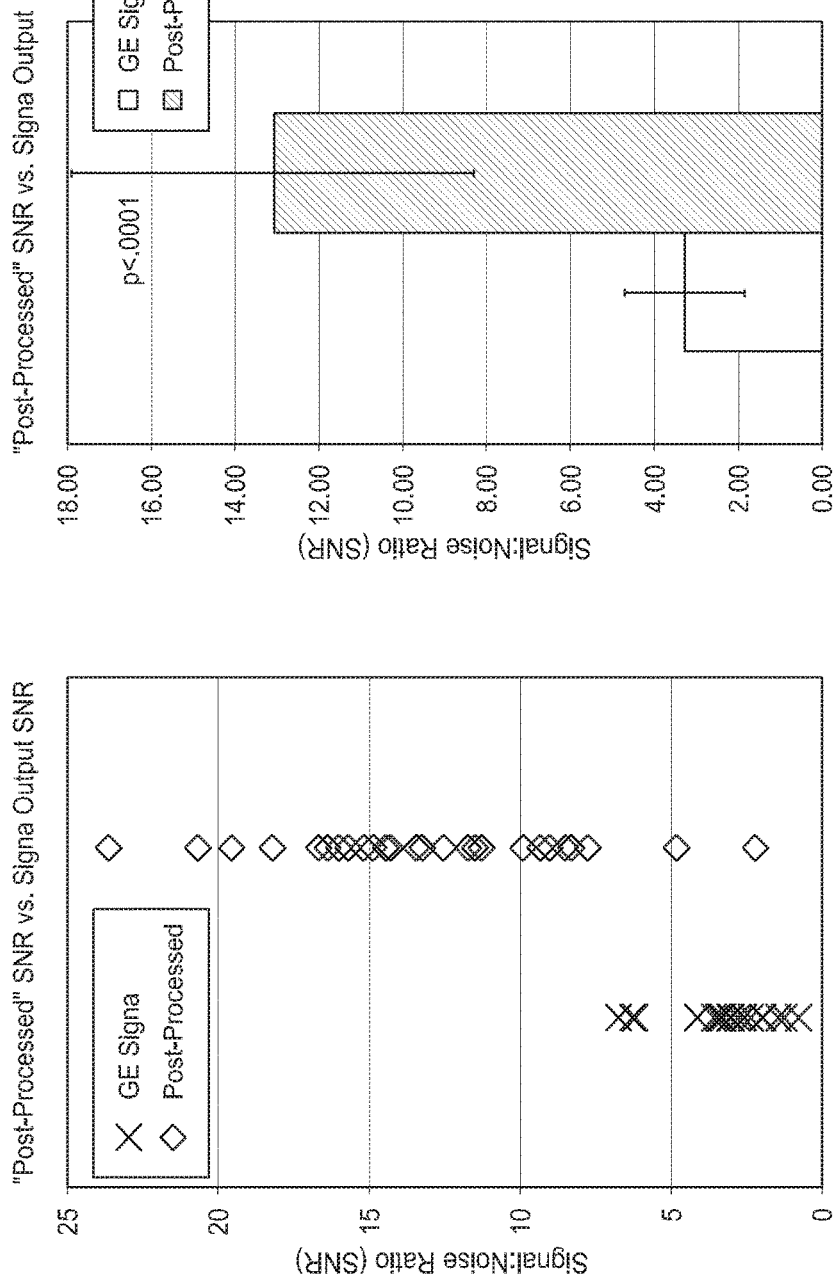
FIG. 31A shows a scatter plot histogram of signal-to-noise ratio (SNR) for standard "all channels, non-corrected" frame averaged MRS spectra produced by the GE Signa system for a subset of discs evaluated using the DDD-MRS pulse sequence in the clinical study, and the SNR for the same series acquisitions for the same discs post-processed by the DDD-MRS processor, as such SNR data was derived for example as illustrated in FIGS. 30A-B.
FIG. 31B shows the same data shown in FIG. 31A, but as bar graph showing mean values and standard deviation error bars for the data within each pre-processed and post-processed groups.
Figure 31D:
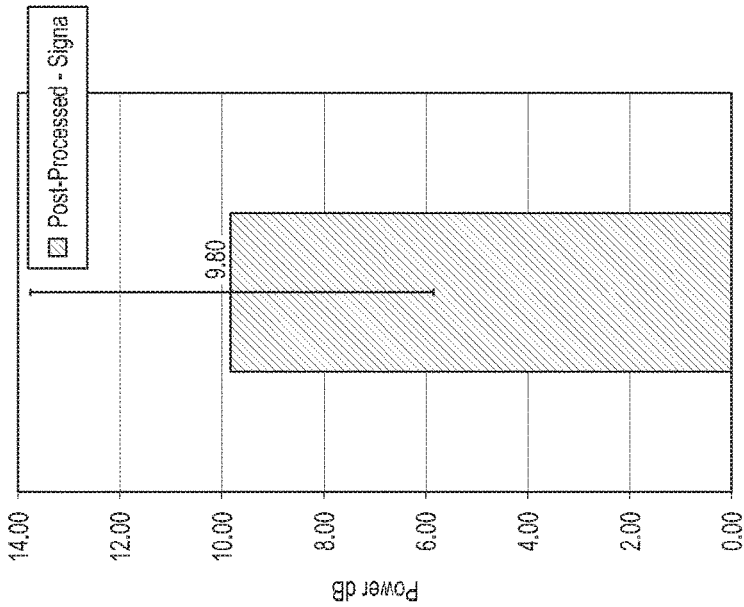
FIG. 31D shows a bar graph of mean value and standard deviation error bar of the absolute difference between post- and pre-processed SNR values for each of the discs shown in different views in FIGS. 31A-C.
Figure 31C:
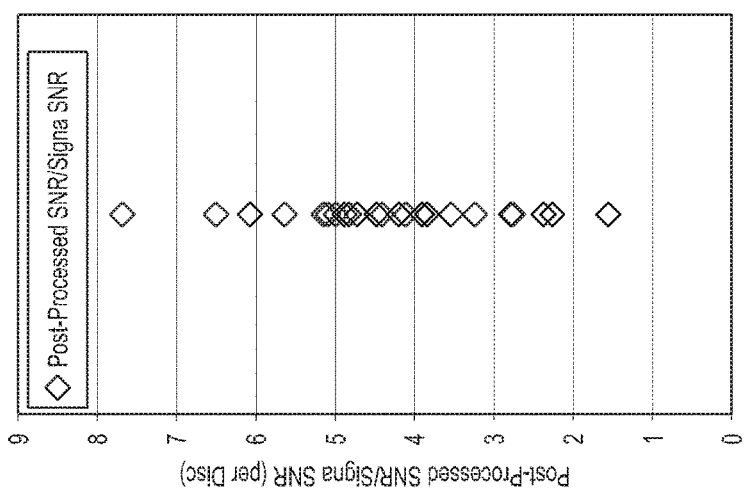
FIG. 31C shows a scatter plot histogram of the ratio of SNR values calculated post-versus pre-processing for each discs per the SNR data shown in FIGS. 31A-B.
Figures 31E, 31F:
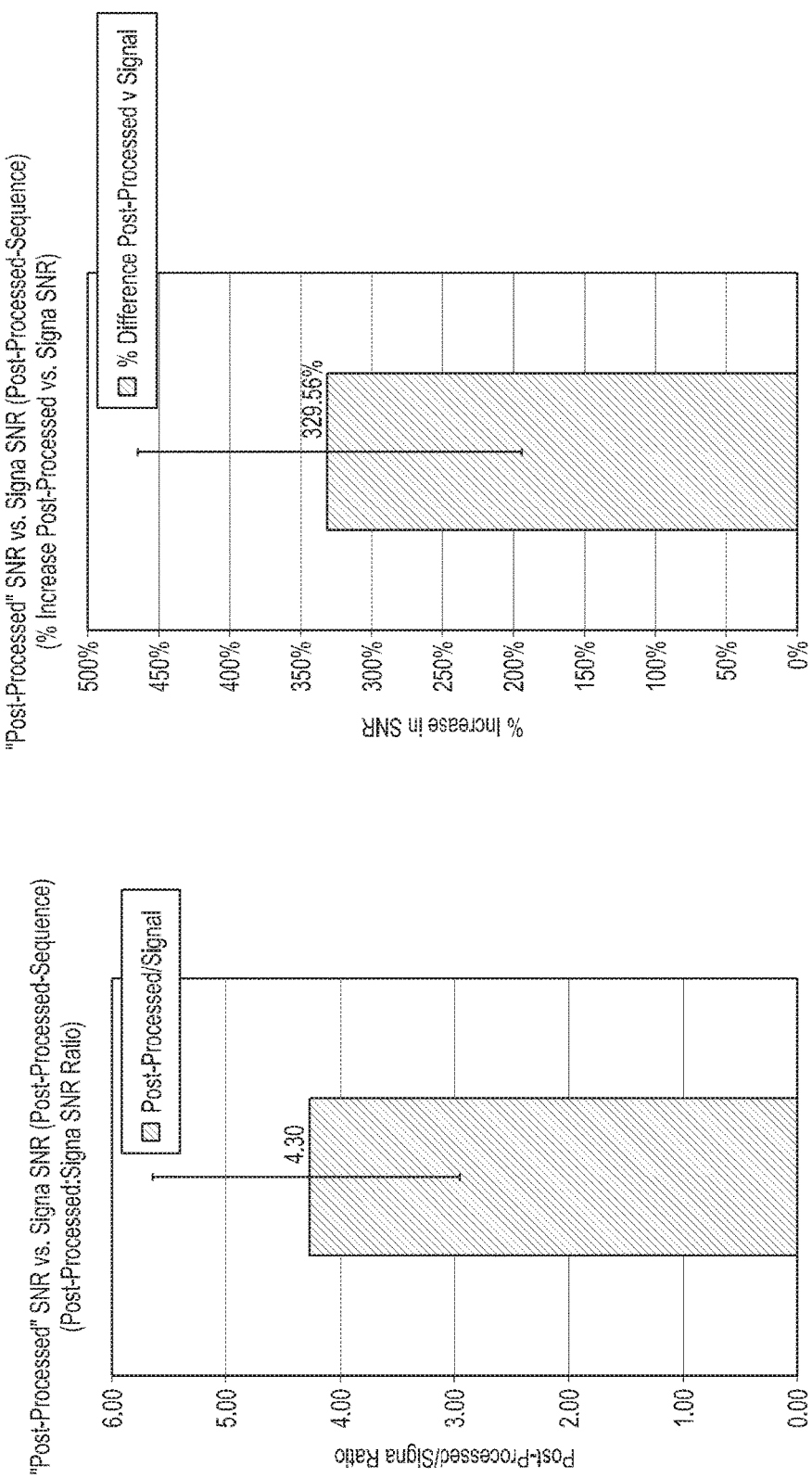
FIG. 31E shows a bar graph of mean value and standard deviation error bar of the ratio of post- to pre-processed SNR values for each of the discs shown in different views in FIGS. 31A-D.
FIG. 31F shows a bar graph of the mean value and standard deviation error bar for the percent increase in SNR from pre- to post-processed MRS spectra for each of the discs further featured in FIGS. 31A-D.

These pre- and post-processing SNR results are shown in FIGS. 31A-F. More specifically, FIG. 31A shows the calculated SNR for the pre- and post-processed spectra, with significant majority of the pre-processed spectral SNR shown on the left side histogram distribution of the plot falling below 5 (and also much of the data below 3), but with a significant majority of the post-processed spectral SNR shown on the right side histogram distribution of the plot falling above 3 (all but 1) and above 5 (all but just 2). A typical accepted SNR range for confidently measuring chemical constituents from an MRS plot is in many cases over 5, though in many cases may be for any data over 3—such that below these thresholds many believe the data interpretation should be "unquantifiable" or "immeasurable". In such an application of these thresholds, it is clear that a significant portion of data acquired pre-processing according to the present embodiments is not generally useful for interpretting signal regions of interest, whereas these data as post-processed hereunder become quite consistently useful. In fact, as shown in FIG. 31B, the average SNR across the signals evaluated for this comparison exercise was: about 3 (e.g. well below 5) pre-processing, and about 13 (e.g. well above 5) post-processing ($p<0.001$). As per the ratio of post- vs. pre-processed signals further shown in FIG. 31C, in all cases compared the post-processed signals were higher SNR than pre-processing, generally along a range between 2 to 8 times higher SNR (with only one point falling below 2× improvement, though still about 50% improved). As further shown in FIGS. 31D-F, the mean absolute improvement was about 10 dB, the mean ratio improvement was over 4×, and the mean % improvement was well over 300% in converting from pre- to post-processed signals according to the present embodiments.

Discussion:

The differentiation of painful and non-painful lumbar degenerative discs is an important goal in the accurate assessment of pain generators, and in guiding clinical management of patients with lumbar degenerative disc disease. The novel application of Magnetic Resonance Spectroscopy developed and evaluated under this study proposes a non-invasive, objective, and quantifiable measure of the chemical composition of the lumbar intervertebral disc. The MRS diagnostic algorithm developed and used in this study demonstrates a high degree of sensitivity in identifying patients with a clinical assessment of lumbar discogenic pain and a positive discogram, and a high degree of specificity in identifying levels that are not painful, without any false positive results observed in asymptomatics. This study developing, uniformly applying, and characterizing the DDD-MRS diagnostic approach retrospectively across the study population evaluated hereunder is quite encouraging. Cross validation also performed on the results predicts the approach is generalizable to broader population, as may be readily confirmed in additional prospective study in more subjects, as may be conducted by one of ordinary skill.

It is to be appreciated that the foregoing disclosure, including Example 1, provides various aspects that are highly beneficial, new advancements that enhance the ability to perform clinically relevant MRS-based examinations for diagnosing DDD pain. Each of these aspects, taken alone, is considered of independent value not requiring combination with other aspects hereunder disclosed. However, the combination of these aspects, and various sub-combinations apparent to one of ordinary skill, represent still further aspects of additional benefit and utility. The following are a few examples of these aspects, in addition to others noted elsewhere hereunder or otherwise apparent to one of ordinary skill, which aspects nonetheless not intended to be limiting to other aspects disclosed hereunder and are intended to be read in conjunction with the remaining disclosures provided elsewhere hereunder:

Channel Selection for Data Processing & Diagnosis:

Conventional MRI systems use multi-channel acquisition coils for spine detectors, which are pads that patients lye upon during a scan. GE Signa uses an 8 channel acquisition coil array, of which 6 channels are typically activated for use for lumbar spine imaging & diagnosis (including for MRS). However, the system generally combines all data from these channels in producing a single "averaged" curve. For single voxel MRS, this has been determined to be highly inefficient and significant source of error in the data, in particular reducing signal-to-noise ratio. The channels vary in their geographical placement relative to lumbar discs, and are believed to be at least one source of variability between them regarding acquired signal quality for a given disc. Of the six channels, most frequently at least one of the channels is clearly "poor" data (e.g. poor signal-to-noise), and often this can mean 2 to 5 of those channels being clearly degraded vs. one or more "strong" channels. Accordingly, the present disclosure contemplates that comparing the channels, and using only the "strongest" channel(s), significantly improves signal quality and thus data acquired and processed in performing a diagnosis. This "channel isolation/selection" is considered uniquely beneficial to the DDD pain application contemplated hereunder, and can be done manually as contemplated hereunder, though the present disclosure also includes automating this operation to compare and choose amongst the channels for a given voxel scan via an automated DDD-MRS signal processor disclosed.

"Coherent" Averaging within & between Channels:

During a single voxel scan, many repetitions are performed that are later used for averaging in order to reduce noise and increase signal-to-noise ratio in an acquired MRS spectrum. This can range from about 100 repetitions to about 600 or more, though more typically may be between about 200 to about 500, and still more frequently between about 300 to about 400, and according to one specific exemplary embodiment frequently included in the physical embodiments evaluated in the clinical study of Example 1 may be about 384 repetitions. With a TR of 1 to 2 seconds for example, this can range from less than 5 to 10 minutes time.

However, a "shift" in phase and frequency has been observed among the acquired data over these repetitions. The current standard MRI system configurations, via certain sequence routines, do not correct for such shifts. Thus when these repetitions are averaged the result becomes "blurred" with reduced signal amplitude relative to noise, as well as possibility for signal "broadening" or separation into multiple peaks from what should be otherwise a single, more narrow band peak.

In addition or alternative to "strongest" channel selection for processing, significant benefit and utility is contemplated hereunder for correcting for one or both of these phase and/or frequency "shifts" among the repetitions of an acquisition series acquired at a channel during a single voxel scan. The observed results of such processing have been higher signal quality, with higher signal-to-noise ratio, and/or more narrow defined signals at bands of interest to spectral regions associated with chemicals believed (and correlated) to be relevant for diagnosing disc pain (e.g., PG and/or LA and/or AL). It is noted, and relevant to various of the detailed embodiments disclosed hereunder, that the spectral peak region associated with water is typically the most prominent and highest amplitude signal across the spectrum. This peak and its location relative to a baseline is used according to certain of the present embodiments to define a given shift in a signal, and thus that shift at the water region is used to correct the entire spectral signal back to a defined baseline. As water peak shifts, or conversely is corrected, so does the rest of the spectrum including the target chemical markers relevant to conducting diagnoses.

This degree and location of the water peak may also be used to determine and edit acquisition frames which are sufficiently abnormally biased relative to the other acquisition frames to adversely impact spectral data (or unable to "grab and shift"), e.g. frame editing according to further embodiments.

Where water is not as prominent, e.g. highly desiccated discs with over suppressed water in the sequence, other reliably prominent and recognizable peaks maybe identified used for similar purpose (e.g. peaks within the PG and/or LA and/or AL regions themselves). However, due to its typical prominence and many benefits of using the water peak for these various signal processing purposes, novel approaches and settings for water suppression are contemplated and disclosed hereunder. This provides for a water signal, either manually or automatically, within an amplitude range that is sufficient to locate and "grab" for processing, but not so extensive to "washout" lower chemical signatures in an inappropriate dynamic range built around the higher water signal. The result of corrections contemplated hereunder aligns the repetitions to phase and/or frequency coherence, and thus the resulting averaging achieved is desirably more "coherent" averaging. It is further contemplated that these shifts may be observed and corrected in either time or frequency domain (esp. re: frequency shift), and while certain exemplary embodiments are described hereunder in detail corrections yielding similarly improved results may be made in either domain (again esp. re: frequency coherent correction).

DDD-MRS Factors, Criteria & Thresholds for Diagnostic Results

The present disclosure provides an empirically derived relationship between four weighted factors that involve data derived from three regions of MRS spectra acquired from discs that are generally associated with three different chemicals, namely PG, LA, and AL. Other support exists to suspect these identified chemicals may be active culprits in disc pain, e.g. reducing PG, and increasing LA and AL, as factored in the diagnostic relationship developed and applied hereunder. More directly, at least a sub-set of these factors used in this diagnostic developed relationship have been directly correlated to disc pain (e.g. PG/LA ratio per prior 11T studies performed ex vivo). These factors are further addressed in view of further supporting literature and disclosures, which are believed to support their correlation to pain, as follows.

The normal intervertbral disc is avascular and disc cells function under anaerobic conditions. (Ishihara and Urban 1999; Grunhagen, Wilde et al. 2006) Anaerobic metabolism, such as in the setting of oxygen deprivation and hypoxia, causes lactate production. (Barte/s, Fairbank et al. 1998; Urban, Smith et al. 2004) Disc pH is proportional to lactate concentration. (Diamant, Karlsson et al. 1968) Lactic acid produces pain via acid sensing ion channels on nociceptors. (Immke and McCleskey 2001; Sutherland, Benson et al. 2001; Molliver, Immke et al. 2005; Naves and McCleskey 2005; Rukwied, Chizh et al. 2007) Disc acidity has been correlated with pre-operative back pain. (Diamant, Karlsson et al. 1968; Nachemson 1969; Keshari, Lotz et al. 2008)

Proteoglycan content within the nucleus pulposus, which is the primary matrix which holds water in the disc nucleus, decreases with disc degeneration, which is also associate with dehydration e.g. via "darkened" disc nuclei seen on T2 MRI. (Roughley, Alini et al. 2002; Keshari, Lotz et al. 2005; Keshari, Zektzer et al. 2005; Roberts, Evans et al. 2006) Chondroitin sulfate proteoglycans inhibit nerve ingrowth. (Zuo, Hernandez et al. 1998; Zuo, Neubauer et al. 1998; Jones, Sajed et al. 2003; Properzi, Asher et al. 2003; Jain, Brady-Kalnay et al. 2004; Klapka and Muller 2006) Nerve ingrowth is increased in degenerative painful discs. (Brown, Hukkanen et al. 1997; Coppes, Marani et al. 1997; Freemont, Peacock et al. 1997; Freemont, Watkins et al. 2002)

Discography is the current gold-standard of diagnostic care for differentiating painful discs, but is controversial due to being: invasive, painful, subjective, technique/operator dependent, frequently challenged due to high false positive rates (principally as indicated in studies with asymptomatic volunteers), and risky to the patient. (Carragee and Alamin 2001; Guyer and Ohnmeiss 2003; O'Neill and Kurgansky 2004; Cohen, Larkin et al. 2005; Carragee, Alamin et al. 2006; Carragee, Lincoln et al. 2006; Buenaventura, Shah et al. 2007; Wichman 2007; Derby, Baker et al. 2008; Scuderi, Brusovanik et al. 2008; Wolfer, Derby et al. 2008) The prevailing modern guidelines for performing discography generally require concordant pain intensity scores equal to or above 6 (on increasing scale of 0-10), provocation pressures of no more than 50 psi above opening pressure, and another negative control disc in order to determine a "positive discogram" result for a disc. This modern technique has been most recently alleged to provide a higher specificity (e.g. lower false positive) rates than previously alleged in other studies. (Wolfer et al., SPINE 2008) However, notwitsthanding this potential improvement with modern techniques in the test's accuracy, a more recent published study has shown the invasive needle puncture of discography significantly increases disc degeneration and herniations rates. Further to this disclosure, these adverse affects of the discography needle puncture in the "negative control discs" have been alleged as possible culprit in adjacent level disc disease that often affects adverse outcomes following surgical treatments removing the "positive discogram" discs (e.g. fusion and/or disc arthroplasty).

Proteoglycan and lactate within discs have unique MR signatures that can be identified and objectively measured using MR Spectroscopy, and a calculated ratio based on these measures significantly differentiates painful from non-painful discs. (Keshari, Lotz et al. 2008) DDD-MRS approaches, as disclosed hereunder, can non-invasively, painlessly, and objectively measure and quantify proteoglycan and lactate-related signatures of intervertebral discs in vivo using a novel software upgrade to commercially available MRI systems, and a novel diagnostic algorithm based at least in part upon these in vivo measures reliably distinguishes painful vs. non-painful discs with a lower false positive rate predicted versus discography.

The following publications are herein incorporated in their entirety by reference thereto, and provide at least in part a bibliography of certain disclosures referenced above and otherwise elsewhere hereunder:

Bartels, E. M., J. C. Fairbank, et al. (1998). "Oxygen and lactate concentrations measured in vivo in the intervertebral discs of patients with scoliosis and back pain." *Spine* 23(1): 1-7; discussion 8.

Brown, M. F., M. V. Hukkanen, et al. (1997). "Sensory and sympathetic innervation of the vertebral endplate in patients with degenerative disc disease." *J Bone Joint Surg Br* 79(1): 147-53.

Buenaventura, R. M., R. V. Shah, et al. (2007). "Systematic review of discography as a diagnostic test for spinal pain: an update." *Pain Physician* 10(1): 147-64.

Carragee, E. J. and T. F. Alamin (2001). "Discography. a review." *Spine J* 1(5): 364-72.

Carragee, E. J., T. F. Alamin, et al. (2006). "Low-pressure positive Discography in subjects asymptomatic of significant low back pain illness." *Spine* 31(5): 505-9.

Carragee, E. J., T. Lincoln, et al. (2006). "A gold standard evaluation of the "discogenic pain" diagnosis as determined by provocative discography." *Spine* 31(18): 2115-23.

Cohen, S. P., T. M. Larkin, et al. (2005). "Lumbar discography: a comprehensive review of outcome studies, diagnostic accuracy, and principles." *Reg Anesth Pain Med* 30(2): 163-83.

Coppes, M. H., E. Marani, et al. (1997). "Innervation of "painful" lumbar discs." *Spine* 22(20): 2342-9; discussion 2349-50.

Derby, R., R. M. Baker, et al. (2008). "Analgesic Discography: Can Analgesic Testing Identify a Painful Disc?" *SpineLine* (November-December): 17-24.

Diamant, B., J. Karlsson, et al. (1968). "Correlation between lactate levels and pH in discs of patients with lumbar rhizopathies." *Experientia* 24(12): 1195-6.

Freemont, A. J., T. E. Peacock, et al. (1997). "Nerve ingrowth into diseased intervertebral disc in chronic back pain." *Lancet* 350(9072): 178-81.

Freemont, A. J., A. Watkins, et al. (2002). "Nerve growth factor expression and innervation of the painful intervertebral disc." *J Pathol* 197(3): 286-92.

Grunhagen, T., G. Wilde, et al. (2006). "Nutrient supply and intervertebral disc metabolism." *J Bone Joint Surg Am* 88 Suppl 2: 30-5.

Guyer, R. D. and D. D. Ohnmeiss (2003). "Lumbar discography." *Spine J* 3(3 Suppl): 11S-27S.

Immke, D. C. and E. W. McCleskey (2001). "Lactate enhances the acid-sensing Na+ channel on ischemia-sensing neurons." *Nat Neurosci* 4(9): 869-70.

Ishihara, H. and J. P. Urban (1999). "Effects of low oxygen concentrations and metabolic inhibitors on proteoglycan and protein synthesis rates in the intervertebral disc." *J Orthop Res* 17(6): 829-35.

Jain, A., S. M. Brady-Kalnay, et al. (2004). "Modulation of Rho GTPase activity alleviates chondroitin sulfate proteoglycan-dependent inhibition of neurite extension." *J Neurosci Res* 77(2): 299-307.

Jones, L. L., D. Sajed, et al. (2003). "Axonal regeneration through regions of chondroitin sulfate proteoglycan deposition after spinal cord injury: a balance of permissiveness and inhibition." *J Neurosci* 23(28): 9276-88.

Keshari, K. R., J. C. Lotz, et al. (2005). "Correlation of HR-MAS spectroscopy derived metabolite concentrations with collagen and proteoglycan levels and Thompson grade in the degenerative disc." *Spine* 30(23): 2683-8.

Keshari, K. R., J. C. Lotz, et al. (2008). "Lactic acid and proteoglycans as metabolic markers for discogenic back pain." *Spine* 33(3): 312-317.

Keshari, K. R., A. S. Zektzer, et al. (2005). "Characterization of intervertebral disc degeneration by high-resolution magic angle spinning (HR-MAS) spectroscopy." *Magn Reson Med* 53(3): 519-27.

Klapka, N. and H. W. Muller (2006). "Collagen matrix in spinal cord injury." *J Neurotrauma* 23(3-4): 422-35.

Molliver, D. C., D. C. Immke, et al. (2005). "ASIC3, an acid-sensing ion channel, is expressed in metaboreceptive sensory neurons." *Mol Pain* 1: 35.

Nachemson, A. (1969). "Intradiscal measurements of pH in patients with lumbar rhizopathies." *Acta Orthop Scand* 40(1): 23-42.

Naves, L. A. and E. W. McCleskey (2005). "An acid-sensing ion channel that detects ischemic pain." *Braz J Med Biol Res* 38(11): 1561-9.

O'Neill, C. and M. Kurgansky (2004). "Subgroups of positive discs on discography." *Spine* 29(19): 2134-9.

Properzi, F., R. A. Asher, et al. (2003). "Chondroitin sulphate proteoglycans in the central nervous system: changes and synthesis after injury." *Biochem Soc Trans* 31(2): 335-6.

Roberts, S., H. Evans, et al. (2006). "Histology and pathology of the human intervertebral disc." *J Bone Joint Surg Am* 88 Suppl 2: 10-4.

Roughley, P. J., M. Alini, et al. (2002). "The role of proteoglycans in aging, degeneration and repair of the intervertebral disc." *Biochem Soc Trans* 30(Pt 6): 869-74.

Rukwied, R., B. A. Chizh, et al. (2007). "Potentiation of nociceptive responses to low pH injections in humans by prostaglandin E2." *J Pain* 8(5): 443-51.

Scuderi, G. J., G. V. Brusovanik, et al. (2008). "A critical evaluation of discography in patients with lumbar intervertebral disc disease." *Spine J* 8(4): 624-9.

Sutherland, S. P., C. J. Benson, et al. (2001). "Acid-sensing ion channel 3 matches the acid-gated current in cardiac ischemia-sensing neurons." *Proc Natl Acad Sci USA* 98(2): 711-6.

Urban, J. P., S. Smith, et al. (2004). "Nutrition of the intervertebral disc." *Spine* 29(23): 2700-9.

Wichman, H. J. (2007). "Discography: over 50 years of controversy." *Wmj* 106(1): 27-9.

Wolfer, L. R., R. Derby, et al. (2008). "Systematic review of lumbar provocation discography in asymptomatic subjects with a meta-analysis of false-positive rates." *Pain Physician* 11(4): 513-38.

Zuo, J., Y. J. Hernandez, et al. (1998). "Chondroitin sulfate proteoglycan with neurite-inhibiting activity is up-regulated following peripheral nerve injury." *J Neurobiol* 34(1): 41-54.

Zuo, J., D. Neubauer, et al. (1998). "Degradation of chondroitin sulfate proteoglycan enhances the neurite-promoting potential of spinal cord tissue." *Exp Neurol* 154(2): 654-62.

Notwithstanding the foregoing, it is to be appreciated that despite the support for suspecting these chemicals as the cause of pain, and despite the belief that these chemicals are measured and represented at least in part by the data derived from the MRS data acquired, this correlation need not be accurate in order for the data and diagnostic algorithm & approach presented hereunder to remain valid and highly useful.

In particular regard to MRS data derived from regions associated with LA and AL, these are quite narrowly defined ranges closely adjacent to each other, and also overlap with a much broader band associated with lipid. Accordingly, the data acquired from these two "bins" may blur between the actual two chemical sources. However, as they both relate to and are a product of abnormal cellular metabolism and hypoxia, their combination may be fairly considered a signature region more broadly for "abnormal cellular metabolism/hypoxia." Furthermore, lipid contribution may bias measurements in this region, and as lipid is a high molecular weight molecule if present the signal is typically strong and often may wash out resolution of either or both of LA or AL-based signal in the region. However, in the current experience with DDD-MRS, even where lipid signal is believed present, and even in significant degree, the acquired data intended to represent LA and AL as processed through the diagnostic algorithm and processor has not produced a false result against controls (e.g. remains an accurate result). When this happens, the diagnostic result is consistently MRS+ indicating a positive result for pain in the suspect disc. However, such lipid-related positive results occur most frequently in L5-S1 discs that are associated with a particular degenerative profile and morphology that is more reliably diagnosed as painful on MRI alone (and consistently confirmed as such via PD).

To the extent the measurements derived from the MRS "regions" believed to be associated with these chemicals, and as used in the weighted factor diagnostic algorithm developed, are applied uniformly across the different control disc populations, the diagnostic accuracy of the result prevails in the ultimate comparison data—regardless of the source of the MRS data acquired. Accordingly, the benefit and utility of the diagnostic approach is defined ultimately by its diagnostic results, and not intended to be necessarily limited and defined only by the theory as to what the underlying sources of the measured signatures are.

Conversely, it is also further contemplated and to be understood that the present disclosure provides a specific diagnostic relationship algorithm that produces a particular range of diagnostic results that compare with high correlation with control measures for pain/non-pain in discs evaluated. However, this is the result of statistically generated correlation and retrospective approach to data fitting. While appropriate for diagnostic algorithm development and the specific result disclosed hereunder is considered highly beneficial, this may migrate to other specific algorithms that may be more preferred though without departing from the broad scope intended for the various aspects of this disclosure. Such modifications may be the result of further data processing across more samples, for example, and may affect the "weighting" multipliers associated with each factor used in the algorithm, or which factors are featured in the algorithm, or which regions or features of the MRS spectra are even used as the signatures from which data is derived and used in the algorithm.

It is contemplated that while the DDD-MRS diagnostic processor hereunder disclosed and diagnostic results provided therefrom, as disclosed in context of clinical data presented under Example 1, provide binary MRS+ and MRS− results for severe pain & absence of severe pain in discs, respectively. However, the results are also quantified along a scaled range which may be appropriately interpreted by a diagnostician as "levels" of relevance along the pain/non-pain range. Such interpretation may impact the direction of pain management decisions, such as which discs to treat, how to treat, or not to treat at all. Moreover, while the current diagnostic embodiments have been described by reference to site specific location of pain source at reference disc(s), diagnostic value may be more generalized to confirmed presence or absence of any painful disc at all. Such may impact more general management decision, such as administration or avoidance of pain medication.

Furthermore, in still further embodiments, the diagnostic results may be provided in different forms than as described by the specific embodiments disclosed by reference to Example 1. For example, binary definitive diagnoses of MRS+ and MRS− may be supplemented with "indeterminate" as a third category. This may, for example, represent a result of applying certain threshold criteria that must be met in order to make a definitive +/− determination. Such criteria may include, for example, SNR threshold of the underlying post-processed DDD-MRS spectrum from which the diagnostic data is extracted for performing the diagnoses. In another example, a defined proximity of calculated diagnostic results from the DDD-MRS diagnostic processor to the zero (0) median threshold between MRS+ and MRS− diagnoses may represent a threshold under which definitive MRS+/− determination is not decidedly made by the processor.

It is also to be further appreciated that the pulse sequence platform approach, and/or specific parameter settings, and/or signal processing approaches (and/or parameter or threshold criteria settings), may be modified. Such modifications may affect resulting spectra (and data extracted therefrom) sufficiently to redistribute the regional data used for diagnostic purposes, and may thus motivate or necessitate a re-evaluation and re-formation of the diagnostic algorithm that is appropriate for data acquired and/or processed under those modified approaches. Accordingly, while the present interactions between these component parts of an overall DDD-MRS system, and results, are considered of particular benefit for forward application in clinical use, such further modifications are also considered to fall within the broad scope of the aspects disclosed hereunder, and may represent for example a consequence of further development and experience as would be apparent to one of ordinary skill (though such further modifications may also provide still further benefit).

L5-S1 & Novel Detection Coils:

The L5-S1 disc is typically oriented at an oblique angle relative to other lumbar discs, and has unique shape that in many circumstances challenges the ability to prescribe voxel for adequate DDD-MRS data acquisition. The current voxelation plan for MRS generally requires a three-dimensional "cube" of space to be defined as the voxel (a pixel with volume), typically done by an operator technician on overlay to MRI images of the region. However, for this angled L5-S1 disc, the voxel volume may be maximized by angling the voxel to match the angulated disc. However, such angled voxels at this location have been observed to relate to degraded data acquisition by existing spine detector coils. Accordingly, a custom spine coil is further contemplated that angles at least one coil channel to either a pre-determined angle more representative of typical L5-S1 discs, or a range of angles may be provided my multiple such coils in a kit, or the coil channel may be given an "adjustable" angle to meet a given anatomy. Furthermore, software may be adapted to identify an angled voxel and modify the coordinate system assigned for sequence and/or multi-channel acquisition in order better acquire data from an angled voxel (e.g. where planar slices are taken through the voxel as data acquired, the planar coordinates are revised into an adjusted coordinate system that accounts for the angulation relative to the data acquisition at the channel(s)). This uniquely angled disc level is also associated with and located within a radiused curvature at the small of the back, which may be more extreme in some patients than others. While simply adjusting the angle of lower detection channel coils may improve acquisition here, further more dramatic variations are also contemplated. In one such further aspect, a detector coil array is created with smaller coils, and/or on a flexible platform that is adjusted to more accurately fit against the lower back (vs. a planar array currently used, but for curved lower spine with increasingly angulated discs toward the lower lumbar and sacral regions). Further to this approach, the relative locations and orientations of the detector coils may be sensed, with proper coordinate system assigned thereto for sequencing and acquisition during single voxel MRS of the spine (especially intervertebral discs), and which also may be adapted relative to coordinates of voxel orientation, dimensions, and shape.

T1-Rho:

An additional MRI-based pulse sequence technology has been previously disclosed called "T1-Rho". This is a sequence that has been alleged for detecting, measuring, and indicating the amount (e.g. concentration) of proteoglycan, via n-acetyl or n-acetyl acetate, in tissue, and furthermore for using this information for diagnostic benefit for some conditions. In one particular regard, this has been alleged to be potentially useful for monitoring degree of degeneration, in that reduced proteoglycan in discs may correlate to advancing degree of degeneration. While pain correlation with proteoglycan variability has not been determined, the ration of PG to other metabolites, such as for example Lactate (and/or alanine), is believed to be a consistent and potent indicator for localized discogenic pain. Accordingly, the present disclosure combines T1-Rho with other measurements, e.g. MRS measurements, in evaluating tissue chemistry for purpose of performing a diagnosis. In one particular mode contemplated hereunder, the T1-Rho measurement of proteoglycan/n-acetyl content is used to "normalize" or otherwise calibrate or compare an MRS measurement of that related region. In doing so, other metabolites in the MRS spectrum may be also calibrated for more accurately calculated "concentration" measurement. This calibration may be done in evaluating MRS signal quality, such as for example between channels or within a channel itself, and MRS data is used for the diagnosis. In a further mode, T1-Rho information related to PG may be used as the data for that chemical constituent in tissue, and data for another diagnostically relevant chemical, e.g. Lactate as measured for example via MRS (or other modality), may be used in combination with the PG measurement in an overall diagnostic algorithm or evaluation. Such algorithms applied for diagnostic use may be empirically driven based upon experimental data which may be conducted and acquired by one of ordinary skill for such purpose based upon this disclosure. For example, a database of sufficient patient data based on T1-rho measurements (for proteoglycan) and MRS measurements (such as for PG and/or Lactate, for example) may be correlated in a multi-variate logistic regression analysis against other pain indicators such as provocative discography or treatment outcomes, resulting in a highly correlative algorithm based upon the data fit. This may then be used prospectively in predicting or assessing localized pain in newly evaluated patient tissues. In one particular benefit, MRS techniques include particular sequence parameters that emphasize lactate for improved lactate-related data extraction, and decreasing lipid artifact (which often overlays over lactate to confound lactate data collection), but not considered as robust for other chemicals, such as potentially PG/n-acetyl. One such technique extends the time delay from magnetic activation to data collection, thus increasing overall time for repetitive scans. However, T1-Rho is relatively fast to perform relative to MRS. Accordingly, one particular further embodiment uses T1-rho for PG measurement, and MRS as enhanced for lactate measurement, and combines this data into an empirically data-driven algorithm for performing a diagnosis. Moreover, a further aspect contemplated hereunder uses T1-rho for PG measurement, in combination with pH or pO2 measurement (e.g. via a sensor on a needle, such as a discography needle) to monitor local acidity in the disc (also believed to relate to lactate concentration).

Diagnostic Display "Enhancing" MRI Images

The various aspects, modes, and embodiments of the present disclosure provide, among other beneficial advancements, a significant enhancement and improvement to standard MRI for locally diagnosing painful and/or non-painful discs. The utility of each of these diagnoses—painful, and non-painful—is of independent value on its own. While indicating a disc is definitively painful may often augment other clinical or diagnostic indications for directing treatment to the level, indicating a disc is definitively not painful also provides valuable information to exclude a disc as possible pain culprit and avoid unnecessary intervention to the level (especially where other clinical or diagnostic indications may indicate another level as painful, but not provide definitive answer to the other level/s). This is for example often the case with respect to L3-L4 and L4-L5 discs, where L5-S1 discs (most prevalently painful among the levels) may often be already suspect per MRI and other indications, but the higher adjacent disc levels are indeterminate.

The present aspects have been presented in terms of physical embodiments evaluated in clinical study with highly accurate results against controls. By providing a non-invasive alternative to discography as presented by these present embodiments, even if diagnostically equivalent, significant benefits are advanced by avoiding morbidity, pain, and other inefficiencies and downsides associated with that invasive test.

As an enhancement to MRI, further aspects of the present disclosure provide useful diagnostic display to indicate the results in overlay context onto the MRI image itself and providing context to the structures revealed therein.

Figure 32A:
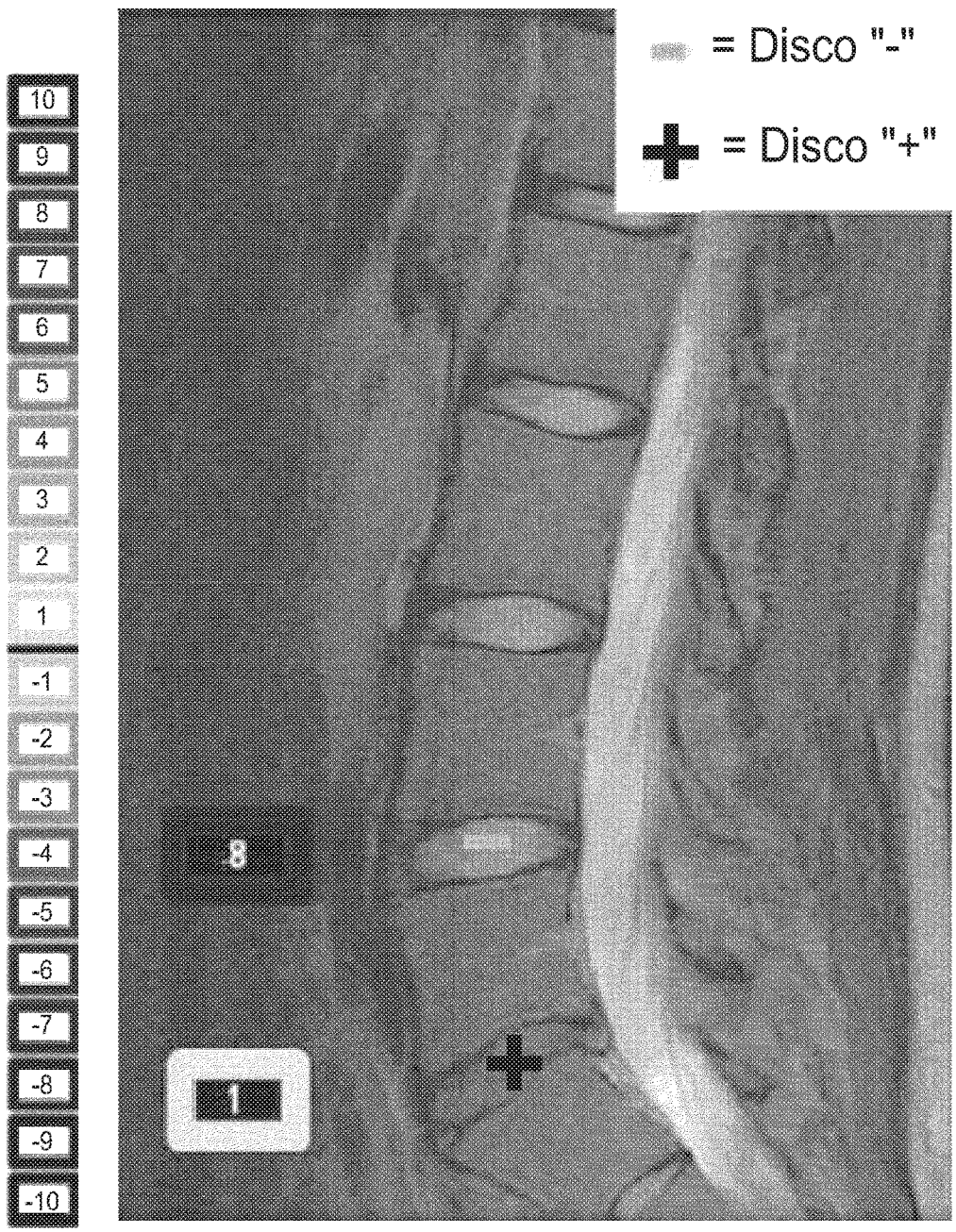
FIG. 32A shows a mid-sagittal T2-weighted MRI image of a patient evaluated under the clinical study of Example 1 and comparing the diagnostic results of the physical embodiment DDD-MRS system developed according to various aspects hereunder against provocative discography results for the same discs, and shows a color-coded, number-coded diagnostic legend for the DDD-MRS results (on left of image) and discogram legend (top right on image) with overlay of the DDD-MRS results and discogram results on discs evaluated in the patient.
Figure 32B:
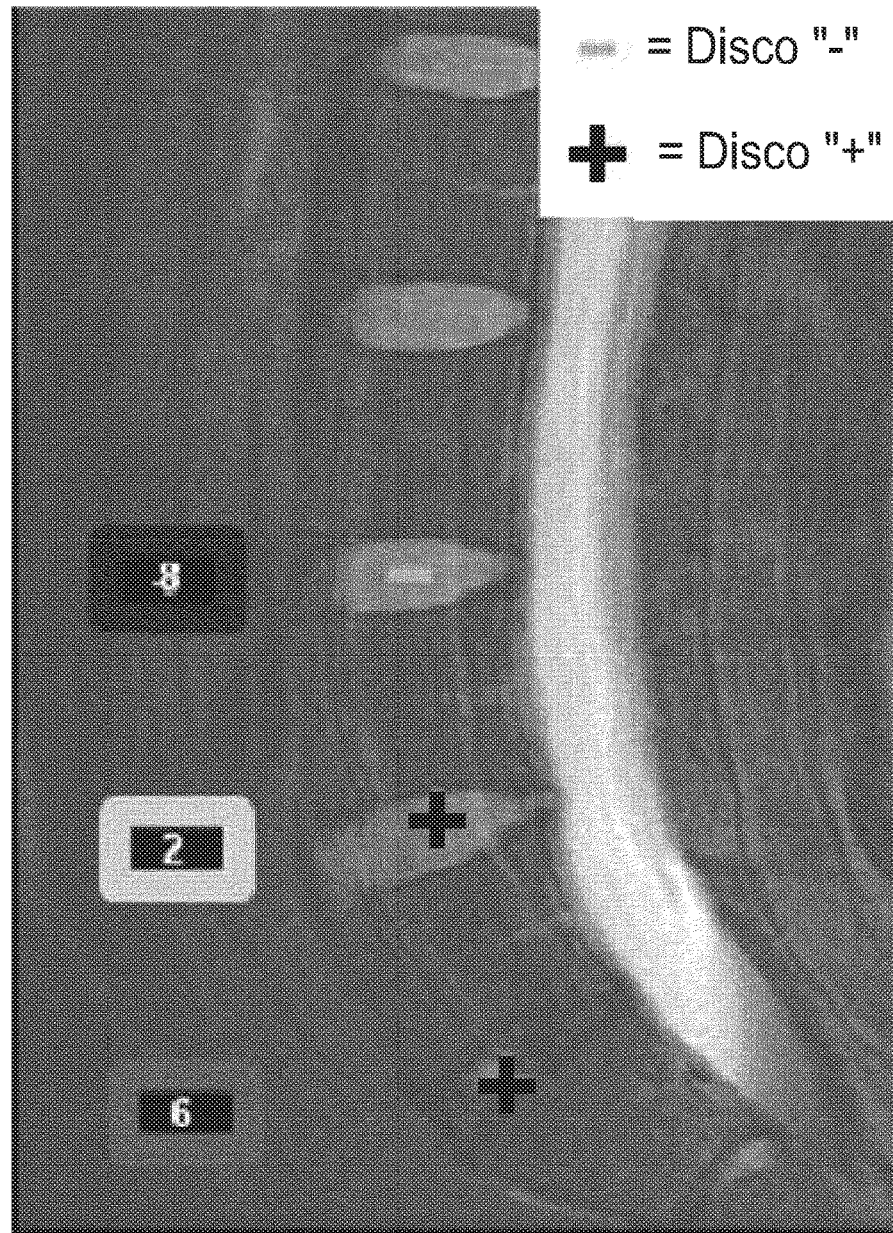
FIG. 32B shows a mid-sagittal T2-weighted MRI image of another patient evaluated under the clinical study of Example 1 and comparing the diagnostic results of the physical embodiment DDD-MRS system developed according to various aspects hereunder against provocative discography results for the same discs, and shows a color-coded, number-coded diagnostic legend for the DDD-MRS results (on left of image) and discogram legend (top right on image) with overlay of the DDD-MRS results and discogram results on discs evaluated in the patient.

FIGS. 32A and 32B show two different examples of DDD-MRS diagnostic display results for two different patients in the clinical study featured under Example 1 hereunder. These patients have similar disc degeneration profiles as seen on the MRI images, with dark disc at L5-S1 and relatively healthy discs revealed above at L4-L5 and L3-L4 in each patient. As also shown in each of these figures, both patients also had positive discogram results at L5-S1. However, as also shown in these two comparison Figures, the patient featured in FIG. 32A had a negative discogram result (e.g. non-painful diagnosis) at L4-L5, whereas the patient featured in FIG. 32B had a positive discogram result (e.g. painful diagnosis) at that level—despite having similar disc degeneration profile. As a consequence of both exams, with modern discography technique guidelines indicating requirement for a negative control disc before positive levels may be accepted results, the patients each had another negative discogram done at the L3-L4 (FIG. 32A) and L4-L5 (FIG. 32B) levels, respectively, to provide the required negative control level. As an awarded recent study has shown discography significantly increases disc degeneration & herniations rates, the result of both of these studies, if followed for directed intervention, would have resulted in treating the positive discogram levels, but not the negative discogram levels—leaving those untreated levels in place to potentially accelerate in degeneration & toward possible herniations. As shown in these Figures, the non-invasive DDD-MRS results matched these invasive discography results at all disc levels. The DDD-MRS approach provides the distinct benefit of providing the diagnostic information required, while leaving all discs uncompromised due to the non-invasive nature of the approach.

Turning now to FIGS. 33A-C. The volume excitation achieved using PRESS takes advantage of three orthogonal slices in the form of a double spin echo to select a specific region of interest. In some embodiments, the range of chemical shift frequencies (over 400 Hz for proton at 3.0T) is not insignificant relative to the limited band width of most excitation pulses (1000-2000 Hz). The result can be a misregistration of the volume of interest for chemical shift frequencies not at the transmitter frequency. Thus, when a PRESS volume is resolved by MRS, the chemical levels may be not only dependent on tissue level, T1 and T2, but also dependent on location within the volume of interest. In some embodiments, due to imperfections in the RF pulse, out of volume excitation may occur which can present signals from chemicals that are not in the frequency/location range of interest. Very selective saturation (VSS) bands are shown in FIGS. 33A-C.

The following issued US patents are also herein incorporated in their entirety by reference thereto: U.S. Pat. Nos. 5,617,861; 5,903,149; 6,617,169; 6,835,572; 6,836,114; 6,943,033; 7,042,214; 7,319,784.

The following pending US Patent Application Publication is herein incorporated in its entirety by reference thereto: US2007/0253910.

The following PCT Patent Application Publication is also herein incorporated in its entirety by reference thereto: WO2009/058915.

Some aspects of the systems and methods described herein can advantageously be implemented using, for example, computer software, hardware, firmware, or any combination of computer software, hardware, and firmware. Computer software can comprise computer executable code stored in a computer readable medium that, when executed, performs the functions described herein. In some embodiments, computer-executable code is executed by one or more general purpose computer processors. A skilled artisan will appreciate, in light of this disclosure, that any feature or function that can be implemented using software to be executed on a general purpose computer can also be implemented using a different combination of hardware, software, or firmware. For example, such a module can be implemented completely in hardware using a combination of integrated circuits. Alternatively or additionally, such a feature or function can be implemented completely or partially using specialized computers designed to perform the particular functions described herein rather than by general purpose computers.

A skilled artisan will also appreciate, in light of this disclosure, that multiple distributed computing devices can be substituted for any one computing device illustrated herein. In such distributed embodiments, the functions of the one computing device are distributed (e.g., over a network) such that some functions are performed on each of the distributed computing devices.

While certain embodiments of the disclosure have been described, these embodiments have been presented by way of example only, and are not intended to limit the scope of the broader aspects of the disclosure. Indeed, the novel methods, systems, and devices described herein may be embodied in a variety of other forms. For example, embodiments of one illustrated or described DDD-MRS system component may be combined with embodiments of another illustrated or described DDD-MRS system component. Moreover, the DDD-MRS system components described above, e.g. pulse sequence, signal processor, or diagnostic processor, may be utilized for other purposes. For example, an MRS system (or component sequence, signal processor, or diagnostic processor useful therewith or thereunder), may be configured and used in manners consistent with one or more broad aspects of this disclosure for diagnosing other tissue environments or conditions than pain within an intervertebral disc. Or, such may be usefully employed for diagnosing pain or other tissue environments or conditions in other regions of interest within the body. Such further applications are considered within the broad scope of disclosure contemplated hereunder, with or without further modifications, omissions, or additions that may be made by one of ordinary skill for a particular purpose. Furthermore, various omissions, substitutions and changes in the form of the methods, systems, and devices described herein may be made without departing from the spirit of the disclosure. Components and elements may be altered, added, removed, or rearranged. Additionally, processing steps may be altered, added, removed, or reordered. While certain embodiments have been explicitly described, other embodiments will also be apparent to those of ordinary skill in the art based on this disclosure.

What is claimed is:

1. A magnetic resonance spectroscopy (MRS) method for generating and processing a multi-frame MRS spectral acquisition series of data for a voxel located within a region of interest (ROI) in a patient to thereby provide a processed MRS spectrum from which spectral data may be extracted and processed to provide MRS-based diagnostic information for a medical condition associated with the ROI, the method comprising:
    applying a first MRS pulse sequence to produce a set of unsuppressed water free induction decay (FID) frames acquired using multiple acquisition channels of a multi-coil detector assembly;
    applying a second MRS pulse sequence to produce a set of suppressed water FID frames acquired using the multiple acquisition channels of the multi-coil detector assembly; and
    signal processing the MRS spectral acquisition series of data, wherein the signal processing is performed by at least one computer processor, and wherein the signal processing comprises:
        selecting one or more channels among the multiple acquisition channels for further processing to generate the processed spectrum, wherein the selection of the one or more channels is based at least in part on the set of unsuppressed water FID frames for each of the channels;
        identifying phase shift error using the set of unsuppressed water FID frames;
        applying phase shift correction to the set of suppressed water FID frames, wherein the phase shift correction is configured to at least partially correct the phase shift error determined using the set of unsuppressed water FID frames; and
        combining at least some of the phase shift corrected frames from the set of suppressed water FID frames from the one or more selected channels to at least in part produce the processed MRS spectrum.

2. The method of claim 1, wherein the selecting one or more channels is performed before the identifying phase shift error and the applying phase shift correction.

3. The method of claim 1, wherein the selecting one or more channels comprises:
    determining a signal to noise ratio for the unsuppressed water FID frames for each of the channels; and
    selecting for inclusion the channel with the greatest signal to noise ratio.

4. The method of claim 3, wherein the selecting one or more channels comprises selecting for inclusion one or more additional channels that have a signal to noise ratio within a threshold range of the greatest signal to noise ratio.

5. The method of claim 1, wherein the identifying phase shift error comprises fitting a polynomial to the phase of one or more frames of the set of unsuppressed water FID frames.

6. The method of claim 5, wherein the identifying phase shift error comprises determining a mean phase of one or more frames of the set of unsuppressed water FID frames.

7. The method of claim 1, wherein the signal processing further comprises:
    identifying one or more exclusion frames in the set of water suppressed FID frames based upon at least one threshold frame editing criterion; and
    excluding the identified one or more exclusion frames from the combining of the frames to produce the processed MRS spectrum.

8. The method of claim 1, wherein the signal processing further comprises identifying and correcting frequency shift error in the set of water suppressed FID frames.

9. The method of claim 1, wherein the region of interest (ROI) comprises at least a portion of an intervertebral disc.

10. A magnetic resonance spectroscopy (MRS) system configured to generate and process a multi-frame MRS spectral acquisition series of data for a voxel within a region of interest (ROI) in a patient to provide a processed MRS spectrum from which spectral data may be extracted and processed to provide diagnostic information for a medical condition associated with the ROI, the system comprising:
    an MR system comprising an MR scanner and a multi-coil detector assembly, and that is configured to use at least one MRS pulse sequence to non-invasively generate and acquire the MRS spectral acquisition series of data from the ROI using multiple acquisition channels of the multi-coil detector assembly, wherein the MRS spectral acquisition series of data comprises:
        a set of unsuppressed water free induction decay (FID) frames; and
        a set of suppressed water FID frames;
    an automated MRS signal processor configured to receive and process the MRS spectral acquisition series of data to generate the processed MRS spectrum, the automated MRS signal processor comprising at least one of:
        (a) a channel selector configured to select one or more channels among the multiple acquisition channels for further processing to generate the processed spectrum, wherein the channel selector is configured to select the one or more channels based at least in part on the set of unsuppressed water FID frames for each of the channels; and
        (b) a phase shift corrector configured to identify phase shift error using the set of unsuppressed water FID frames and to apply phase shift correction to the set of suppressed water FID frames, wherein the phase shift correction is configured to at least partially correct the phase shift error determined using the set of unsuppressed water FID frames;
    wherein the automated MRS signal processor comprises a frame combiner configured to combine at least some frames from the set of suppressed water FID frames to at least in part produce the processed MRS spectrum; and wherein the automated MRS signal processor comprises at least one of:
(a) at least one computer processor; and
(b) software provided in computer readable non-transitory storage and that is configured to be run by at least one computer processor.

11. The system of claim 10, wherein the automated MRS signal processor comprises a frame editor configured to identify one or more exclusion frames in the set of suppressed water FID frames based upon at least one threshold frame editing criterion, and wherein the frame combiner excludes the one or more exclusion frames to produce the processed MRS spectrum.

12. The system of claim 10, wherein the automated MRS signal processor comprises a frequency shift error corrector configured to identify and correct a frequency shift error in the set of water suppressed FID frames.

13. The system of claim 10, wherein the automated MRS signal processor comprises the channel selector.

14. The system of claim 13, wherein the channel selector is configured to:
determine a signal to noise ratio for the unsuppressed water FID frames for each of the channels; and
select for inclusion the channel with the greatest signal to noise ratio.

15. The system of claim 14, wherein the channel selector is configured to select for inclusion one or more additional channels that have a signal to noise ratio within a threshold range of the greatest signal to noise ratio.

16. The system of claim 10, wherein the automated MRS signal processor comprises the phase shift corrector.

17. The system of claim 16, wherein the phase shift corrector is configured to fit a polynomial to the phase of one or more frames of the set of unsuppressed water FID frames.

18. The system of claim 10, wherein the automated MRS signal processor comprises the channel selector and the phase shift corrector.

19. The system of claim 10, wherein the region of interest (ROI) comprises at least a portion of an intervertebral disc.

20. A magnetic resonance spectroscopy (MRS) system configured to process a multi-frame MRS spectral acquisition series of data generated and acquired from a voxel within a region of interest (ROI) in a patient via an MRS pulse sequence operation of an MRS system, and to provide a processed MRS spectrum from which spectral data may be extracted and processed to provide diagnostic information for a medical condition associated with the ROI, comprising:
an automated MRS signal processor configured to:
receive the MRS spectral acquisition series of data that comprises:
a first set of free induction decay (FID) frames; and
a second set of FID frames, wherein the second set of FID frames has more water suppression than the first set of FID frames;
perform one or more signal processing operations based at least in part on the first set of FID frames, wherein the one or more signal processing operations modify the second set of FID frames; and
combine at least some frames from the second set of FID frames to at least in part produce the processed MRS spectrum;
wherein the automated MRS signal processor comprises at least one of:
(a) at least one computer processor; and
(b) software provided in computer readable non-transitory storage and that is configured to be run by at least one computer processor.

21. The system of claim 20, wherein the automated MRS signal processor comprises a channel selector configured to select one or more channels among multiple acquisition channels for further processing to generate the processed spectrum, wherein the channel selector is configured to select the one or more channels based at least in part on the first set of FID frames for each of the channels.

22. The system of claim 20, wherein the automated MRS signal processor comprises a phase shift corrector configured to identify phase shift error using the first set of FID frames and to apply phase shift correction to the second set of FID frames, wherein the phase shift correction is configured to at least partially correct the phase shift error determined using the first set of FID frames.

23. The system of claim 20, wherein the first set of FID frames are unsuppressed water FID frames.

24. The system of claim 20, further comprising an MRS diagnostic processor configured to process the processed MRS spectrum to:
extract a first measurement from a first spectral peak region corresponding with proteoglycan (PG);
extract at least one additional measurement from at least one additional spectral peak region corresponding with each of lactate (LA) and alanine (AL); and
generate the diagnostic information for the medical condition associated with the ROI using the first measurement and the at least one additional measurement.

* * * * *